(12) United States Patent
Larisch et al.

(10) Patent No.: US 11,866,409 B2
(45) Date of Patent: Jan. 9, 2024

(54) APOPTOSIS RELATED PROTEIN IN THE TGF-BETA SIGNALING PATHWAY (ARTS) MIMETIC COMPOUNDS, COMPOSITIONS, METHODS AND USES THEREOF IN INDUCTION OF DIFFERENTIATION AND/OR APOPTOSIS OF PREMALIGNANT AND MALIGNANT CELLS, THEREBY RESTORING THEIR NORMAL-LIKE PHENOTYPE

(71) Applicant: CARMEL-HAIFA UNIVERSITY ECONOMIC CORPORATION LTD., Haifa (IL)

(72) Inventors: Sarit Larisch, Zichron Yaakov (IL); Dalit Barkan, Zichron Yaakov (IL)

(73) Assignee: CARMEL-HAIFA UNIVERSITY ECONOMIC CORPORATION LTD., Haifa (IL)

(*) Notice: Subject to any disclaimer, the term of this patent is extended or adjusted under 35 U.S.C. 154(b) by 0 days.

(21) Appl. No.: 15/772,699

(22) PCT Filed: Nov. 2, 2016

(86) PCT No.: PCT/IL2016/051187
§ 371 (c)(1),
(2) Date: May 1, 2018

(87) PCT Pub. No.: WO2017/077535
PCT Pub. Date: May 11, 2017

(65) Prior Publication Data
US 2018/0230096 A1    Aug. 16, 2018

Related U.S. Application Data

(60) Provisional application No. 62/249,446, filed on Nov. 2, 2015.

(51) Int. Cl.
| | | |
|---|---|---|
| C07D 209/42 | (2006.01) | |
| C07D 231/14 | (2006.01) | |
| C07D 217/02 | (2006.01) | |
| A61K 31/496 | (2006.01) | |
| A61K 45/06 | (2006.01) | |
| A61P 35/00 | (2006.01) | |

(52) U.S. Cl.
CPC .......... C07D 209/42 (2013.01); A61K 31/496 (2013.01); A61K 45/06 (2013.01); A61P 35/00 (2018.01); C07D 217/02 (2013.01); C07D 231/14 (2013.01)

(58) Field of Classification Search
CPC ..... C07D 209/42; C07D 231/14; A61P 35/00; A61K 31/496
See application file for complete search history.

(56) References Cited

U.S. PATENT DOCUMENTS

| | | | |
|---|---|---|---|
| 5,491,153 A | 2/1996 | Salituro et al. | |
| 8,445,679 B2 * | 5/2013 | Wang | C07D 209/34 544/364 |
| 2005/0227302 A1 * | 10/2005 | Larisch | G01N 33/5011 435/7.23 |
| 2009/0118135 A1 * | 5/2009 | Reed | G01N 33/574 506/9 |
| 2009/0124616 A1 * | 5/2009 | Song | C07D 209/42 514/235.2 |

FOREIGN PATENT DOCUMENTS

| | | |
|---|---|---|
| WO | 2005/105213 A2 | 11/2005 |
| WO | 2006/126198 A2 | 11/2006 |
| WO | 2008/131000 A2 | 10/2008 |
| WO | 2009/076665 A1 | 6/2009 |
| WO | 2011106650 A2 | 9/2011 |
| WO | 2013/121428 A1 | 8/2013 |
| WO | 2014/047427 A2 | 3/2014 |
| WO | 2015/031608 A1 | 3/2015 |

OTHER PUBLICATIONS

RW Craig, Leukemia, (2002), v16, p. 444-454. (Year: 2002).*
Soini, et al, Clinical Cancer Research, 5, (1999), pp. 3508-3515. (Year: 1999).*
Fuchs et al., "Programmed Cell Death in Animal Development and Disease", Cell, vol. 147, pp. 1-17, (2011).
Gottfried et al., "The mitochondrial ARTS protein promotes apoptosis through targeting XIAP", EMBO J., vol. 23, pp. 1627-1635, (2004).
Larisch et al., "A novel mitochondrial septin-like protein, ARTS, mediates apoptosis dependent on its P-loop motif", Nat Cell Biol., vol. 2, pp. 915-921, (2000).
Edison et al., "The IAP-antagonist ARTS initiates caspase activation upstream of cytochrome C and SMAC/Diablo" Cell Death Differ., vol. 19, pp. 356-368, (2012b).
Bornstein et al., "ARTS binds to a distinct domain in XIAP-BIR3 and promotes apoptosis by a mechanism that is different from other IAP antagonists", Apoptosis, vol. 16, pp. 869-881, (2011).
Reingewertz et al., "Mechanism of the Interaction between the Intrinsically Disordered C-Terminus of the Pro-Apoptotic ARTS Protein and the Bir3 Domain of XIAP", PLoS One, vol. 6, Issue 9, e24655, (2011).

(Continued)

*Primary Examiner* — Kamal A Saeed
(74) *Attorney, Agent, or Firm* — Vorys, Sater, Seymour and Pease LLP; Anthony P. Venturino; Maryellen Feehery Hank

(57) ABSTRACT

Provided are ARTS mimetic compounds that act as novel antagonists for XIAP and Bcl-2. Further, the novel ARTS mimetic compounds of the presently claimed subject matter induce apoptosis and/or differentiation in premalignant and malignant cells and thereby restore their normal-like phenotype. Further provided are compositions, methods and uses of said ARTS mimetic compounds in the treatment of cancer and premalignant conditions.

18 Claims, 13 Drawing Sheets
Specification includes a Sequence Listing.

(56) References Cited

OTHER PUBLICATIONS

Adams et al., "Life-or-death decisions by the Bcl-2 protein family", Trends Biochem Sci., vol. 26, pp. 61-66, (2001).
Youle et al., "The BCL-2 protein family: opposing activities that mediate cell death", Nat Rev Mol Cell Biol., vol. 9, pp. 47-59, (2008).
Happo et al., "BH3-only proteins in apoptosis at a glance", J Cell Sci., vol. 125, pp. 1081-1087, (2012).
Edison et al., "Peptides mimicking the unique ARTS-XIAP binding site promote apoptotic cell death in cultured cancer cells" Clin Cancer Res, (2012a).
Bornstein et al., "X-linked Inhibitor of Apoptosis Protein promotes the degradation of its antagonist, the pro-apoptotic ARTS protein", Int J Biochem Cell Biol., vol. 44, pp. 489-495, (2012).
Barkan et al., "Inhibition of Metastatic Outgrowth from Single Dormant Tumor Cells by Targeting the Cytoskeleton", Cancer Research, vol. 68, No. 15, pp. 6241-6250, (2008).
Debnath et al., "Morphogenesis and oncogenesis of MCF-10A mammary epithelial acini grown in three-dimensional basement membrane cultures", Methods, vol. 30, No. 3, pp. 256-268, (2003).
Bissell et al., "Putting Tumours in Context", Nature Reviews Cancer, vol. 1, No. 1, pp. 46-54, (2001).
Myal et al., "Claudin 1 in Breast Tumorigenesis: Revelation of a Possible Novel "Claudin High" Subset of Breast Cancers", J Biomed Biotechnol., vol. 2010, Article ID 956897, 9 pages, (2010).
Muthuswamy et al., "ErbB2, but not ErbB1, reinitiates proliferation and induces luminal repopulation in epithelial acini", Nature Cell Biology, vol. 3, No. 9, pp. 785-792, (2001).
GenBank Accession No. AF176379, retrieved online Sep. 13, 2018.
GenBank Accession No. NP_000624, retrieved online Sep. 13, 2018.
GenBank Accession No. NM_000633, retrieved online Sep. 13, 2018.
GenBank Accession No. NM_000657, retrieved online Sep. 13, 2018.
GenBank Accession No. NP_001158, retrieved online Sep. 13, 2018.
GenBank Accession No. NP_001191330, retrieved online Sep. 13, 2018.
GenBank Accession No. NM_001167, retrieved online Sep. 13, 2018.
GenBank Accession No. NM_001204401, retrieved online Sep. 13, 2018.
GenBank Accession No. CAA80661, retrieved online Sep. 13, 2018.
GenBank Accession No. Z23115, retrieved online Sep. 13, 2018.
GenBank Accession No. AAF64255, retrieved online Sep. 13, 2018.
GenBank Accession No. AAB09055, retrieved online Sep. 13, 2018.
GenBank Accession No. NP_033872, retrieved online Sep. 13, 2018.
GenBank Accession No. NP_065129, retrieved online Sep. 13, 2018.
Gabrielli et al., BETA-Nitroacrylates as key building blocks for the synthesis of alkyl 3-substituted 5-oxopiperazine-2-carboxylates under fully heterogeneous conditions, Monatsch Chem, vol. 144, pp. 509-514, (2013).

Ahn et al., "Profiling Two Indole-2-Carboxamides for Allosteric Modulation of the CB1 Receptor" J Neurochem., vol. 124, No. 5, pp. 584-589, (2013).
Shiri et al., "Participation of ethyl 3-formylindole-2-carboxylate with the Ugi four-component condensation reaction", J Iran Chem Soc, vol. 11, pp. 85-90, (2014).
Akladios et al., "Design and synthesis of novel inhibitors of human kynurenine aminotransferase-1", Bioorganic & Medicinal Chemistry Letters, vol. 22, pp. 1579-1581, (2012).
CAS registry No. 375835-04-4, CA index name: 1H-Indole-2-carboxylic acid, 5-chloro-3-[[2-[4-(phenylmethyl)-1-piperazinyl]acetyl]amino]-, methyl ester, retrieved online Oct. 29, 2018.
Friberg et al., Discovery of potent myeloid cell leukemia 1 (Mcl 1) inhibitors using fragment based methods and structure based design, J Med Chem., vol. 56, No. 1, pp. 15-30, (2013).
Seervi et al., "ERO1alpha-dependent endoplasmic reticulum-mitochondrial calcium flux contributes to ER stress and mitochondrial permeabilization by procaspase-activating compound-1 (PAC-1)", Cell Death and Disease, vol. 4, e968, 14 pages, (2013).
Lotan et al., "Regulation of the Proapoptotoic ARTS Protein by Ubiquitin-mediated Degradation", The Journal of Biological Chemistry, vol. 280, No. 27, pp. 25802-25810, (2005).
Benito et al., "Regulation and Function of Bcl-2 During Differentiation-Induced Cell Death in HL-60 Promyelocytic Cells", American Journal of Pathology, vol. 146, No. 2, pp. 481-490, (1995).
Palmieri et al., "Beta-Nitroacrylates as Useful Building Blocks for the Synthesis of Alkyl Indole-2-Carboxylates", Synlett, 2014, vol. 25, pp. 0128-0132.
PubChem, "Compound Summary: Methyl 3 {[(4-benzylpiperazin-1-yl)acetyl]amino}-5-chloro-1H-indole-2-carboxylate", 9 pages, Mar. 24, 2020, retrieved online at https://pubchem.ncbi.nlm.nih.gov/compound/1918281.
De Giorgi et al., "Targeting the BH3 Domain of Bcl-2 Family Proteins. A Brief History From Natural Products to Foldamers As Promising Cancer Therapeutic Avenues", Current Medicinal Chemistry, 2013, vol. 20, pp. 2964-2978. XP55585303.
Edison et al., "Peptides Mimicking the Unique ARTS-XIAP Binding Site Promote Apoptotic Cell Death in Cultured Cancer Cells", Clin Cancer Res, 2012, vol. 18, No. 9, pp. 2569-2578. XP55206410.
Mezentseva et al., "Synthesis and Biological Activity of Aminoacetyl Derivatives of Pyrrole and Indole", Pharmaceutical Chemistry Journal, Jun. 1991, vol. 25, Issue 6, pp. 371-374, Jan. 1, 1991 (Jan. 1, 1991), XP55585166 https://link.springer.com/content/pdf/10.1007/BF00772134.pdf.
Moll et al., "Phenylpiperazinylmethylindolecarboxylates and Derivatives as Selective D4-Ligands", Bioorganic & Medicinal Chemistry, 2002, vol. 10, pp. 1671-1679. XP55585340.
Reck et al., "Novel N-Linked Aminopiperidine Inhibitors of Bacterial Topoisomerase Type II: Broad-Spectrum Antibacterial Agents with Reduced hERG Activity", J. Med. Chem., 2011, vol. 54, No. 22, pp. 7834-7847. XP55361889.
Moustakas et al., "Mechanisms of TGF-beta signaling in regulation of cell growth and differentiation", Immunology Letters, 2002, vol. 82, pp. 85-91.
Schuster et al., "Mechanisms of TGF-beta-mediated apoptosis", Cell Tissue Res, 2002, vol. 307, pp. 1-14.

* cited by examiner

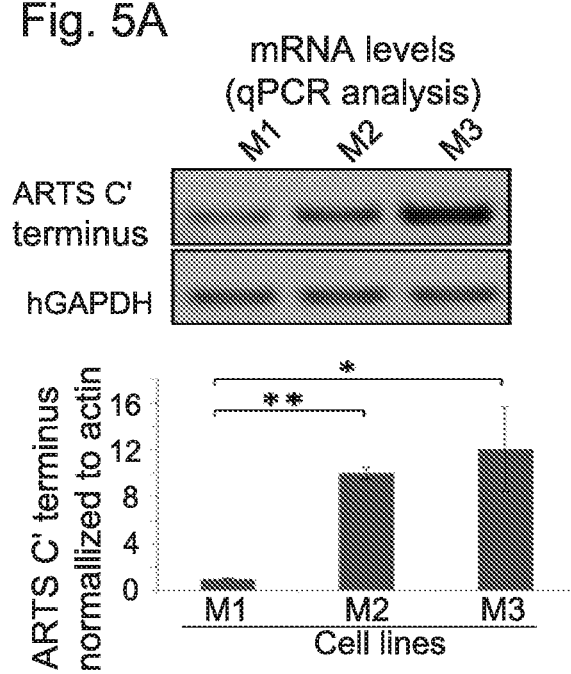
Fig. 5A
Fig. 5C
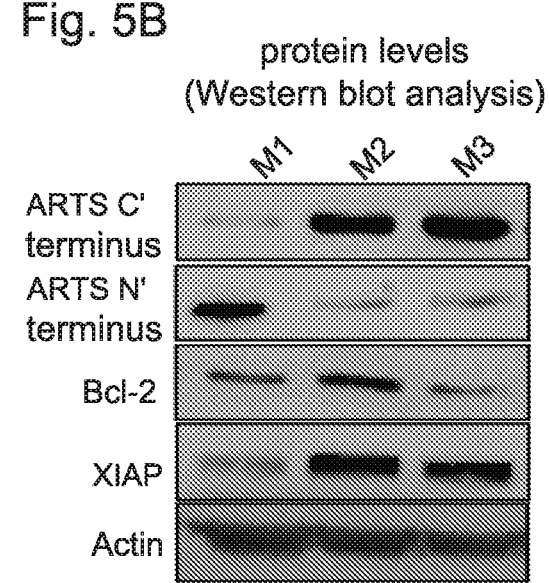
Fig. 5B
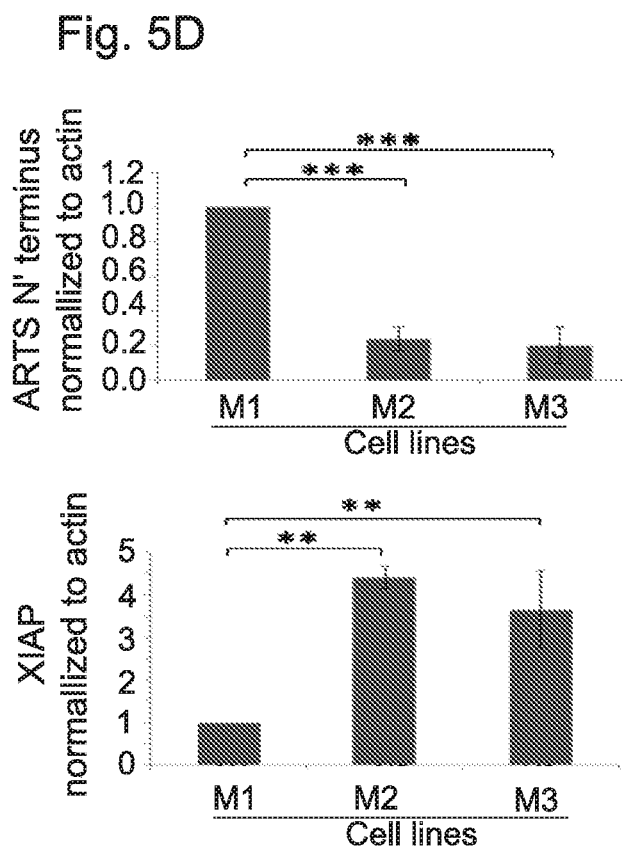
Fig. 5D
Fig. 5F
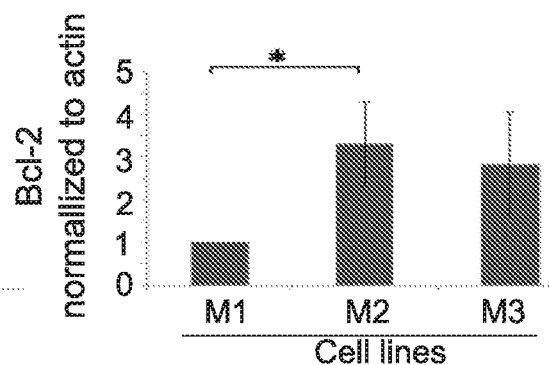
Fig. 5E

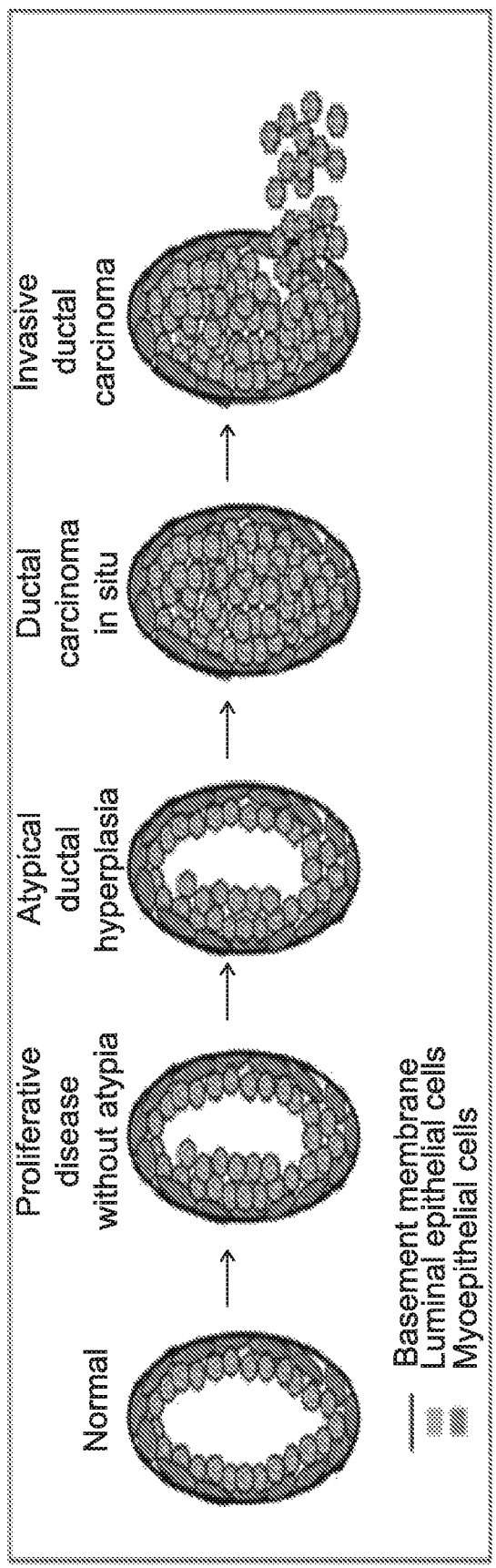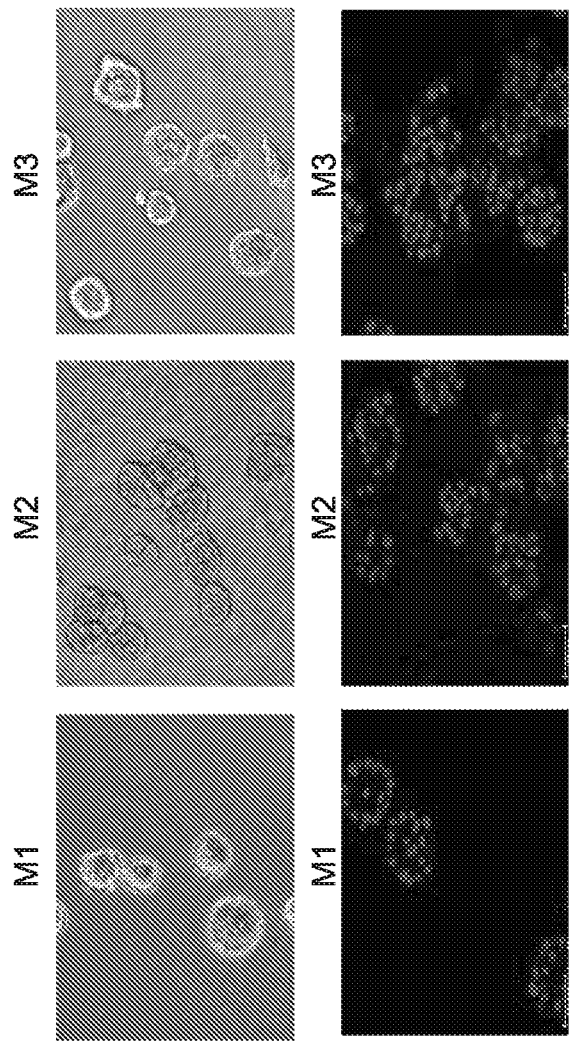
Fig. 8A
Fig. 8B
Fig. 8C

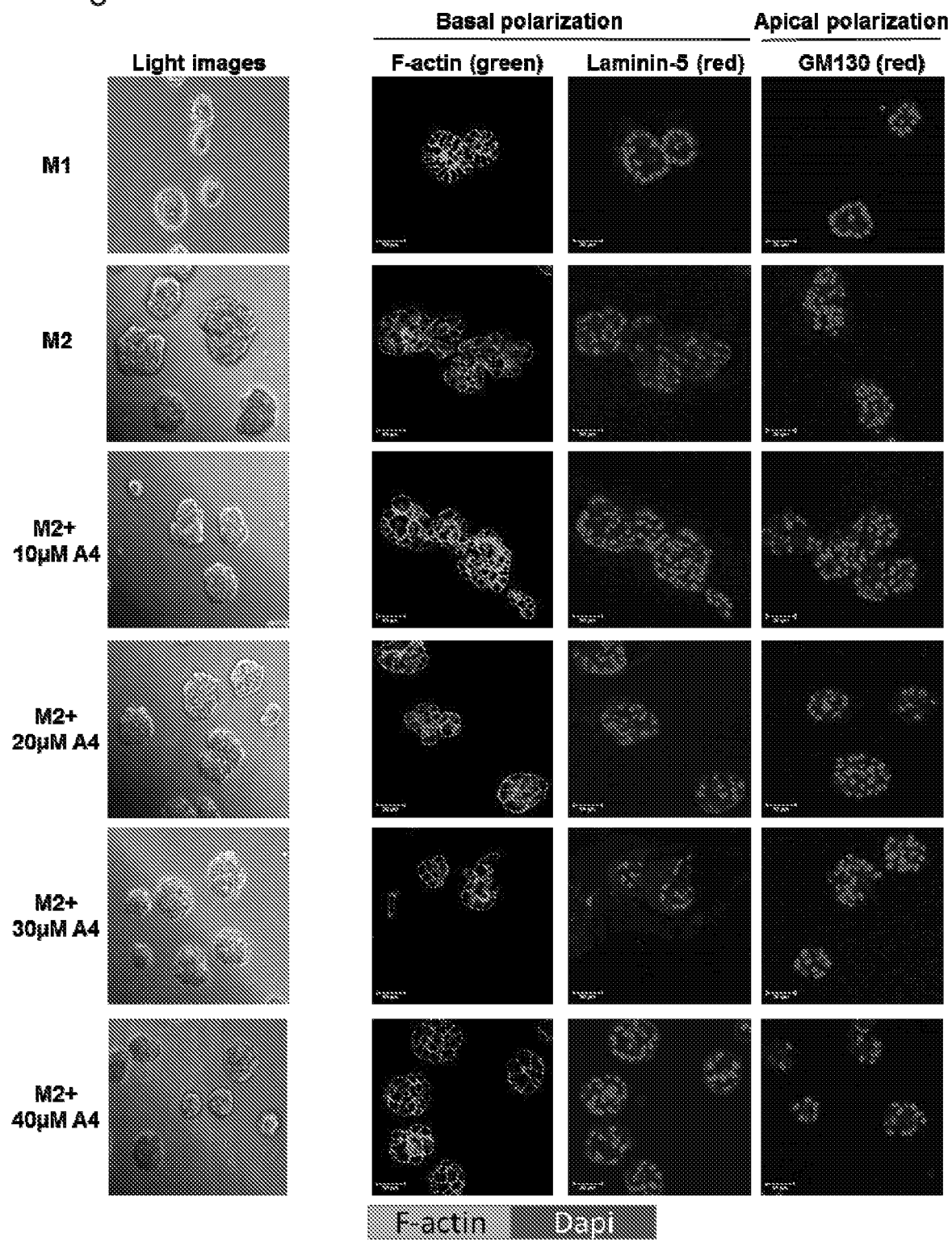

APOPTOSIS RELATED PROTEIN IN THE TGF-BETA SIGNALING PATHWAY (ARTS) MIMETIC COMPOUNDS, COMPOSITIONS, METHODS AND USES THEREOF IN INDUCTION OF DIFFERENTIATION AND/OR APOPTOSIS OF PREMALIGNANT AND MALIGNANT CELLS, THEREBY RESTORING THEIR NORMAL-LIKE PHENOTYPE

FIELD OF THE INVENTION

The invention relates to the field of cancer therapy. More particularly, the invention relates to novel ARTS mimetic compounds, compositions, uses and methods thereof for treating proliferative disorders and cancer, by inducing differentiation in malignant and pre-malignant cells and/or by inducing apoptosis. Thereby either kills cancer cells or reverses their malignant phenotype into a normal like phenotype.

PRIOR ART

References considered to be relevant as background to the presently disclosed subject matter are listed below:
Fuchs, Y., and H. Steller. *Cell.* 147:1-17 (2011).
Gottfried, Y., A. et al., *EMBO J.* 23:1627-35 (2004).
Larisch, S., et al., *Nat Cell Biol.* 2:915-21 (2000).
Edison, N., D. et al. *Cell Death Differ.* 19:356-68 (2012b).
Bornstein, B., Y. et al., *Apoptosis* 16:869-881 (2011).
Reingewertz, T. H., et al., *PLoS One.* 6:e24655 (2011).
Adams, J. M., and S. Cory. *Trends Biochem Sci.* 26:61-6 (2001).
Youle, R. J., and A. Strasser. *Nat Rev Mol Cell Biol.* 9:47-59 (2008).
Happo, L., A. et al., *J Cell Sci.* 125:1081-7 (2012).
Edison, N., T. H. et al., *Clin Cancer Res* (2012a).
Bornstein, B. N., et al., *Int J Biochem Cell Biol.* 44:489-95 (2012).
Barkan D. et al., *Cancer Research* 68 (15): 6241-50 (2008).
Debnath et al., Methods 30 (3): 256-68 (2003)
Bissell et al., Nature Reviews. Cancer 1(1): p. 46. (2001)
Myal et al., J Biomed Biotechnol. 956897. (2010).
Muthuswamy et al., Nature Cell Biology. 3(9): p. 785. (2001)

Acknowledgement of the above references herein is not to be inferred as meaning that these are in any way relevant to the patentability of the presently disclosed subject matter.

BACKGROUND OF THE INVENTION

Apoptosis is a process of programmed cell death that plays a major role in tissue development, tissue homeostasis, and as a defense mechanism against unwanted and potentially dangerous cells.

Apoptosis is controlled by a diverse range of cell signals which can originate either from extrinsic inducers thus activating the extrinsic, apoptotic signaling pathway or from intrinsic inducers, which activate the intrinsic, mitochondrial signaling pathway.

The control of apoptosis is achieved through the activity of pro- and anti-apoptotic proteins. For example, caspases are a family of cysteine proteases that play central executioners of apoptosis and the action of activators and inhibitors of caspases affect apoptosis. Inhibition of the caspases activity was reported to occur through the action of the inhibitor of apoptosis (IAP) proteins. Apoptosis has been reported to have a critical role in a variety of diseases. It has been shown that deregulation of the apoptosis pathway can result in various pathologic conditions, including cancer (Fuchs and Steller, 2011). Involvement of an abnormal ratio of pro- and anti-apoptotic proteins have been also associated with neurodegenerative diseases such as schizophrenia as well as in immune-related disorders.

To potentiate apoptosis, the function of IAPs needs to be overcome. This is achieved by IAP-antagonists such as Smac/Diablo, Omi/HtrA2 and ARTS (Gottfried et al., 2004; Larisch et al., 2000).

ARTS is localized at mitochondrial outer membrane (MOM) (Edison et al., 2012b). Upon induction of apoptosis, ARTS translocates from the mitochondria to the cytosol, directly binds and antagonizes XIAP, causing activation of caspases and cell death (Bornstein et al., 2011; Edison et al., 2012b; Reingewertz et al., 2011). XIAP, the best studied IAP, can directly bind and inhibit caspases 3, 7 and 9 via its three Baculoviral IAP Repeats (BIR) domains.

The inventors have previously shown that ARTS binds directly to distinct sequences within XIAP BIR3 (Bornstein et al., 2011; Edison et al., 2012b, Gottfried et al., 2004, ARTS binds to a distinct domain in XIAP-BIR3 and promotes apoptosis by a mechanism that is different from other IAP-antagonists (Bornstein et al, 2011). Moreover, ARTS uses a distinct binding domain to bind XIAP. AIBM—ARTS IAP Binding Motif are the last 27 to 68 amino acid residues localized at the C-terminal part of ARTS (Gottfried et al., 2004, Edison et al, 2012a, and WO2006126198).

The intrinsic pathway of apoptosis is regulated by Bcl-2 family members (Adams and Cory, 2001). This family is composed of pro- and anti-apoptotic proteins that share up to four conserved Bcl-2 homology (BH) domains (Youle and Strasser, 2008). The pro-apoptotic members can be separated into the "multidomain" proteins and to "BH3 only" proteins. Bax and Bak "multidomain" proteins which share three BH regions and structurally similar to the antiapoptotic proteins. The "BH3-only" proteins, which include Bnip3, Nix/Bnip3L, Bid, Noxa, Puma, and Bad, share only the BH3 domain and are structurally diverse (Happo et al., 2012).

The inventors have recently further shown that upon induction of apoptosis, ARTS binds directly to both XIAP and Bcl-2, acting as a scaffold to bring these proteins together. This binding leads to a UPS mediated degradation of Bcl-2. Moreover, the inventors have found that ARTS comprise a BH3-like domain. These data indicate that ARTS functions as a novel Bcl-2 antagonist and as such, allows degradation of Bcl-2 and inhibits the anti-apoptotic activity of Bcl-2 (WO 2013/121428).

There is need for novel compounds that target and inhibit both classes of pro-apoptotic proteins, the XIAP and Bcl-2. As ARTS functions in a distinct way, different from all known IAP-antagonists (Gottfried et al, 2004, Edison et al, 2012a, Bornstein et al, 2011, Bornstein et al, 2012) and as novel Bcl-2 antagonists, it offers a unique approach for anti-cancer therapies targeting the two major anti-apoptotic proteins. There is further need to develop compounds that induce differentiation in cells, thereby reversing a malignant phenotype of malignant cells into a normal phenotype. Such compound may be of particular relevance in early states of malignant transformation. These compounds may act in anti-cancer therapy reducing side effects caused by compound that induce cell death.

SUMMARY OF THE INVENTION

In accordance with this aspect, the present disclosure provides a compound having the general formula (I) including any stereoisomer or salt thereof, for use in a method for treating, preventing, inhibiting, reducing, eliminating, protecting or delaying the onset of a proliferative disorder in a subject in need thereof, wherein said formula (I) is:

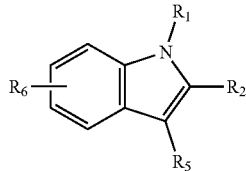

(I)

or a pharmaceutically acceptable salt, solvate, hydrate, any stereoisomer thereof or physiologically functional derivative thereof
wherein
$R_1$ may be independently selected from H, $C_1$-$C_{12}$ alkyl, $C_2$-$C_{12}$ alkenyl, $C_2$-$C_{12}$alkynyl;
$R_2$ may be independently selected from —C(=O)—X—$R_3$, —S(=O)—X—$R_3$;
X being a heteroatom independently selected from N-containing group, O and S;
$R_3$ and $R_{3'}$, independently of each other may be selected independently from H, $C_1$-$C_{12}$ alkyl, $C_2$-$C_{12}$ alkenyl, $C_2$-$C_{12}$alkynyl;
$R_5$ may be -L1-$R_7$-L2-$R_8$;
L1 and L2, independently of each other, may be selected independently from —$(CH_2)_n$—; —NH—C(=O)—$(CH_2)_n$—, —C(=O)—NH—$(CH_2)_n$—; —S—S—$(CH_2)_n$—; —O—$(CH_2)_n$—; —NH—$(CH_2)_n$—; C(=O)—$(CH_2)_n$—; —S—$(CH_2)_n$—; —NH—S(=O)$_n$ —$(CH_2)_n$—;
each n, being independently, may be 0 to 5;
$R_7$ may be independently selected from $C_1$-$C_{12}$ alkylene, $C_2$-$C_{12}$ alkenylene, $C_2$-$C_{12}$ alkynylene, a ring system containing five to twelve atoms, each optionally substituted;
$R_8$ may be independently selected from H, $C_1$-$C_{12}$ alkyl, $C_2$-$C_{12}$ alkenyl, $C_2$-$C_{12}$ alkynyl, a ring system containing five to twelve atoms, each optionally substituted;
$R_6$ may be independently selected from H, halogen, CN, $NO_2$, $C_1$-$C_{12}$ alkoxy, $C_1$-$C_{12}$ alkyl, $C_2$-$C_{12}$ alkenyl, $C_2$-$C_{12}$ alkynyl.

In some specific embodiments, the invention provides the compound for use, wherein the compound is methyl 5-chloro-3-[[2-[4-(phenylmethyl)piperazin-1-yl]acetyl]amino]-1H-indole-2-carboxylate also termed as 3-[2-(4-Benzyl-piperazin-1-yl)-acetylamino]-5-chloro-1H-indole-2-carboxylic acid methyl ester, also referred to as "A4" having the structure:

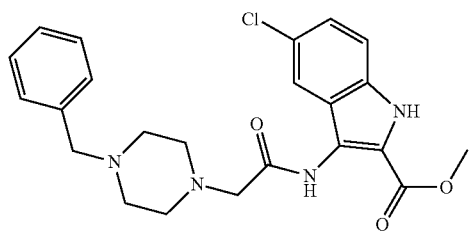 [SMILES: COC(=O)c1[nH]c2ccc(Cl)cc2c1NC(=O)CN1CCN(Cc2ccccc2)CC1]

or any stereoisomer or salt thereof.

In some embodiments, the compound referred to as "A4" may be or may comprise at least the following stereoisomer:

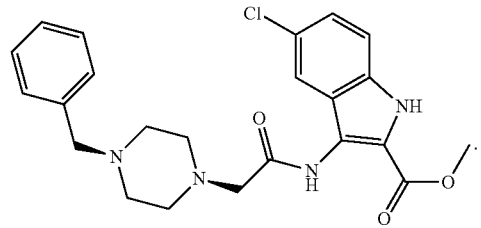

In yet a further aspect, the invention provides the use of any of the compounds described herein in a method for inducing differentiation and/or apoptosis in a cell.

In a further aspect, the invention relates to a composition comprising an effective amount of at least one ARTS mimetic compound having the general formula (I) as defined herein above, or a pharmaceutically acceptable salt or hydrate thereof or any stereoisomer or any vehicle, matrix, nano- or micro-particle comprising the same. In more specific embodiments, the invention provides the use of said compositions for use in a method for treating, preventing, inhibiting, reducing, eliminating, protecting or delaying the onset of a proliferative disorder in a subject in need thereof.

In yet a further aspect, the invention relates to a method for inducing differentiation in a cell. In more specific embodiments, the method comprising the step of contacting the cell with an effective amount of at least one of: ARTS or any functional fragment or peptide thereof, at least one ARTS mimetic compound as defined by the invention, any combination thereof or any composition comprising the same.

In yet another aspect, the invention provides a method for treating, preventing, inhibiting, reducing, eliminating, protecting or delaying the onset of a proliferative disorder in a subject in need thereof. In more specific embodiments the method comprising administering to such subject a therapeutically effective amount of at least one ARTS mimetic compound/s of the invention or of a composition comprising the same.

In a further aspect, the invention relates to a combined composition comprising a therapeutically effective amount of:
(a) any one of at least one BH3 mimetics compound and at least one pro-apoptotic member of the Bcl-2 family; and
(b) at least one ARTS mimetic compound as defined by the invention.

A further aspect of the invention relates to a kit comprising:
(a) at least one ARTS mimetic compound as defined by the invention, optionally, in a first dosage form; and
(b) any one of at least one BH3 mimetics compound, at least one pro-apoptotic protein member of the Bcl-2 family and any combinations thereof, optionally, in a second dosage form.

In yet a further aspect, the present disclosure provides a compound having the general formula (I):

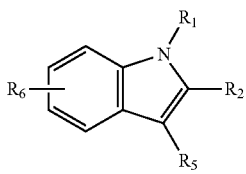

(I)

or a pharmaceutically acceptable salt, solvate, hydrate, or physiologically functional derivative thereof including any stereoisomer thereof wherein $R_1$ may be independently selected from H, $C_1$-$C_{12}$ alkyl, $C_2$-$C_{12}$ alkenyl, $C_2$-$C_{12}$ alkynyl;

$R_2$ may be independently selected from —C(=O)—X—$R_3$, —S(=O)—X—$R_{3'}$;

X being a heteroatom independently selected from N-containing group, O and S;

$R_3$ and $R_{3'}$, independently of each other may be selected independently from H, $C_1$-$C_{12}$ alkyl, $C_2$-$C_{12}$ alkenyl, $C_2$-$C_{12}$ alkynyl;

$R_5$ may be -L1-$R_7$-L2-$R_8$;

L1 and L2, independently of each other, may be selected independently from —(CH$_2$)$_n$—; —NH—C(=O)—(CH$_2$)$_n$—; —C(=O)—NH—(CH$_2$)$_n$—; —S—S—(CH$_2$)$_n$—; —O—(CH$_2$)$_n$—; —NH—(CH$_2$)$_n$—; C(=O)—(CH$_2$)$_n$; —S—(CH$_2$)$_n$—; —NH—S(=O)$_n$—(CH$_2$)$_n$—;

each n, being independently, may be 0 to 5;

$R_7$ may be independently selected from $C_1$-$C_{12}$ alkylene, $C_2$-$C_{12}$ alkenylene, $C_2$-$C_{12}$ alkynylene, a ring system containing five to twelve atoms, each optionally substituted;

$R_8$ may be independently selected from H, $C_1$-$C_{12}$ alkyl, $C_2$-$C_{12}$ alkenyl, $C_2$-$C_{12}$ alkynyl, a ring system containing five to twelve atoms, each optionally substituted;

$R_6$ may be independently selected from H, halogen, CN, NO$_2$, $C_1$-$C_{12}$ alkoxy, $C_1$-$C_{12}$ alkyl, $C_2$-$C_{12}$ alkenyl, $C_2$-$C_{12}$ alkynyl.

In some specific embodiments, the invention provides a compound denoted as methyl 5-chloro-3-[[2-[4-(phenylmethyl)piperazin-1-yl]acetyl]amino]-1H-indole-2-carboxylate also termed as 3-[2-(4-Benzyl-piperazin-1-yl)-acetylamino]-5-chloro-1H-indole-2-carboxylic acid methyl ester having the formula:

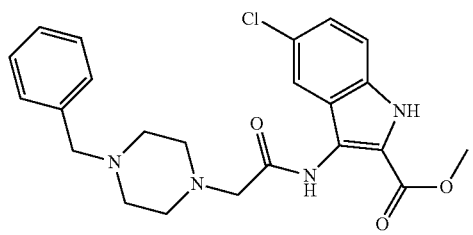 [SMILES: COC(=O)c1[nH]c2ccc(Cl)cc2c1NC(=O)CN1CCN(Cc2ccccc2)CC1]

including any stereoisomer or salt thereof. In some further specific embodiment, the compound may be or include a stereoisomer such as an enantiomer being:

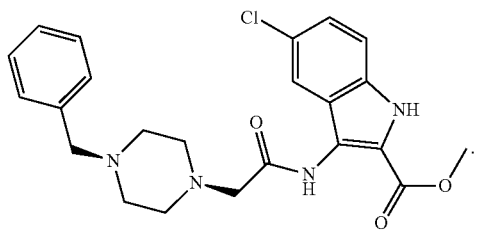

In yet another aspect, the invention provides a composition comprising any of the compounds of the invention, any vehicle, matrix, nano- or micro-particle, or composition comprising the same and optionally, at least one of pharmaceutically acceptable carrier/s, excipient/s, auxiliaries, and/or diluent/s.

These and other aspect of the invention will become apparent by the hand of the following drawings.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

Figure illustrates an "in silico" screen for ARTS mimetic small molecules that fit into the binding site of ARTS unique C-terminus and its distinct binding sequence in the BIR3 domain of XIAP.

Figure 2:
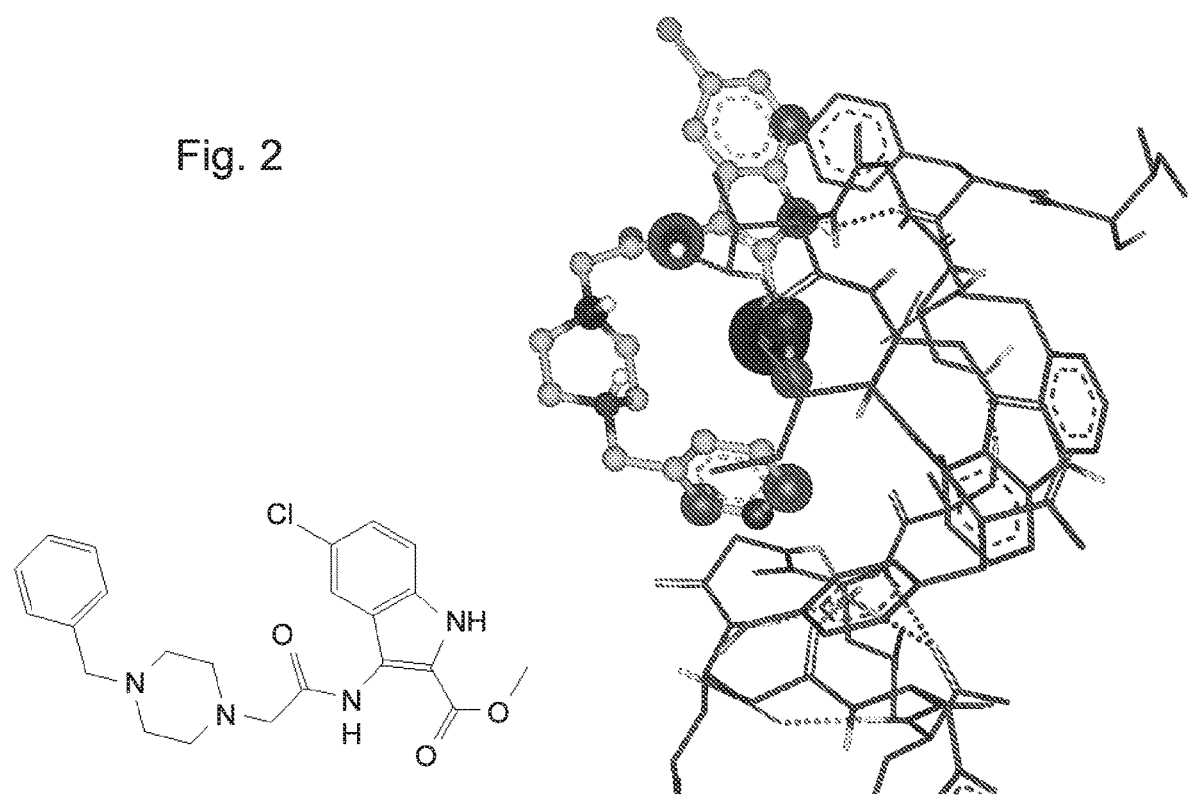

FIG. 2. Binding of A4 to BIR3-XIAP

Figure illustrates the molecular structure of the A4 (#4424446 in e-molecules) small molecule (in bold-nude) and its interaction with the ARTS binding site within the XIAP molecule. Favorable interactions of said candidate molecule with BIR3-XIAP are shown in green, where negative interaction is shown in red.

Figure 3:
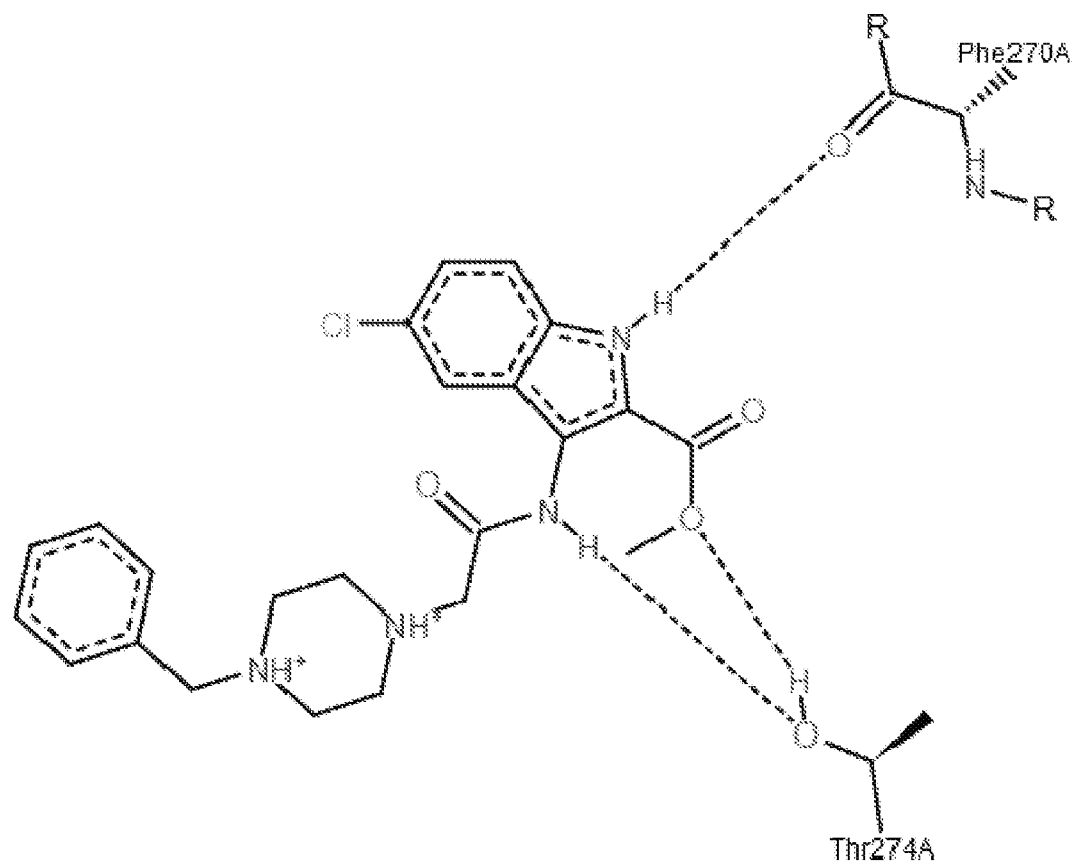

FIG. 3. The ARTS Mimetic A4 Small Molecule

Figure shows the A4 chemical structure indicating residues Phe270 and Thr274 of the BIR3/XIAP that interact with the A4 molecule.

Figure 4A:
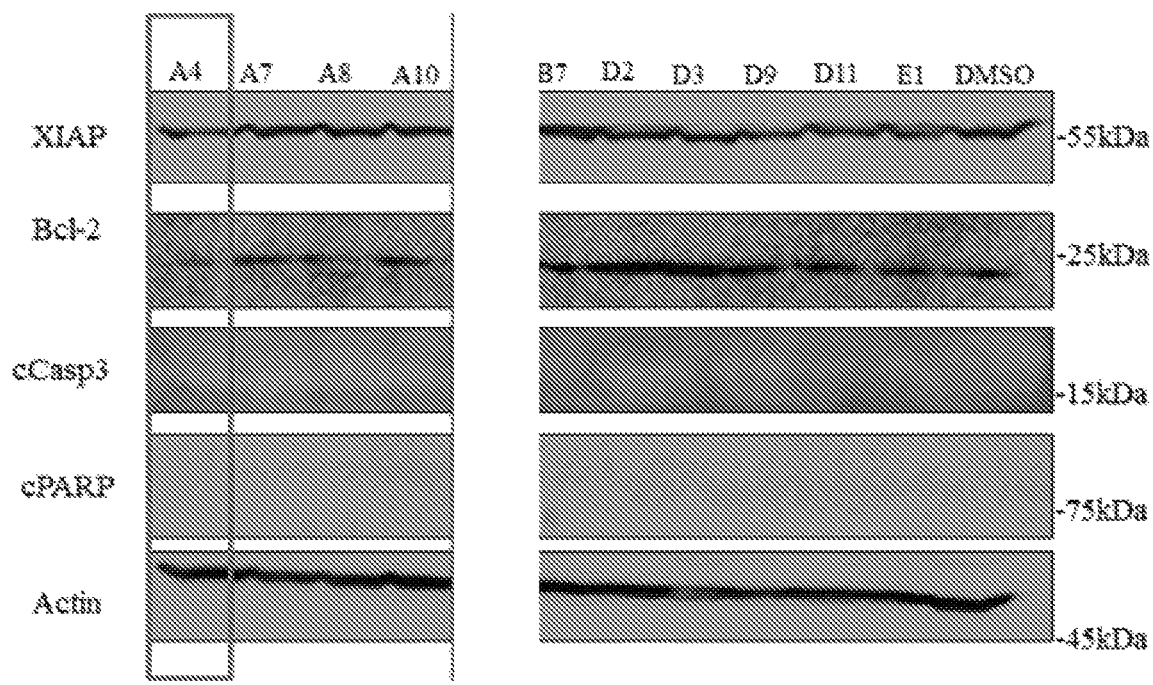
Figure 4B:
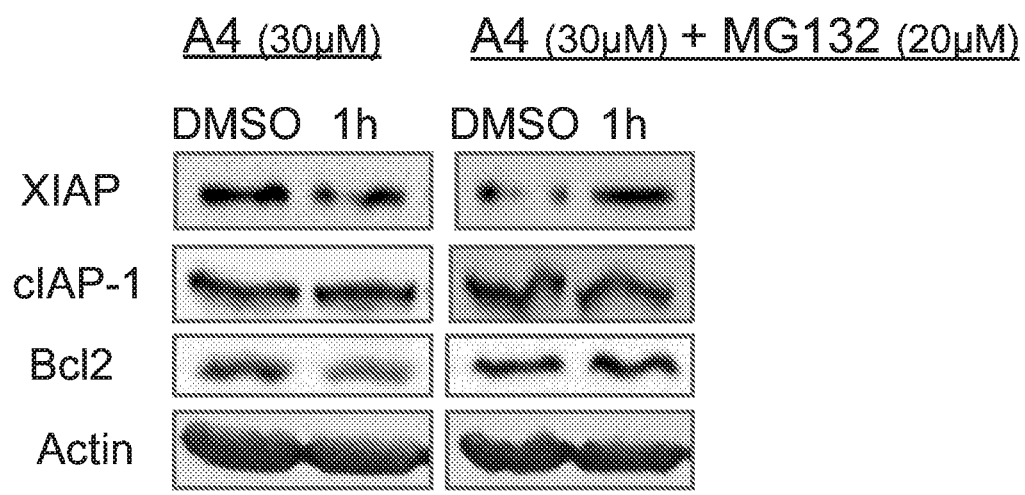
Figure 4C:
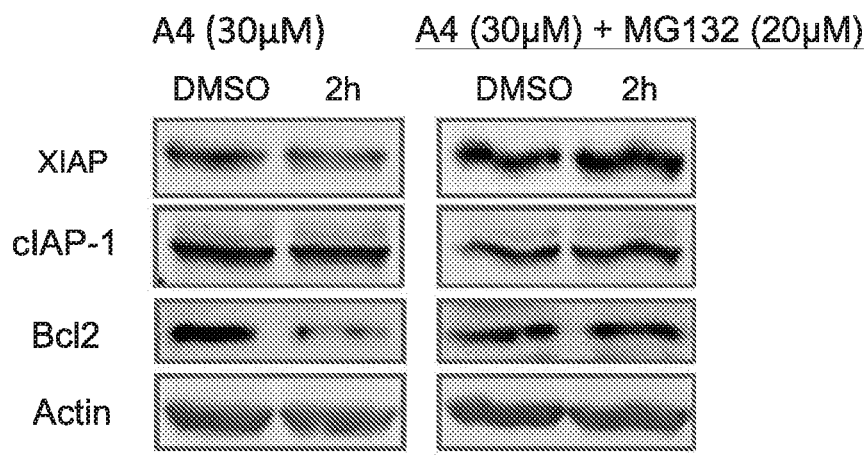
Figure 4D:
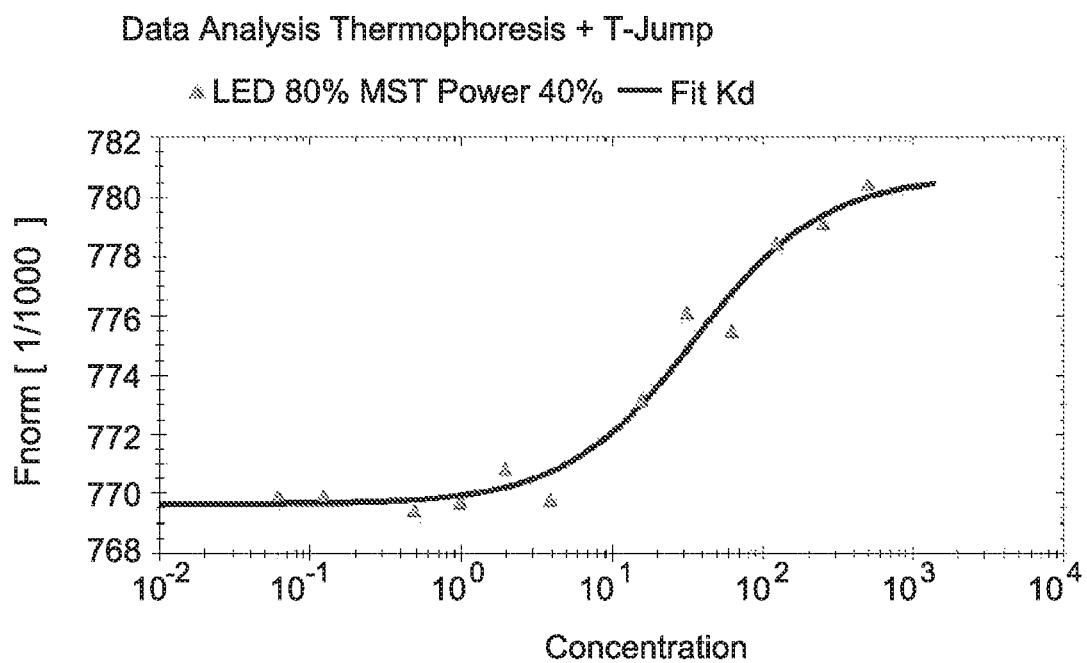

FIG. 4A-4D. XIAP and Bcl-2 Levels in A375 Human Melanoma Cells Treated with Different ARTS Mimetic Small Molecules FIG. 4A. shows the levels of XIAP and Bcl-2 in A375 cells treated with 20 uM of each of the candidate ARTS mimetic compounds for 24 hrs. SDS PAGE and Western blot analysis were performed with the indicated Abs. FIGS. 4B and 4C. show that the A4 compound promotes rapid proteasome-mediated degradation of both XIAP (but not cIAP1) and Bcl-2 in T47D breast cancer cells and in HeLa cervical cancer cells. Western blot analysis of T47D cells treated with 30 uM of A4 with and without MG132 for one hour is shown in FIG. 4B. Western blot analysis of HeLa cells treated with 30 uM of A4 with and without MG132 for two hours is shown in FIG. 4C. SDS PAGE and Western blot analysis were performed with the indicated Abs. FIG. 4D. shows MST analysis demonstrating direct binding and affinity curve between XIAP and A4.

FIG. 5A-5B. Expression of ARTS, Bcl-2 and XIAP in MCF10 Model System

FIG. 5A. Semi-quantitative PCR analysis of MCF-10 cell lines using primers recognizing the unique C' terminus of ARTS (n=3). FIG. 5B. Western blot analysis of MCF-10 cell lines for the expression of ARTS [either using an antibody recognizing the C' terminus of ARTS (ARTS C' terminus) or the N' terminus of ARTS (ARTS N' terminus), Bcl-2 and XIAP. FIGS. 5C-5F. Quantification of the expression levels of ARTS C' terminus (FIG. 5C), ARTS N' terminus (FIG. 5D), Bcl-2 (FIG. 5E) and XIAP (FIG. 5F) determined by densitometry (mean±STD, n=3). Data is normalized to actin.* denote p value≤0.05,  denote p value≤0.01 and * denote p value≤0.001.

Figure 6B:
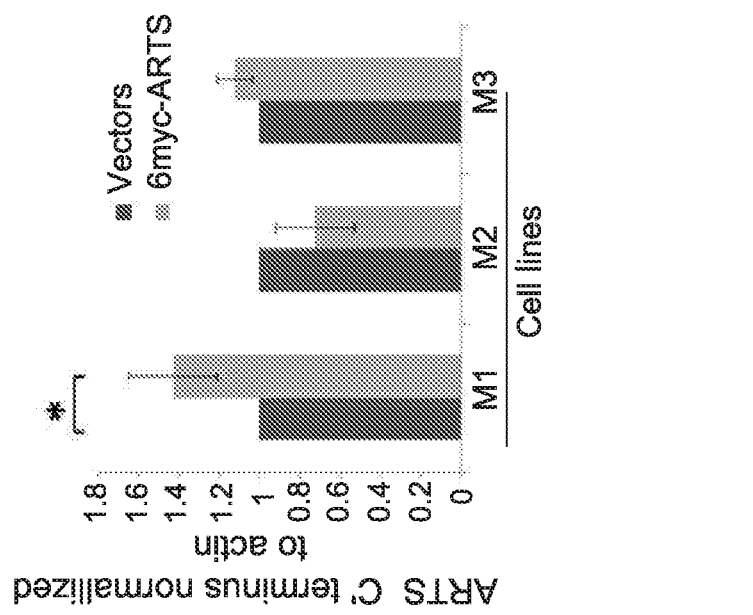
Figure 6A:
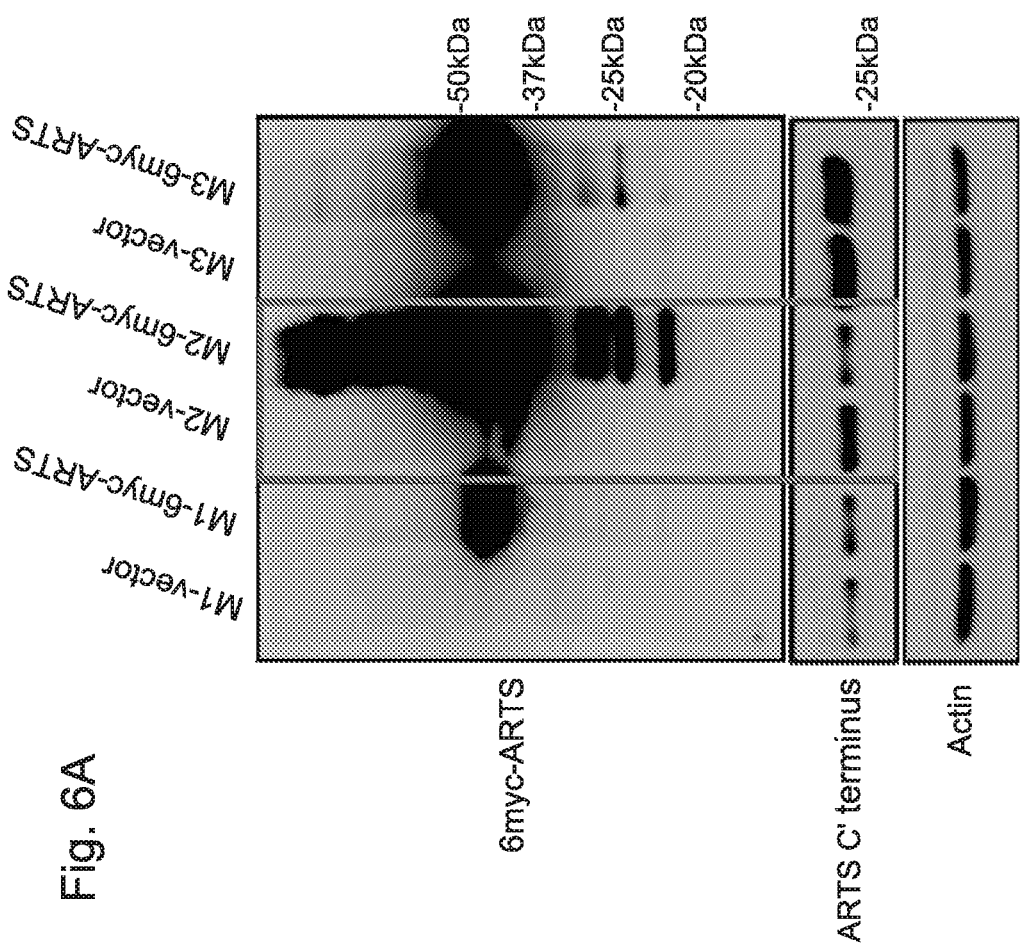

FIG. 6A-6B. Cleavage of 6myc-ARTS in Transformed Cells of MCF10 Model System

FIG. 6A-6B. MCF-10 cell lines transiently transfected either with pSC-plasmid (vector) or pSC-expressing ARTS with myc-tag at its N-terminus (6myc-ARTS). FIG. 6A. Western blot analysis showing the expression of endogenous ARTS (using antibody that recognizes the C' terminus of ARTS) and of exogenous myc-tag ARTS attached to its N-terminus (using antibody against myc). FIG. 6B. Quantification of the expression levels of endogenous ARTS as determined by densitometry (mean±STD, n=3). Data is normalized to actin. * denote p value≤0.05.

Figure 7A:
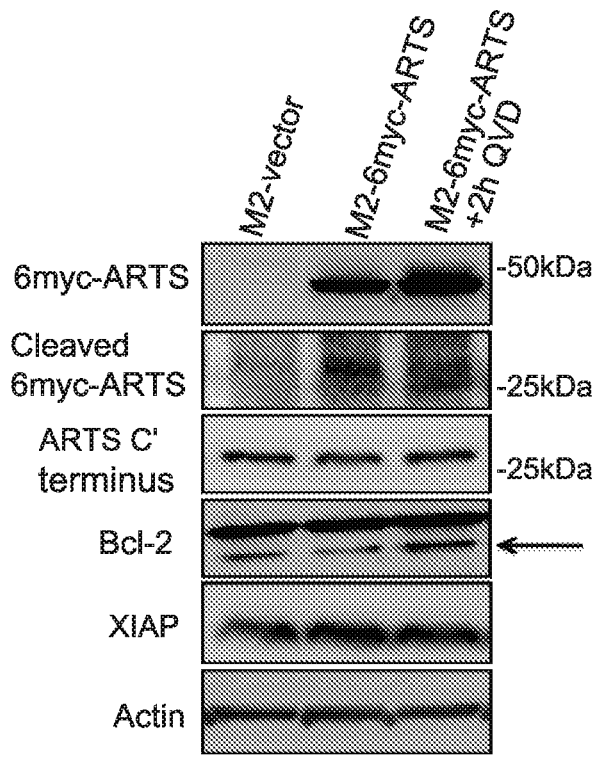
Figure 7B:
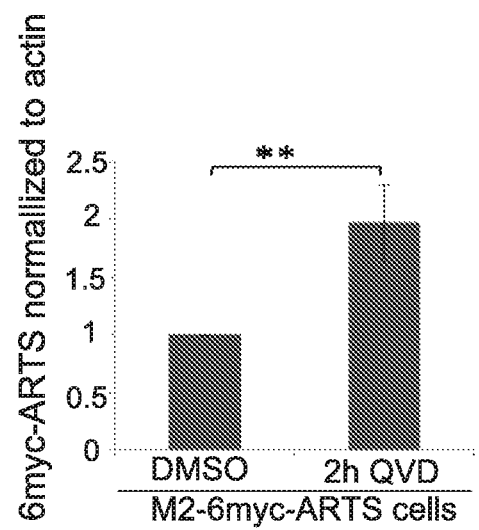
Figure 7C:
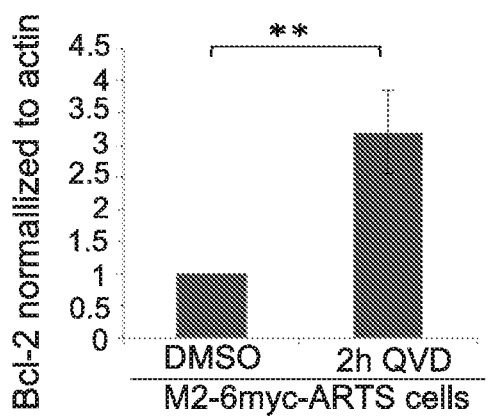
Figure 7D:
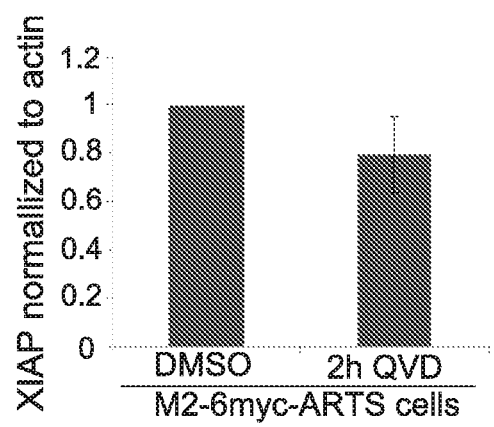

FIG. 7A-7D. Caspase Dependent Cleavage of Exogenous 6myc-ARTS Expressed in the M2 Pre-Malignant Cells FIG. 7A. Western blot analysis showing the expression of uncleaved or cleaved 6myc ARTS, endogenous ARTS, Bcl-2 (see arrow for the 25 KD form) and XIAP in M2 cells transfected with either pSC-plasmid (M2-vector) or pSC-6myc-ARTS [(6×Myc tags at the ARTS N-terminus (M2-6myc-ARTS)] treated either with vehicle (DMSO) or with pan-caspase inhibitor Q-VD. FIG. 7B-7D. Quantification of the expression levels of ARTS C'-terminus (FIG. 7B), Bcl-2 (25 kD form) (FIG. 7C) and XIAP (FIG. 7D) determined by densitometry (mean±STD, n=3). Data is normalized to actin. * denote p value≤0.05.

FIG. 8A-8C. Characterization of MCF10 cell lines cultured in the 3D BME system FIG. 8A. A scheme demonstrating breast cancer progression (adapted from Myal et. al. J Biomed Biotechnol, 2010). FIG. 8B-8C. MCF10 cell line cells were cultured in the 3D BME system for 7 days. M1 cells (normal breast cells), M2 cells (premalignant breast cells) and M3 cells (malignant breast cells). FIG. 8B. shows bright field images of MCF10 cell lines (magnification ×20). FIG. 8C. shows representative confocal images of cross sections through the middle of MCF10 cell lines organoids. Nuclei were stained with DAPI (blue). M1 develop normal acini characterized by hollow lumen surrounded by a well-polarized layer of cells, whereas the M2 cells form acini with luminal space filled with cells. M3 cells form poor-polarized organoids. Magnification ×40, Bar=50 µm.

Figure 9A:
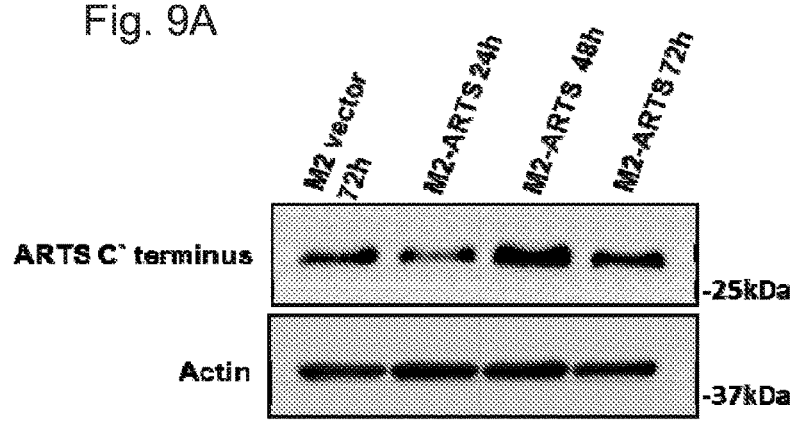
Figure 9B:
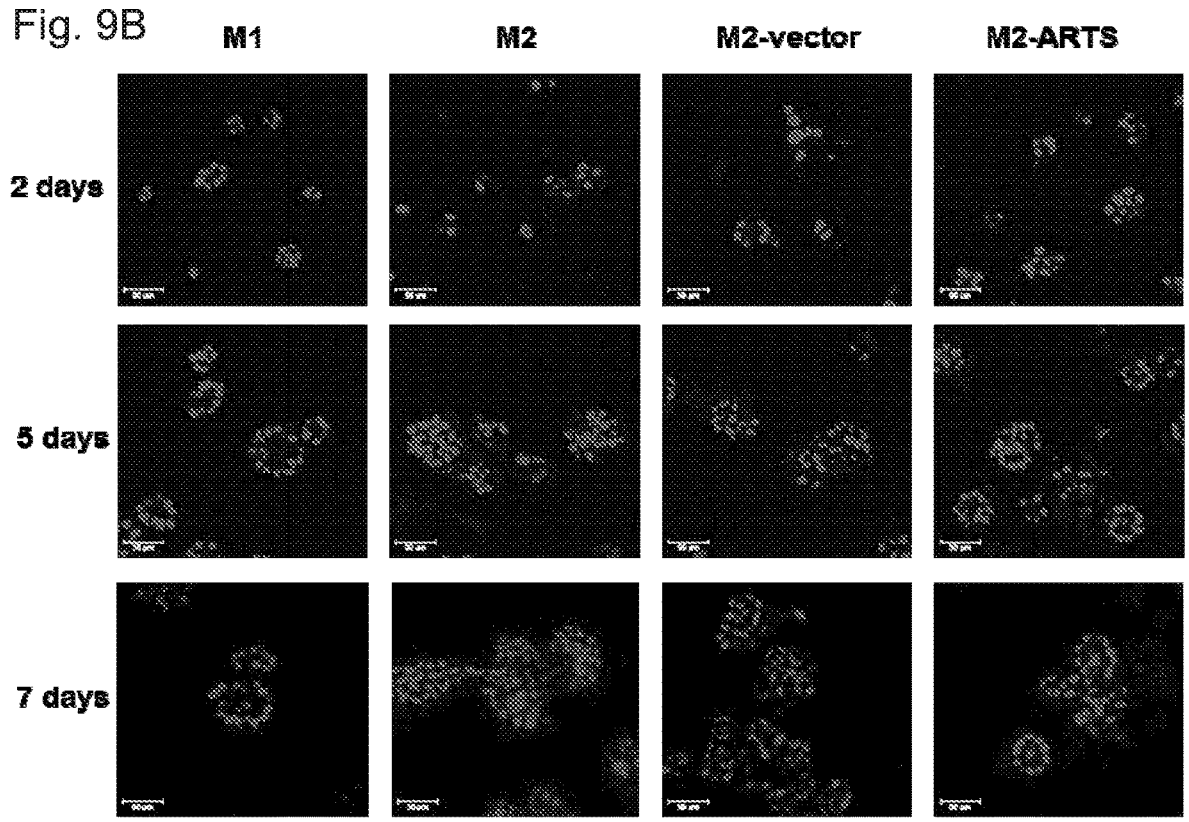

FIG. 9A-9B. Expression of Exogenous ARTS in M2 Cells Results in Reversion of the Cells to a Normal-Like Phenotype FIG. 9A. Western blot analysis for ARTS expression in M2 cells transiently transfected either with pCMV-plasmid (M2-vector) or with pCMV-sport-ARTS (M2-ARTS). FIG. 9B. M1, M2-vector and M2-ARTS cells were cultured in the 3D BME system at the indicated time points. Figure shows representative confocal images of cross-sections through the middle of M1 and M2 organoids. Nuclei stained with DAPI (blue). Magnification ×40, Bar=50 m. Notice that upon expression of ARTS in M2 cells acini is present similarly to M1 cells.

Figure 10A:
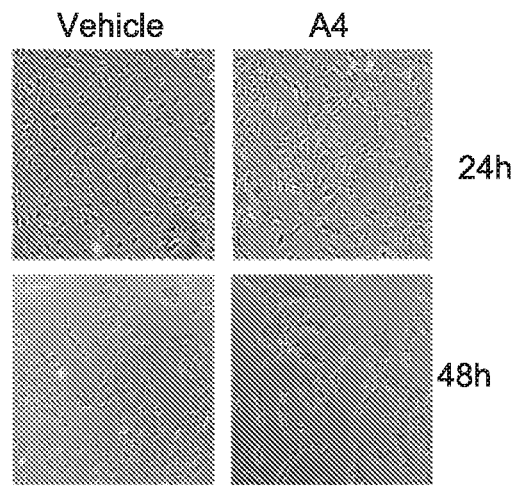
Figure 10B:
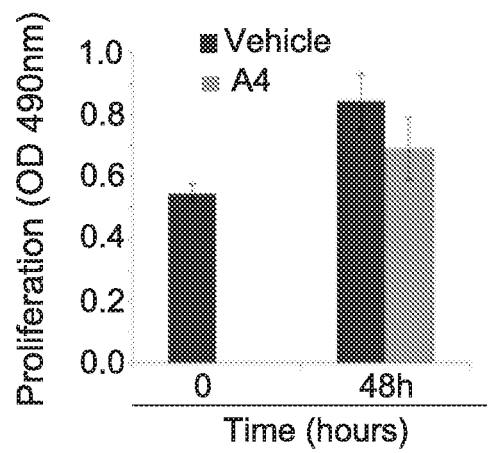

FIG. 10A-10B. The Effect of ARTS Mimetic Compound A4 on M2 Cells

M2 cells were treated either with vehicle (DMSO) or with A4.

FIG. 10A. The figure shows bright field images of M2 cells treated with A4 for 24 and 48 h (magnification ×10). FIG. 10B. The figure shows a representative experiment of the proliferation of M2 cells as described in materials and methods. mean (n=8) bars, STD.

Figure 11:
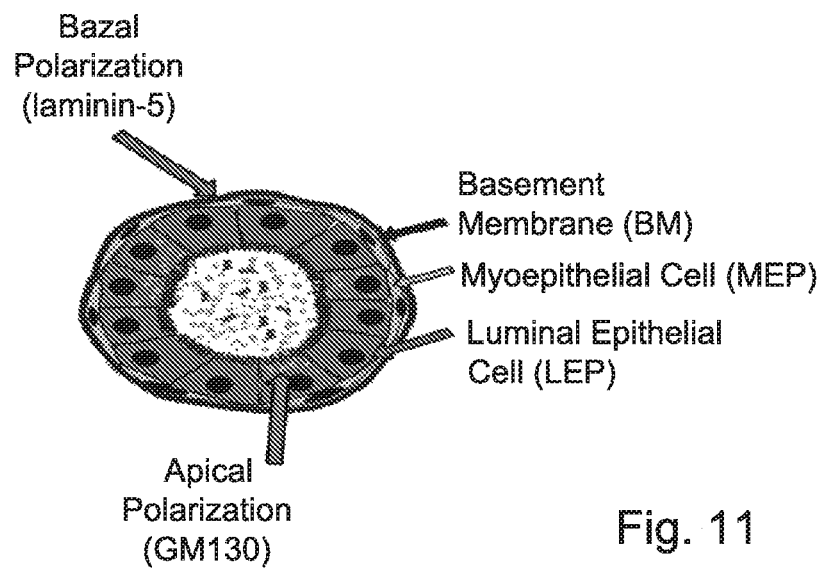

FIG. 11. Polarization of Normal Mammary Acini

Figure illustrates Basal polarization of normal acini as detected by laminin 5, which delineate the secretion of basement membrane. Apical polarization detected by the cis-Golgi protein GM130, which illustrates the apical orientation of the Golgi apparatus toward the hollow lumen of acini (adapted from Dr. Bob Avery and Debnath et al. Nature, 2005).

FIG. 12A-12B. The ARTS Mimetic Small Molecule A4 Promotes Apical Polarization of M2 Cells FIG. 12A-12B. M2 cells were cultured using the 3D BME system. M2 organoids at day 4 were either untreated or treated for additional 7 days with increasing concentrations of the A4 small molecule. A4 molecule was re-supplemented every 4 days.

FIG. 12A. shows representative light images magnification ×20. FIG. 12B. shows representative confocal images of cross-sections through the middle of organoids. F-actin stained with phalloidin (green) and the nuclei stained with DAPI (blue). Developing clusters were immunostained with antibodies to laminin-5 (red, center panel) and the cis-Golgi protein GM-130 (red, right panel). Magnification ×40. Bar=50 m.

FIG. 13A-13D. Prolonged Treatment of M2 Cells with the ARTS Mimetic Small Molecules A4 Promotes their Reversion to a Normal-Like Acini/Ductal Tree Organization FIGS. 13A-13C. M1 and M2 cells were cultured using the 3D BME system. At day 4, organoids were either untreated or treated with 40 uM A4 molecule for additional 14 days. A4 molecule was re-supplemented every 4 days.

Figures 13A, 13B:
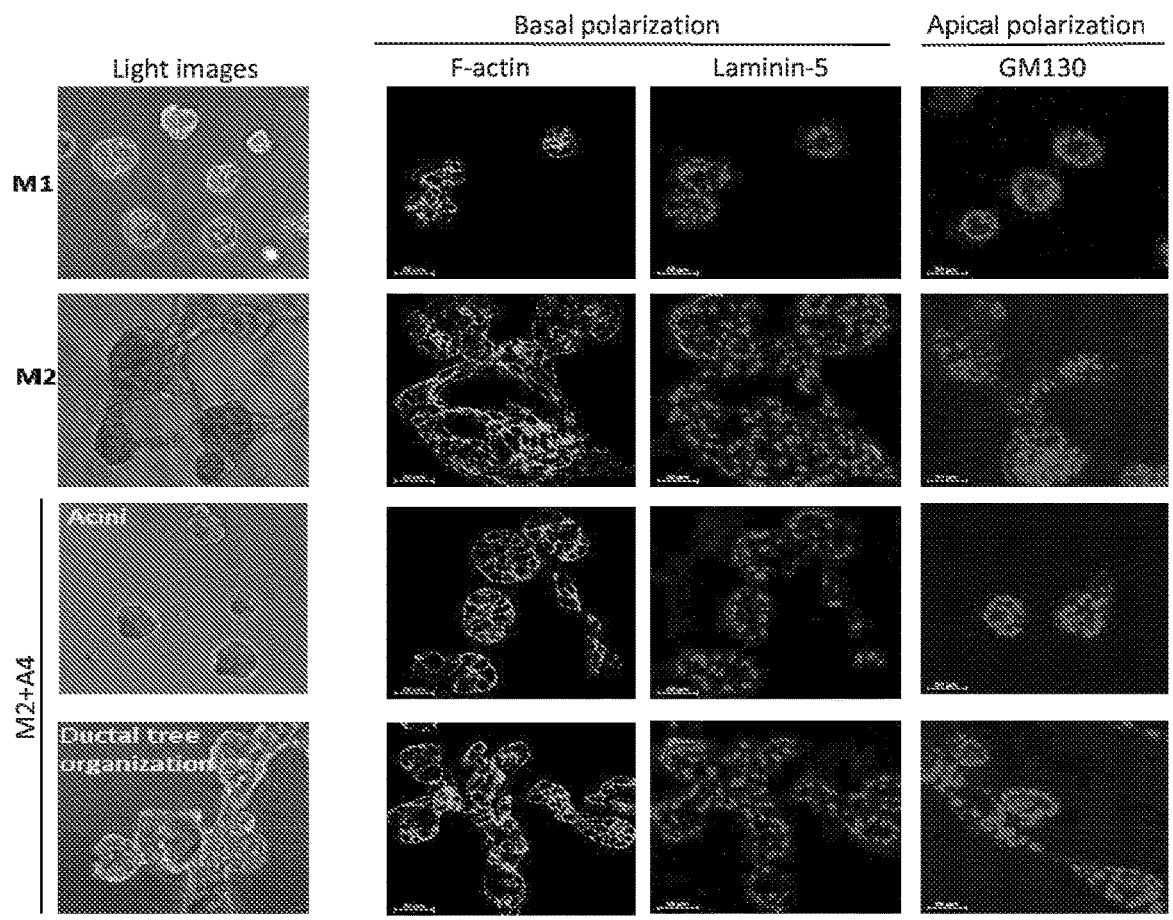

FIG. 13A. shows representative light images magnification ×20.

FIG. 13B. shows representative confocal images of cross-sections through the middle of organoids. F-actin stained with phallodin (green) and the nuclei stained with DAPI (blue).

Developing clusters were immunostained with antibodies to laminin-5 (red, center panel) and the cis-Golgi protein GM130 (red, right panel). Magnification ×40. Bar=50 µm. n=3.

Figure 13C:
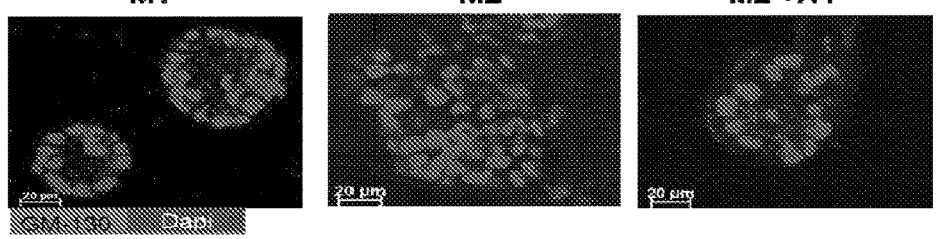

FIG. 13C. Digital zooming of confocal images acquired at magnification ×40 of M1 and M2 cells either untreated or treated with A4 molecule as described above and immunostained with antibodies to the cis-Golgi protein GM130 (red), nuclei staining (Dapi, blue) Bar=20 µm.

Figure 13D:
Figure 14:
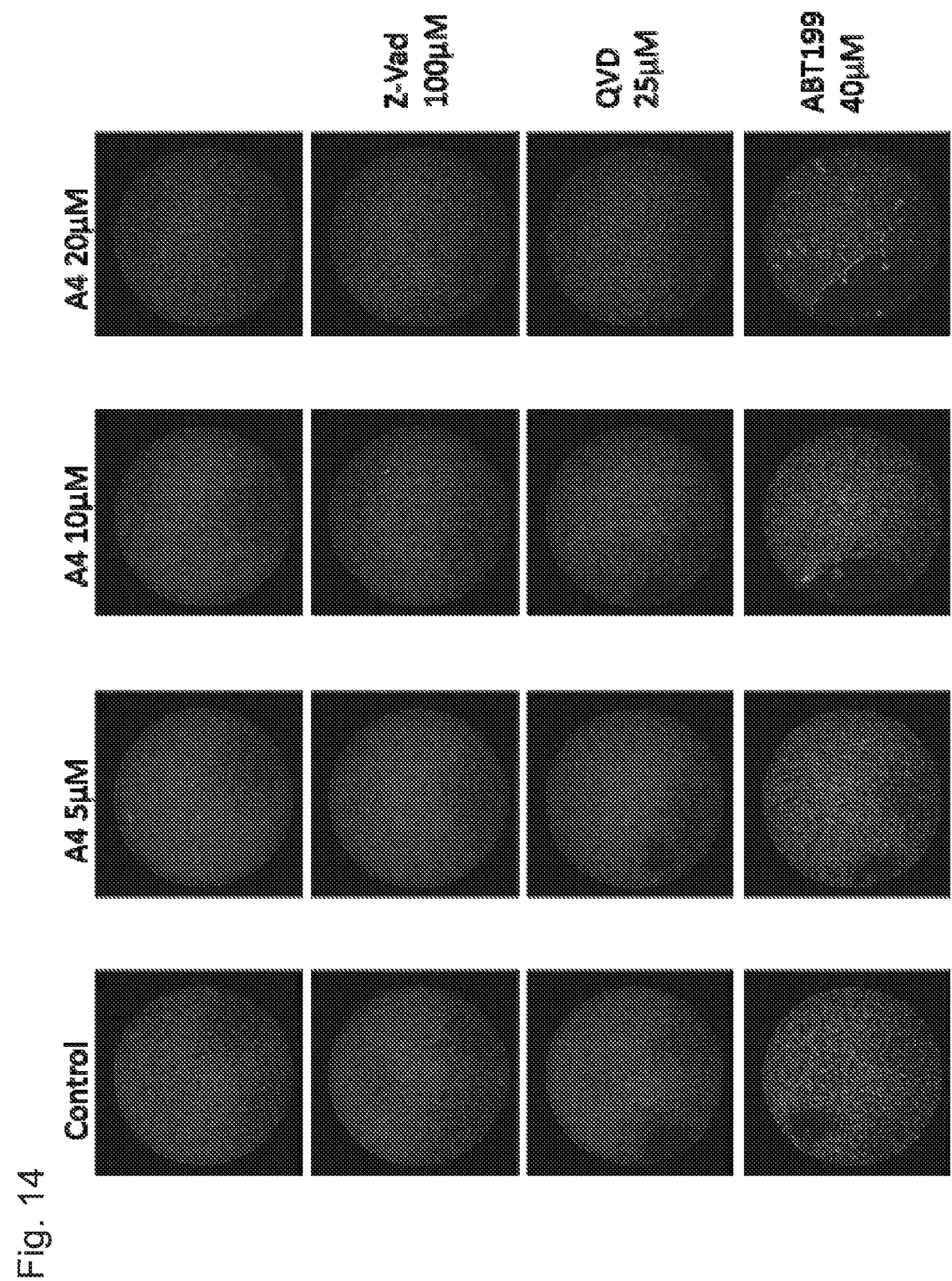

FIG. 13D. shows a schematic model of reversion of M2 cells to normal like-acini, similar to M1 cells, upon prolonged treatment with the ARTS mimetic A4 molecule FIG. 14. The ARTS Mimetic Small Molecule A4 Synergizes with BH3-Mimetic Compound 293 cells stably expressing Bcl-2 cherry reporter were treated with A4 using the indicated concentrations in the presence of the pan caspase inhibitors Z-Vad or QVD, or the BH3 mimetic compound ABT199.

DETAILED DESCRIPTION OF THE INVENTION

The apoptotic pathway is an ordered process of programmed cell death that is often altered in various pathologic conditions associated with either an increased apoptosis or with a decreased apoptosis.

Modulating apoptosis by external means provides an important and promising approach that paves the way for a variety of therapeutically opportunities. For example, cancer is a condition associated with deregulated apoptosis, resulting in cells that displaying increased survival. Thus, inducing apoptosis is valuable as a defense mechanism against hyper proliferating cells. It was shown that Bcl-2 proteins that are anti-apoptotic proteins govern the pro-survival pathway and are over expressed in a variety of tumor types such small cell lung cancer, melanoma, prostate and breast cancer.

Cancer treatment is among others aimed in restoring the apoptotic capabilities of cancer cells. Further, inhibitors of Bcl-2 and XIAP anti-apoptotic proteins are needed in order to revert to normal apoptotic processes and thus trigger tumor cell death.

Alternatively, induction of differentiation in malignant cells and thereby conversion thereof to non-malignant cells may serve as a powerful tool for treating cancerous disorders.

As indicated above, the inventors have previously found that upon induction of apoptosis, ARTS binds directly to both XIAP and Bcl-2, acting as a scaffold to bring these proteins together, leading to a UPS mediated degradation of Bcl-2.

The inventors have now developed novel ARTS mimetic compounds that target the ARTS-binding site within the XIAP BIR3 domain. These compounds act as ARTS mimetic compound mimicking ARTS unique C-terminal domain and binding thereof to distinct binding sequences in XIAP BIR3 domain.

Surprisingly, the inventors now shown that ARTS is cleaved during early stages of breast cancer progression, specifically during the transition from normal to pre-malignant breast tissue, thus impinging on its pro-apoptotic function. Whereas, introducing ARTS to the premalignant cells promotes their reversion to a normal-like breast tissue. The inventors thus have found a novel function of ARTS.

These surprising findings of the inventors are highly valuable and may lead to the development of new therapeutic strategies which target both XIAP and Bcl-2 in one hand and in the other hand induce differentiation and conversion of a malignant phenotype to a normal-like phenotype.

The inventors found that compounds having at least one amine group and at least one carbonyl group act as ARTS mimetics compounds. Specifically, the inventors found that 1,5 di-carbonyl compounds act as ARTS mimetics.

In accordance with the first aspect, the present disclosure provides 1,5-di-carbonyl compounds. In accordance with this aspect, the compounds contain one or more nitrogen atoms. In some other embodiments, the 1,5-di-carbonyl compounds contain at least one ring structure containing at least one nitrogen atom. In some further embodiments, the 1,5-di-carbonyl compounds contain a heterocyclic ring structure containing five to twelve atoms, the ring structure containing at least two carbon atoms and at least one heteroatom being N, O or S. The present disclosure also encompasses pharmaceutically acceptable salt or hydrate of the compounds described herein.

In accordance with this aspect, the present disclosure provides a compound having the general formula (I):

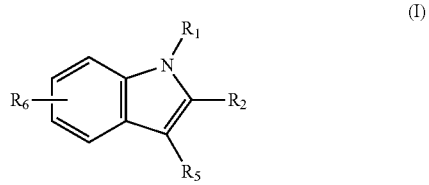

or a pharmaceutically acceptable salt, solvate, hydrate, or physiologically functional derivative thereof including any stereoisomer thereof;

wherein $R_1$ may be independently selected from H, $C_1$-$C_{12}$ alkyl, $C_2$-$C_{12}$ alkenyl, $C_2$-$C_{12}$ alkynyl;

$R_2$ may be independently selected from —C(=O)—X—$R_3$, —S(=O)—X—$R_{3'}$;

X being a heteroatom independently selected from N-containing group, O and S;

$R_3$ and $R_{3'}$, independently of each other may be selected independently from H, $C_1$-$C_{12}$ alkyl, $C_2$-$C_{12}$ alkenyl, $C_2$-$C_{12}$ alkynyl;

$R_5$ may be -L1-$R_7$-L2-$R_8$;

L1 and L2, independently of each other, may be selected independently from —(CH$_2$)$_n$—; —NH—C(=O)—(CH$_2$)$_n$—, —C(=O)—NH—(CH$_2$)$_n$—; —S—S—(CH$_2$)$_n$—; —O—(CH$_2$)$_n$—; —NH—(CH$_2$)$_n$—; C(=O)—(CH$_2$)$_n$; —S—(CH$_2$)$_n$—; —NH—S(=O)$_n$—(CH$_2$)$_n$—;

each n, being independently, may be 0 to 5;

$R_7$ may be independently selected from $C_1$-$C_{12}$ alkylene, $C_2$-$C_{12}$ alkenylene, $C_2$-$C_{12}$ alkynylene, a ring system containing five to twelve atoms, each optionally substituted;

$R_8$ may be independently selected from H, $C_1$-$C_{12}$ alkyl, $C_2$-$C_{12}$ alkenyl, $C_2$-$C_{12}$ alkynyl, a ring system containing five to twelve atoms, each optionally substituted;

$R_6$ may be independently selected from H, halogen, CN, NO$_2$, $C_1$-$C_{12}$ alkoxy, $C_1$-$C_{12}$ alkyl, $C_2$-$C_{12}$ alkenyl, $C_2$-$C_{12}$ alkynyl.

In some specific embodiments, the invention provides compounds, specifically, the compounds a defined in Formula I, acting as ARTS mimetic compounds.

In yet some further embodiments, the invention provides compounds, specifically, the compounds a defined in Formula I, for use as Bcl$_2$ antagonists.

Still further, the invention provides compounds, specifically, the compounds a defined in Formula I, for use as XIAP antagonists.

In some particular embodiments, the invention provides an effective amount of the compounds of the invention as described herein above for use in a method for treating, preventing, inhibiting, reducing, eliminating, protecting or delaying the onset of a proliferative disorder, specifically, cancer in a subject in need thereof. In yet some further embodiments, the invention provides an effective amount of the compounds as described herein for use in a method for inducing differentiation of cell/s in a subject in need thereof. In still further embodiments, the invention provides an effective amount of the compounds as described herein for use in a method for inducing apoptosis of cell/s in a subject in need thereof.

Still further, in some embodiments that further define the compounds of the invention, a ring system containing five to twelve atoms may be substituted with one or more substituents, in certain embodiments one, two, three or four substituents.

In some other embodiments, the substituents may be selected from OH, $CF_3$, halogen, C(=O), —COOH, —$NH_2$, CN, alkyl, alkenyl, alkynyl, alkylene, alkenylene, alkynylene, $C_1$-$C_{12}$ haloalkyl, $C_2$-$C_{12}$ haloalkenyl, $C_2$-$C_{12}$ haloalkynyl, $C_1$-$C_{12}$ alkoxy, $C_1$-$C_5$ carboxyl, halogen, five to twelve ring system (aromatic or heteroaromatic ring).

In some embodiments $R_1$ may be H. In some embodiments, $R_2$ may be —C(=O)—X—$R_3$.

In some embodiments, the N-containing group is selected from N, NH, $NH_2$, tertiary amine (tertiary alkyl amine), quaternary ammonium (quaternary alkyl ammonium). In some other embodiments, the N-containing group may be connected (bonded) with one $R_3$ group, at times with two $R_3$ groups, at times with three $R_3$ groups. It should be noted that in accordance with these embodiments, $R_3$ may selected independently from each other. For example, the N-containing group may be connected to three $R_3$ groups forming for example quaternary alkyl ammonium.

In some other embodiments X is O. In some further embodiments, $R_3$ and $R_{3'}$, independently of each other may be selected independently from may be H, straight or branched $C_1$-$C_{12}$ alkyl. In some further embodiments, $R_3$ may be straight $C_1$-$C_{12}$ alkyl. In yet some other embodiments, $R_3$ may be methyl, ethyl. In yet some further embodiments, $R_3$ may be methyl.

In some embodiments, L1 and L2 may be independently selected independently from each other from —NH—C(=O)—$(CH_2)_n$—, —$(CH_2)_n$—. According to these embodiments, the group —$(CH_2)_n$— wherein n=1 to 5, may encompasses an alkyl, alkylene, alkenyl, alkenylene and alkynyl as defined herein having at most five carbon atoms. In some embodiments, each of n may be independently 1 to 3. In some other embodiments when n=0, L1 and L2 may be a bond. In some embodiments, L1 is —NH—C(=O)—$(CH_2)_n$—. In some further embodiments, n is 1. In some other embodiments, L1 is —NH—C(=O)—$(CH_2)$—. In some embodiments, L2 is —$(CH_2)_n$—. In some further embodiments, n is 1. In some other embodiments, L2 is —$(CH_2)$—.

In some embodiments, $R_7$ may be a ring system containing five to twelve atoms, optionally substituted. In some other embodiments, the ring system of $R_7$ may be an aryl (aromatic ring) or aliphatic ring (non-aromatic ring). In some further embodiments, $R_7$ may be $C_5$-$C_{12}$ saturated cycloalkyl, $C_5$-$C_{12}$ saturated cycloalkylene, $C_5$-$C_{12}$ aryl or $C_5$-$C_{12}$ arylene. In some further embodiments, the ring system of $R_7$ may contain at least two carbon atoms and may include at least one heteroatom ring. In some further embodiments, $R_7$ may be heteroaryl, heteroarylene, heterocycloalkylene or heterocycloalkyl. In some further embodiments, $R_7$ may be $C_2$-$C_{12}$ heterocycloalkyl ring, $C_2$-$C_{12}$ heteroaryl or $C_2$-$C_{12}$ heteroarylene. In some embodiments, the heteroatom may be N, O, S. In yet some further embodiments, the heteroatom may be N, O. In some other embodiments, the heteroatom may be N. In some other embodiments, $R_7$ is piperidine. In some other embodiments, $R_7$ is piperazine.

In some other embodiments, $R_8$ may be H, straight or branched $C_1$-$C_{12}$ alkyl or five to twelve atom ring system. In some further embodiments, $R_8$ may be straight or branched $C_1$-$C_{12}$ alkyl or five to twelve atom ring system each optionally substituted. In yet further embodiments, $R_8$ may be $C_1$-$C_5$ alkyl. In some further embodiments, $R_8$ may be straight $C_1$-$C_5$ alkyl substituted with OH. In some other embodiments, $R_8$ may be an aromatic ring, non-aromatic ring (aliphatic ring). In some further embodiments, $R_8$ may be $C_5$-$C_{12}$ saturated cycloalkyl, $C_5$-$C_{12}$ saturated cycloalkylene, $C_5$-$C_{12}$ aryl or $C_5$-$C_{12}$ arylene. In some further embodiments, the ring system of $R_8$ may contain at least two carbon atoms and may include at least one heteroatom ring. In some further embodiments, $R_8$ may be heteroarylene, heteroaryl, heterocycloalkylene or heterocycloalkyl. In some further embodiments, $R_8$ may be $C_2$-$C_{12}$ heterocycloalkyl ring or $C_2$-$C_{12}$ heterocyclic aromatic ring (aryl or arylene). In some embodiments, the heteroatom may be N, O, S In yet some further embodiments, $R_8$ is an aromatic ring containing six atoms. In some other embodiments, $R_8$ may be an aromatic ring. In some other embodiments, $R_8$ is phenyl.

In some embodiments, $R_6$ may be connected (bonded, attached) to any position of the ring. In some further embodiments, the ring may be substituted with one $R_6$, at time with two $R_6$, at times with three $R_6$, at times with four $R_6$. In some embodiments, $R_6$ may be independently selected from the group consisting of H, halogen, CN, $NO_2$. In some other embodiments, $R_6$ may be independently selected from H, halogen. In some other embodiments, $R_6$ may be H. In some further embodiments, $R_6$ may be Cl. In some other embodiments, $R_6$ may be an electron withdrawing group.

In some embodiments with this aspect, a compound of the invention has the general formula (II) including any stereoisomer or salt thereof:

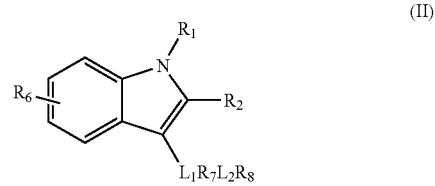

(II)

In some embodiments a compound of the invention has the general formula (III) including any stereoisomer or salt thereof:

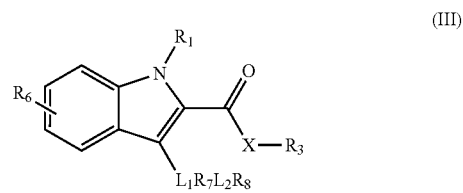

(III)

In some embodiments a compound of the invention has the general formula (IV) including any stereoisomer or salt thereof:

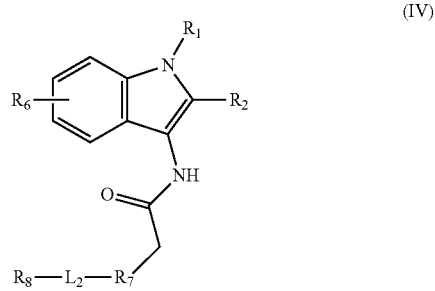

(IV)

In some embodiments a compound of the invention has the general formula (V) including any stereoisomer or salt thereof:

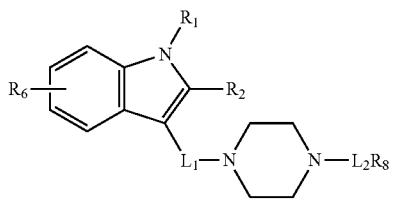
(V)

In some embodiments a compound of the invention has the general formula (VI) including any stereoisomer or salt thereof:

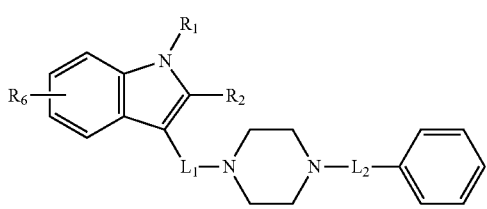
(VI)

In some embodiments a compound of the invention has the general formula (VII) including any stereoisomer or salt thereof:

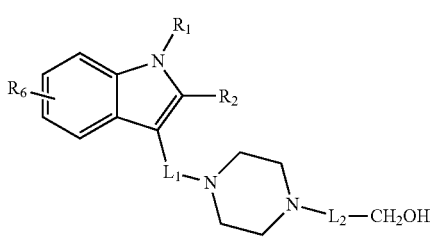
(VII)

In some further embodiments, a compound of the invention having Formula I, Formula II or Formula III is characterized by $R_1$ is H, $R_2$ is —C(=O)—X—$R_3$, L1 is NH—C(=O)—(CH$_2$)—, L2 is —(CH$_2$)—, $R_7$ is piperazine, $R_8$ is phenyl, $R_6$ is Cl, X is O and $R_3$ is methyl. In some further embodiments, a compound of the invention having Formula IV, is characterized by $R_1$ is H, $R_2$ is —C(=O)—X—$R_3$, L2 is —(CH$_2$)—, $R_6$ is Cl, $R_7$ is piperazine, $R_8$ is phenyl, X is O and $R_3$ is methyl. In some further embodiments, a compound of the invention having Formula V, is characterized by $R_1$ is H, $R_2$ is —C(=O)—X—$R_3$, L1 is NH—C(=O)—(CH$_2$)—, L2 is —(CH$_2$)—, $R_8$ is phenyl, $R_6$ is Cl, X is O and $R_3$ is methyl. In some further embodiments, a compound of the invention having Formula VI, is characterized by $R_1$ is H, $R_2$ is —C(=O)—X—$R_3$, L1 is NH—C(=O)—(CH$_2$)—, L2 is —(CH$_2$)—, $R_6$ is Cl, X is O and $R_3$ is methyl. In some further embodiments, a compound of the invention having Formula VII, is characterized by $R_1$ is H, $R_2$ is —C(=O)—X—$R_3$, L1 is NH—C(=O)—(CH$_2$)—, L2 is —(CH$_2$)—, $R_6$ is Cl, X is O and $R_3$ is methyl.

In some embodiments, specific examples of compounds or pharmaceutically acceptable salts or hydrates or any stereoisomer thereof of the compounds of Formula I-VII include, without limitation:

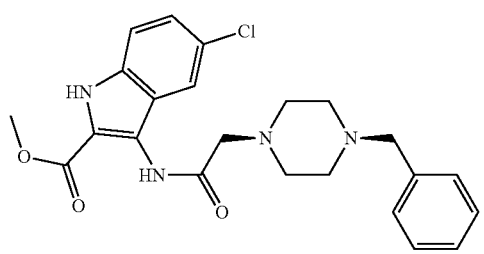
(a)

3-[2-(4-Benzyl-piperazin-1-yl)-acetylamino]-5-chloro-1H-indole-2-carboxylic acid methyl ester)

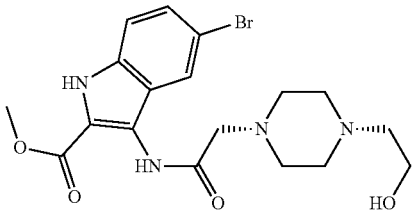
(b)

5-Bromo-3-{2-[4-(2-hydroxy-ethyl)-piperazin-1-yl]-acetylamino}-1H-indole-2-carboxylic acid methyl ester

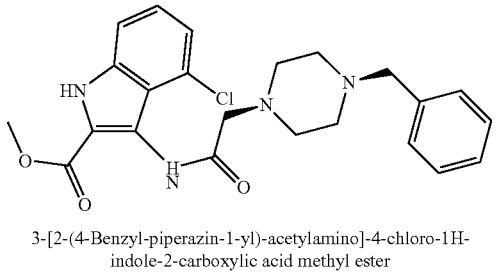
(c)

3-[2-(4-Benzyl-piperazin-1-yl)-acetylamino]-4-chloro-1H-indole-2-carboxylic acid methyl ester

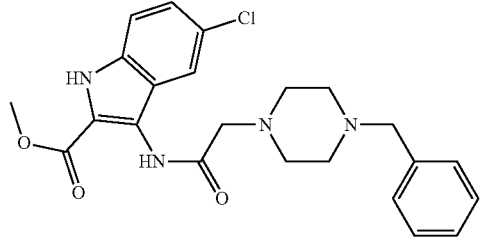
(d)

3-[2-(4-Benzyl-piperazin-1-yl)-acetylamino]-5-chloro-1H-indole-2-carboxylic acid methyl ester)

In accordance with the second aspect, the present disclosure provides 1,5-di-carbonyl compounds. In accordance with this aspect, the compounds contain one or more nitrogen atoms. In some other embodiments, the compounds contain at least one ring structure. In some other embodiments, the ring structure containing at least one nitrogen atom. In some further embodiments, the 1 compounds contain a heterocyclic ring structure containing five to twelve atoms, the ring structure containing at least two carbon atoms and at least one heteroatom being N, O or S.

The present disclosure provides in accordance with the second aspect, a compound having the general formula (VIII):

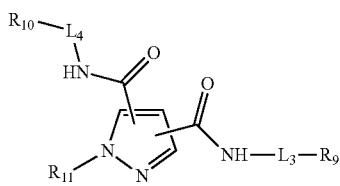

(VIII)

or a pharmaceutically acceptable salt or hydrate thereof including any stereoisomer thereof; wherein:

$R_9$ and $R_{10}$ may be the same or may be different and may be independently selected from each other from a ring system containing five to twelve atoms, each optionally substituted;

$R_{11}$ may be independently selected from H, straight or branched $C_1$-$C_{12}$ alkyl, straight or branched $C_2$-$C_{12}$ alkenyl, straight or branched $C_2$-$C_{12}$alkynyl;

L3 and L4, independently of each other, may be selected independently from —(CH$_2$)$_p$—; —NH—C(=O)—(CH$_2$)$_p$—, —C(=O)—NH—(CH$_2$)$_p$—; —S—S—(CH$_2$)$_p$—; —O—(CH$_2$)$_p$—; —NH—(CH$_2$)$_p$—; C(=O)—(CH$_2$)$_p$; —S—(CH$_2$)$_p$—; —NH—S(=O)$_p$—(CH$_2$)$_p$—;

each p, being independently, may be 0 to 5.

In some embodiments, a ring system containing five to twelve atoms may be substituted with one or more substituents, in certain embodiments one, two, three or four substituents, In some further embodiments, the substituents may be selected from OH, CF$_3$, halogen, C(=O), —COOH, —NH$_2$, CN, C(=O)-alkyl, alkyl, alkenyl, alkynyl, alkylene, alkenylene, alkynylene, $C_1$-$C_{12}$ alkoxy, $C_1$-$C_5$ carboxyl, halogen, aromatic or heteroaromatic ring.

In some embodiments, $R_9$ and $R_{10}$ may be a ring system containing five to twelve atoms. In some further embodiments, the ring system of $R_9$ and $R_{10}$ may contain at least two carbon atoms. In some other embodiments, the ring system of $R_9$ and $R_{10}$ may be an aromatic ring, non-aromatic ring, fused ring or the like. In some further embodiments, $R_9$ and $R_{10}$ may be $C_5$-$C_{12}$ saturated cycloalkyl, $C_5$-$C_{12}$ saturated cycloalkylene, $C_5$-$C_{12}$ aryl or $C_5$-$C_{12}$ arylene. In some other embodiments, the ring system of $R_9$ and $R_{10}$ may include at least one heteroatom ring. In some further embodiments, $R_9$ and $R_{10}$ may be heteroaryl or heterocycloalkyl. In some further embodiments, $R_9$ and $R_{10}$ may be $C_2$-$C_{12}$ hetero cycloalkyl or $C_2$-$C_{12}$ hetero aromatic ring (aryl or arylene). It should be noted that according with some embodiments, $R_9$ and $R_{10}$ may be independently from each other contain different carbon atoms. In some embodiments, the heteroatom may be N, O, S. In some embodiments, $R_9$ and $R_{10}$ may be independently from each other selected from $C_5$-$C_{12}$ aryl. In some embodiments, $R_9$ and $R_{10}$ may be $C_6$ aryl, optionally substituted. In some embodiments, $R_9$ and $R_{10}$ may be $C_6$ aryl optionally substituted with —C(=O)-alkyl. In some further embodiments, $R_9$ and $R_{10}$ may be $C_6$ aryl optionally substituted with —C(=O)—CH$_3$ In some embodiments, L3 and L4, may be —(CH$_2$)$_p$—. According to these embodiments, the group —(CH$_2$)$_p$— wherein p=1 to 5, may encompasses an alkyl, alkylene, alkenyl, alkenylene and alkynyl as defined herein having at most five carbon atoms. In some embodiments, each of p may be 0. At times, when p=0, L3 and L4 are a bond.

In some embodiments, $R_{11}$ is H or straight $C_1$-$C_{12}$ alkyl. In some further embodiments, $R_{11}$ is straight $C_1$-$C_{12}$ alkyl. In some other embodiments, $R_{11}$ is methyl.

In some embodiments, $R_9$ and $R_{10}$ may be $C_6$ aryl optionally substituted with —C(=O)—CH$_3$.

In some embodiments, L3 and L4 are a bond. In some embodiments, $R_{11}$ is methyl, $R_9$ and $R_{10}$ are $C_6$ aryl substituted with —C(=O)—CH$_3$ and L3 and L4 are a bond.

In some embodiments, specific examples of compounds or pharmaceutically acceptable salts or hydrates including any stereoisomer thereof of the compounds of Formula VIII include, without limitation:

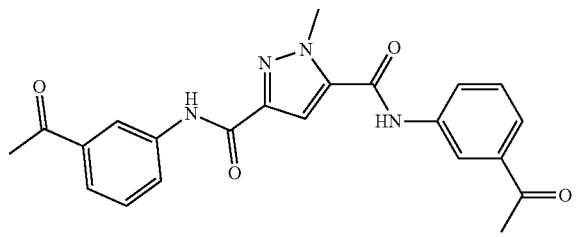

1-Methyl-1H-pyrazole-3,5-dicarboxylic acid bis-[(3-acetyl-phenyl)-amide]

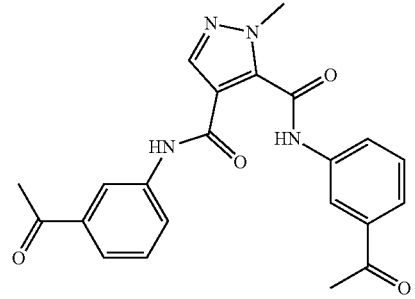

2-Methyl-2H-pyrazole-3,4-dicarboxylic acid bis-[(3-acetyl-phenyl)-amide]

In accordance with the third aspect, the present disclosure provides compounds containing one or more nitrogen atoms. In some other embodiments, the compounds contain at least one ring structure. In some other embodiments, the ring structure containing at least one nitrogen atom. In some further embodiments, the compounds contain a heterocyclic ring structure containing five to twelve atoms, the ring structure containing at least two carbon atoms and at least one heteroatom being N, O or S. in some other embodiments, the compounds contain an amide group.

In accordance with the third aspect, the present disclosure provides a compound having a general formula:

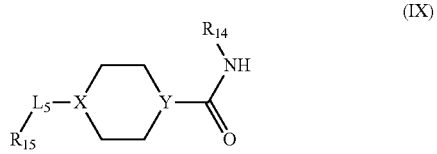

(IX)

or a pharmaceutically acceptable salt or hydrate thereof including any stereoisomer thereof;

wherein:

X, Y independently may be each independently selected from each other from NH, CH;

$R_{14}$ and $R_{15}$ may be the same or may be different and may be independently from each other selected from a ring system containing five to twelve atoms, each optionally substituted;

L5 may be selected independently from —(CH$_2$)$_q$—; —NH—C(=O)—(CH$_2$)$_q$—, —C(=O)—NH —(CH$_2$)$_q$—; —S—S—(CH$_2$)$_q$—; —O—(CH$_2$)$_q$—; —NH—(CH$_2$)$_q$—; C(=O)—(CH$_2$)$_q$—; —S —(CH$_2$)$_q$—; —NH—S(=O)$_q$—(CH$_2$)$_q$—;

each q, being independently, may be 0 to 5;

In some embodiments, R$_{14}$ and R$_{15}$ may be a ring system containing five to twelve atoms. In some further embodiments, the ring system of R$_{14}$ and R$_{15}$ may contain at least two carbon atoms. In some other embodiments, the ring system of R$_{14}$ and R$_{15}$ may be an aromatic ring or a non-aromatic ring. In some further embodiments, R$_{14}$ and R$_{15}$ may be C$_5$-C$_{12}$ saturated cycloalkyl, C$_5$-C$_{12}$ saturated cycloalkylene, C$_5$-C$_{12}$ aryl or C$_5$-C$_{12}$ arylene. In some other embodiments, the ring system of R$_{14}$ and R$_{15}$ may include at least one heteroatom ring. In some further embodiments, R$_{14}$ and R$_{15}$ may be C$_2$-C$_{12}$ hetero cycloalkyl or C$_2$-C$_{12}$ hetero aromatic ring. It should be noted that according with some embodiments, R$_{14}$ and R$_{15}$ may be independently from each other contain different carbon atoms. In some embodiments, the heteroatom may be N, O, S. In some embodiments, R$_{14}$ and R$_{15}$ may be independently from each other selected from C$_5$-C$_{12}$ aryl optionally substituted. In some embodiments, R$_{14}$ and R$_{15}$ may be independently from each other selected from isoquinoline or phyel each independently from the other optionally substituted. In some embodiments, L5, may be —(CH$_2$)$_q$—. According to these embodiments, the group —(CH$_2$)$_q$— wherein q=0 to 5, may encompasses an alkyl, alkenyl and alkynyl as defined herein having at most five carbon atoms. In some embodiments, each of q may be 0. At times, when q=0, L5 may be a bond.

In some embodiments, a ring system containing five to twelve atoms may be substituted with one or more substituents, in certain embodiments one, two, three or four substituents. In some further embodiments, the substituents may be selected from OH, CF$_3$, halogen, NO$_2$, C(=O), —COOH, —NH$_2$, CN, C(=O)—C$_1$-C$_{12}$ alkyl, straight or branched C$_1$-C$_{12}$ alkyl, straight or branched C$_2$-C$_{12}$ alkenyl, straight or branched C$_2$-C$_{12}$ alkynyl, straight or branched C$_1$-C$_{12}$ alkylene, straight or branched C$_2$-C$_{12}$ alkenylene, straight or branched C$_2$-C$_{12}$ alkynylene, C$_1$-C$_{12}$ alkoxy, C$_1$-C$_5$ carboxyl, aromatic or heteroaromatic ring.

In some embodiments, specific examples of compounds or pharmaceutically acceptable salts or hydrates including any stereoisomer thereof of the compounds of Formula IX include, without limitation:

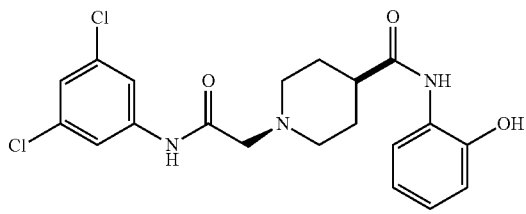

1-[(3,5-Dichloro-phenylcarbamoyl)-methyl]-piperidine-4-carboxylic acid (2-hydroxy-phenyl)-amide -continued

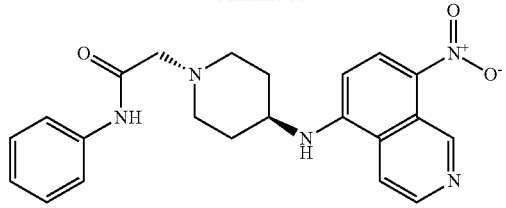

2-[4-(8-Nitro-isoquinolin-5-ylamino)-piperazin-1-yl]-N-phenyl-acetamide

It should be appreciated that in some aspects, the invention provides the compounds of any one of the compounds of Formulas I, II, III, IV, V, VI, VII, as well as the compounds of formulas VIII, IX as described herein and any analogs or derivative thereof including any stereoisomer or salt thereof or any vehicle, matrix, nano- or micro-particle, or composition comprising the same.

In some particular aspects, the invention provides an effective amount of the compounds of the invention, specifically, any one of the compounds of Formulas I, II, III, IV, V, VI, VII, as well as the compounds of formulas VIII, IX as described herein and any analogs or derivative thereof including any stereoisomer or salt thereof or any vehicle, matrix, nano- or micro-particle, or composition comprising the same as described herein above for use in a method for treating, preventing, inhibiting, reducing, eliminating, protecting or delaying the onset of a proliferative disorder, specifically, cancer, in a subject in need thereof. In yet some further embodiments, the invention provides an effective amount of the compounds as described herein for use in a method for inducing differentiation and/or apoptosis of cell/s in a subject in need thereof.

Still further, the term "alkyl" as used herein refers to a linear, branched saturated hydrocarbon having from 1 to 20 carbon atoms. The term "C$_1$-C$_{12}$ alkyl" or "C$_1$-C$_{12}$ alkylene" refers to a linear (straight), branched saturated hydrocarbon having from 1 to 12 carbon atoms, in some embodiments, contain from 2 to 8 carbons, in yet some embodiments from 2 to 5 carbons, in yet some further embodiments, from 1 to 3 carbon atoms. It should be noted that alkyl refers to an alkyl end chain and alkylene refers to a middle chain alkyl. Representative C$_1$-C$_{12}$ alkyl groups include, but are not limited to, methyl, ethyl, propyl, isopropyl, cyclopropyl, butyl, sec-butyl, iso-butyl, tert-butyl, cyclobutyl, pentyl, iso-pentyl, neo-pentyl, tert-pentyl, cyclopentyl, hexyl, cyclohexyl, heptyl, cycloheptyl, octyl, sec-octyl (1-methylheptyl), and cyclooctyl.

The term "C$_1$-C$_{12}$ haloalkyl" as used herein refers to a C$_1$-C$_{12}$ alkyl as defined above, with one or more hydrogens substituted by halogen atoms.

The term "alkenyl" as used herein refers to a linear (straight), branched unsaturated hydrocarbon having from 2 to 20 carbon atoms and at least one carbon-carbon double bond. The term "C$_2$-C$_{12}$ alkenyl" or "C$_2$-C$_{12}$ alkenylene" as used herein refers to a linear, branched unsaturated hydrocarbon having from 2 to 12 carbon atoms and at least one carbon-carbon double bond, in some embodiments from 3 to 8 carbons, in yet some further embodiments, from 3 to 5 carbon atoms and at least one double bond. It should be noted that alkenyl refers to an alkyl end chain and alkenylene refers to a middle chain alkyl.

The term "C$_2$-C$_{12}$ haloalkenyl" as used herein refers to a C$_2$-C$_{12}$ alkenyl as defined above, with one or more hydrogens substituted by halogen atoms.

The term "alkynyl" as used herein refers to a linear, branched unsaturated hydrocarbon having from 2 to 20 carbon atoms and at least one carbon-carbon triple bond. The term "$C_2$-$C_{12}$ alkynyl" or "$C_2$-$C_{12}$ alkynylene" as used herein refers to a linear, branched unsaturated hydrocarbon having from 2 to 12 carbon atoms in certain embodiments, from 3 to 8 carbons, and at least one triple bond (at least one carbon-carbon triple bond). It should be noted that alkynyl refers to an alkyl end chain and alkynylene refers to a middle chain alkyl.

The term "$C_2$-$C_{12}$ haloalkynyl" as used herein refers to a $C_2$-$C_{12}$ alkynyl as defined above, with one or more hydrogens substituted by halogen atoms.

As used herein "alkoxy" refers to an alkyl group bonded to an oxygen atom. Similarly, the term "$C_1$-$C_{12}$ alkoxyl" as used herein refers to a $C_1$-$C_{12}$ alkyl group linked to an oxygen. At times, the alkyl group may include one to twelve carbon atoms, at times between one to eight carbon atoms, at times one to five carbon atoms and at times one to three carbon atoms. Representative examples are methoxy, ethoxy, n-propoxy, isopropoxy, butoxy, sec-butoxy, tert-butoxy, pentoxy, isopentoxy, hexoxy, isohexoxy and the like. In certain embodiments, the alkoxy is ethoxy.

The term "halogen" (halo or halide) refers to F, Cl, Br or I.

As used herein, a ring system containing five to twelve atoms refers to a mono- or multi-cyclic ring system having 5 to 12 atoms. The ring system containing five to twelve atoms may be saturated, unsaturated or aromatic rings and the like including for example cycloalkyl, heterocycloalkyl, aryl, arylene, aromatic, heteroaromatic rings. A ring system containing five to twelve atoms may contain two rings (bicyclic, etc.), for example aromatic rings and in such case the aromatic rings of the aryl group may be joined at a single point (e.g., biphenyl), or fused (e.g., naphthyl). In some embodiments, a ring system containing five to twelve atoms is a carbocyclic ring or heterocyclic ring. The term "carbocyclic ring" refers to cyclic compounds containing only carbon atoms. The carbocyclic ring may be optionally substituted by one or more substituents, and may be saturated, unsaturated or aromatic. The term "heterocyclic ring" refers to cyclic compounds where one or more carbons are substituted by heteroatoms.

Exemplary heteroatoms include, but not limited to, nitrogen, sulfur, and oxygen. The heterocyclic ring may be optionally substituted, and may be saturated, unsaturated or aromatic.

The term "saturated" as used herein means that the compound does not contain double or triple bonds. The term "unsaturated" as used herein means that the compound contains at least one double or triple bond. The term "aromatic" as used herein means that the compound contains alternating double and single bonds.

As used herein, "aryl" refers to aromatic ring systems having between 5 to 12 atoms. Unless otherwise specifically defined, the term "aryl" refers to cyclic, aromatic hydrocarbon groups that have 1 to 2 aromatic rings, including monocyclic or bicyclic groups having between 5 to 12 atoms. Non-limiting examples include phenyl, biphenyl or naphthyl. The aryl group may be optionally substituted by one or more substituents, e.g., 1 to 5 substituents, at any point of attachment. The substituents can themselves be optionally substituted. As used herein, "$C_5$-$C_{12}$ aromatic" refers to aromatic ring systems having 5 to 12 carbon atoms, such as phenyl, naphthalene and the like.

As used herein, the term "heteroaryl" refers to aryls as defined above where one or more carbons are substituted by heteroatoms. Exemplary heteroatoms include, but not limited to, nitrogen, sulfur, and oxygen. As used herein, "heteroaromatic" refers to refers to a monocyclic or multi-cyclic (fused) aromatic ring system, where one or more of the atoms in the ring system is a heteroatom, that is, an element other than carbon, including but not limited to, nitrogen, oxygen or sulfur. The term "heteroaromatic" used interchangeably with the term "heteroaryl" denotes a heterocyclic aromatic ring systems containing 5 to 12 atoms, with at least one, preferably two carbon atoms and one or more heteroatoms selected from nitrogen, oxygen and sulfur. Non-limiting examples include furan, thiophene, pyrrole, oxazole, thiazole, imidazole, pyrazole, isoxazole, thiazolem benzofuran, indole, benzothiophene, benzoimidazole, indazole, benzoxazole, benzoisoxazole, benzothiazole, isobenzofuran, isoindole, purine, pyridine, pyrazine, pyrimidine, pyrisazine, quinoline, quinozaline, quinazoline, isoquinoline, furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzothiazolyl, benzoisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like.

As used herein, "$C_5$-$C_{12}$ saturated cycloalkyl" refers to a saturated mono- or multi-cyclic ring system having 5 to 12 carbon atoms, preferably having 5 to 7 carbon atoms. Example of "$C_5$-$C_{12}$ cycloalkyl" groups include, but are not limited to cyclopentyl, cyclohexyl and cycloheptyl.

As used herein, "heterocycloalkyl" or "heterocyclyl" or the term "heterocyclic" refers to a monocyclic or multi-cyclic non-aromatic ring system having 5 to 12 members, preferably having 5 to 7 carbon atoms, where one or more, in certain embodiments, 1 to 3, of the atoms in the ring system is a heteroatom, that is, an element other than carbon, including but not limited to, nitrogen, oxygen or sulfur. Examples of "heteroalkyl" include, but are not limited to, pyran, 1,4-dioxane, 1,3-dioxane, piperidine, pyrrolidine, morpholine, tetrahydrothiopyran, tetrahydrothiophene, and the like. The term heterocycloalkyl" also encompasses non-aromatic ring being unsaturated or having one or more degrees of unsaturation containing one or more heteroatomic substitutions selected from S, SO, $SO_2$, O, or N. "heterocyclic" ring(s) or cycloalkyl ring(s). Examples of "heterocyclic" include, but not limited to, tetrahydrofuran, pyran, 1,4-dioxane, 1,3-dioxane, piperidine, pyrrolidine, morpholine, tetrahydrothiopyran, tetrahydrothiophene, and the like.

The term "N-containing group" is used herein a chemical group containing a nitrogen atom for example as amino group. The term "amino" as used herein encompass primary, secondary, tertiary or quaternary amines where the point of attachment is through the nitrogen atom which is substituted. For example, the "N-containing group" include N, NH, $NH_2$, tertiary amine (tertiary alkyl amine), quaternary ammonium (quaternary alkyl ammonium). The nitrogen atom may be substituted with alkyl. In case of a tertiary amine or quaternary amines, the substituent may be the same or may be different.

The term "bond" as used herein denotes a covalent bond. The bond may be between two similar atoms or between different atoms. Non-limiting examples include C—C, C—S, C—O, C—N. S—O, S—N, N—O and the like. It should be noted that a bond as defined above, for example, C—S encompasses both C—S and S—C and this holds for the bonds as defined herein.

The term "optionally substituted" refers to substitution with the named substituent or substituents, multiple degrees of substitution being allowed unless otherwise stated. The term substituted as used herein means that the compounds may contain one or more substituents, including, but not limited to, optionally substituted OH, $CF_3$, halogen, C(=O), C(=O)-alkyl, —COOH, —$NH_2$, CN, alkyl, alkenyl, alkynyl, alkylene, straight alkenylene, alkynylene, haloalkyl, haloalkenyl, haloalkynyl, alkoxy, carboxyl, halogen, ring system including five to twelve atoms, aromatic or heteroaromatic ring.

It should be noted that the carbon number, as used herein, refers to the carbon backbone and carbon branching, but does not include carbon atoms of the substituents, such as alkoxy substitutions and the like.

The invention also embraces solvates, pharmaceutically acceptable prodrugs, pharmaceutically active metabolites, and pharmaceutically acceptable salts of compounds of the formula (I) or any variations detailed herein.

The present disclosure also includes any or all of the stereochemical forms, including any enantiomeric or diastereomeric forms, and any tautomers or other forms of the compounds described.

As used herein the term "pharmaceutically acceptable salt" refers to salts derived from organic and inorganic acids of a compound described herein. Exemplary salts include, but are not limited to, sulfate, citrate, acetate, oxalate, chloride, hydrochloride, bromide, hydrobromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, succinate, fumarate, maleate, malonate, mandelate, malate, phthalate, and pamoate. The term "pharmaceutically acceptable salt" as used herein also refers to a salt of a compound described herein having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like. The term "pharmaceutically acceptable salt" also includes hydrates of a salt of a compound described herein.

The term "hydrate" refers to a compound formed by the addition of water. The hydrates may be obtained by any known method in the art by dissolving the compounds in water and recrystallizing them to incorporate water into the crystalline structure.

The compounds of the present invention, as defined above, may have the ability to crystallize in more than one form, a characteristic, which is known as polymorphism, and it is understood that such polymorphic forms ("polymorphs") are within the scope of formulae (I). Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

Certain of the compounds described herein may contain one or more chiral atoms, or may otherwise be capable of existing as two enantiomers or as two or more diastereomers. Accordingly, the compounds of this invention include mixtures of enantiomers as well as purified enantiomers or enantiomerically enriched mixtures. Furthermore, the compounds of this invention include mixtures of diastereomers, as well as purified stereoisomers or diastereomerically enriched mixtures. Also included within the scope of the invention are the individual isomers of the compounds of the invention, as defined above, as well as any wholly or partially mixtures thereof. The present invention also covers the individual isomers of the compounds represented by the formulas above as mixtures with isomers thereof in which one or more chiral centers are inverted.

The term "stereoisomer" as used herein is meant to encompass an isomer that possess identical constitution as a corresponding stereoisomer, but which differs in the arrangement of its atoms in space from the corresponding stereoisomer. For example, stereoisomers may be enantiomers, diastereomers and/or cis-trans (E/Z) isomers. It should be understood that a composition comprising a fatty acid amide of the invention may comprise single enantiomers, single diastereomers as well as mixtures thereof at any ratio (for example racemic mixtures, non racemic mixtures, mixtures of at least two diastereomers and so forth). Furthermore, the invention encompasses any stereoisomer of a fatty acid amide of the invention achieved through in vivo or in vitro metabolism, or by any type of synthetic rout.

Certain of the compounds described herein may contain one or more chiral atoms, or may otherwise be capable of existing as two enantiomers or as two or more diastereomers. Accordingly, the compounds of this invention include mixtures of enantiomers as well as purified enantiomers or enantiomerically enriched mixtures. Furthermore, the compounds of this invention include mixtures of diastereomers, as well as purified stereoisomers or diastereomerically enriched mixtures. Also included within the scope of the invention are the individual isomers of the compounds of the invention, as defined above, as well as any wholly or partially mixtures thereof. The present invention also covers the individual isomers of the compounds represented by the formulas above as mixtures with isomers thereof in which one or more chiral centers are inverted.

It is also noted that the compounds of the present invention may form tautomers. It is understood that all tautomers and mixtures of tautomers of the compounds of the present invention, are included within the scope of the compounds of the present invention.

The term "solvate" refers to an aggregate of a molecule with one or more solvent molecules, such as hydrate, alcoholate (aggregate or adduct with alcohol), and the like.

The term "physiologically functional derivative" used herein relates to any physiologically acceptable derivative of a compound as described herein.

The physiologically functional derivatives also include prodrugs of the compounds of the invention. Such prodrugs may be metabolized in vivo to a compound of the invention. These prodrugs may or may not be active themselves and are also an object of the present invention.

A "pharmaceutically acceptable prodrug" is a compound that may be converted under physiological conditions to the specified compound or to a pharmaceutically acceptable salt of such compound.

A "pharmaceutically active metabolite" is a pharmacologically active product produced through metabolism in the body of a specified compound or salt thereof. Metabolites of a compound may be identified using routine techniques known in the art and their activities determined using tests such as those described herein. Prodrugs and active metabolites of a compound may be identified using routine techniques known in the art.

In a further aspect, the invention relates to a composition comprising an effective amount of at least one apoptosis related protein in the TGF-beta signaling pathway (ARTS) mimetic compound having the general formula (I) or a pharmaceutically acceptable salt or hydrate thereof including any stereoisomer thereof, or any vehicle, matrix, nano- or micro-particle comprising the same. In more specific embodiments, formula I has the following structure:

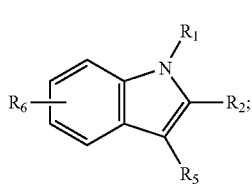

(I)

including any stereoisomer or salt thereof; wherein:

$R_1$ is independently selected from H, $C_1$-$C_{12}$ alkyl, $C_2$-$C_{12}$ alkenyl, $C_2$-$C_{12}$alkynyl;

$R_2$ is independently selected from —C(=O)—X—$R_3$, —S(=O)—X—$R_{3'}$;

X is a heteroatom independently selected from N-containing group, O and S;

$R_3$ and $R_{3'}$, independently of each other may be selected independently from H, $C_1$-$C_{12}$ alkyl, $C_2$-$C_{12}$ alkenyl, $C_2$-$C_{12}$alkynyl;

$R_5$ is -L1-$R_7$-L2-$R_8$; L1 and L2, independently of each other, are selected independently from —(CH$_2$)$_n$—; —NH—C(=O)—(CH$_2$)$_n$—, —C(=O)—NH —(CH$_2$)$_n$—; —S—S—(CH$_2$)$_n$—; —O—(CH$_2$)$_n$—; —NH—(CH$_2$)$_n$—; C(=O)—(CH$_2$)$_n$—; —S —(CH$_2$)$_n$—; —NH—S(=O)$_n$—(CH$_2$)$_n$—; n is independently 0 to 5;

$R_7$ is independently selected from straight or branched $C_1$-$C_{12}$ alkylene, straight or branched $C_2$-$C_{12}$ alkenylene, straight or branched $C_2$-$C_{12}$ alkynylene, a ring system containing five to twelve atoms, each optionally substituted; $R_8$ is independently selected from H, straight or branched $C_1$-$C_{12}$ alkyl, straight or branched $C_2$-$C_{12}$ alkenyl, straight or branched $C_2$-$C_{12}$ alkynyl, a ring system containing five to twelve atoms, each optionally substituted;

$R_6$ is independently selected from H, halogen, CN, NO$_2$, $C_1$-$C_{12}$ alkoxy, straight or branched $C_1$-$C_{12}$ alkyl, straight or branched $C_2$-$C_{12}$ alkenyl, straight or branched $C_2$-$C_{12}$ alkynyl. In some specific embodiments, the composition of the invention may optionally further comprise at least one of pharmaceutically acceptable carrier/s, excipient/s, auxiliaries, and/or diluent/s.

In some embodiments, the ARTS mimetic compound is as defined by the invention herein before.

In yet some further aspects, the invention provides a composition comprising an effective amount of any of the compounds of the invention as described above or any vehicle, matrix, nano- or micro-particle comprising the same, specifically, the compounds of any one of the compounds of Formulas I, II, III, IV, V, VI, VII, as well as the compounds of formulas VIII, IX as described herein and any or any analogs or derivative thereof including any stereoisomer or salt thereof for use in a method for treating, preventing, inhibiting, reducing, eliminating, protecting or delaying the onset of a proliferative disorder in a subject in need thereof. In yet some further embodiments, the invention provides a composition comprising an effective amount of the compounds as described herein or any vehicle, matrix, nano- or micro-particle comprising the same for use in a method for inducing differentiation, specifically, differentiation of premalignant cells in a subject in need thereof.

In some specific embodiments, the composition of the invention may comprise an effective amount of the ARTS mimetic compound having the formula (d), or any analogs or derivative thereof including any stereoisomer or salt thereof.

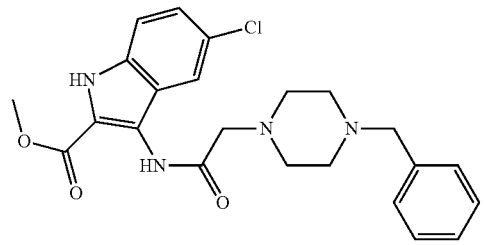

(d)

3-[2-(4-Benzyl-piperazin-1-yl)-acetylamino]-5-chloro-1H-indole-2-carboxylic acid methyl ester It should be appreciated that such compound may be referred to herein by the present application as "A4" or "ARTS mimetic A4 small molecule" or the like. It should be also noted that the when referring to A4, the compound may include any stereoisomer or salt thereof, for example the stereoisomer having the structure:

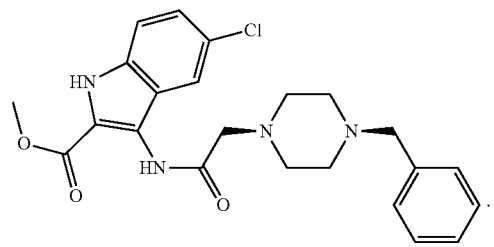

The invention provides different ARTS mimetic compounds that specifically mimic the C' domain of ARTS, specifically in binding thereof to its binding site within the BIR3 domain of XIAP.

As used herein "ARTS" (apoptosis-related protein in the TGF-β signaling pathway) is a septin-like mitochondrial protein derived from alternative splicing of the H5/PNUTL2/hCDCrel2a/2b gene. ARTS acts as a tumor suppressor protein that functions as an antagonist of XIAP and thereby promotes apoptosis.

It should be appreciated that in certain embodiments, as used herein in the specification and in the claim section below, ARTS protein refers to the human ARTS (as denoted by SEQ ID NO. 1). More specifically, the human ARTS protein comprises an amino acid sequence of 274 amino acid residues as denoted by GenBank Accession No. AF176379, encoded by a nucleic acid sequence of SEQ ID NO. 2.

In certain embodiments, the ARTS mimetic compound comprised within the composition/s of the invention may induce cell differentiation.

The term "differentiation" is the process by which cells become progressively more specialized. Differentiation can be induced by intrinsic factors or by extrinsic compounds and is a normal process through which cells mature. Stem cells can differentiate to several cell types acquiring specific structural and functional characteristics. As used herein, this term refers to transition of cells from malignant phenotype to normal cell phenotype. Specifically, differentiation process encompasses conversion of malignant cells, to the original lineage of the cells that are similar to their normal counterparts. During this process cells acquire the characteristic hierarchy organization of normal cells in vitro or in vivo.

In more specific embodiments, the ARTS mimetic compound may promote at least one of apical and basal polarization in at least one cell. In some embodiments such cell may be a premalignant or a malignant cell.

In some further embodiments the ARTS mimetic compound of the invention may restore a normal-like phenotype in the premalignant or malignant cells.

In more particular embodiments, such cell may be any one of a premalignant epithelial cell and an epithelial carcinoma cell.

In yet more specific embodiments, the ARTS mimetic compound of the invention and any compositions thereof may induce lumen formation by such epithelial cells.

It should be understood that the ARTS mimetic compound/s of the invention and any composition comprising the same may induce differentiation and restore a normal-like phenotype in cells of any malignant or premalignant epithelial tissue. In more specific embodiments, such epithelial tissue may be any epithelial tissue of an organ involving apicobasal polarization of the cells. In yet more specific embodiment, such cells may be cells of a malignant or premalignant condition in an organ involving epithelial lumen formation and/or apicobaso-lateral polarization. Such organs or tissue may include, but are not limited to mammalian lung, gastro-intestinal tracks, mammary gland, kidney, prostate, salivary gland, thymus, endocrine glands, collecting ducts and the like.

In more specific embodiments, the ARTS mimetic compound/s of the invention and any composition comprising the same may induce differentiation, apicobasal polarity and lumen formation in any one of premalignant epithelial breast cell/s and epithelial breast carcinoma cell/s. According to some embodiments, induction of apical polarization is evident and detected using the cis-Golgi protein GM130 specific antibodies and Basal polarization of normal acini may be detected by laminin 5 antibodies.

In more particular embodiments, the ARTS mimetic compound/s of the invention may induce formation of acini-like organoids characterized by a hollow lumen by said epithelial breast cells reminiscent of the normal breast tissue. Thus, in some embodiments, the ARTS mimetic compound of the invention, specifically, the compound A4 or any derivatives, analogs, including any stereoisomer or salt thereof, any vehicle, matrix, nano- or micro-particle, or composition comprising the same, may reverse the disturbed neoplastic architecture of premalignant or malignant epithelial breast cells and promotes polarization and lumen formation resembling to normal acini of the mammary gland tissue. These effects were clearly demonstrated in Example 7.

In some particular embodiments, such epithelial breast cell may be for example, a cell of a ductal carcinoma in situ (DCIS) cell, a cell of Usual Ductal Hyperplasia (UDH) or an atypical ductal hyperplasia (ADH) cell.

In further embodiments, the ARTS mimetic compound/s of the invention and specifically the "A4" compound as defined herein above, leads to ubiquitin proteasome system (UPS) mediated degradation of at least one of B-cell lymphoma 2 (Bcl-2) and X-linked-Inhibitor of Apoptosis (XIAP) in a cell. Such effect has been clearly demonstrated by FIG. 4A-4C. In further embodiments, the reduction in Bcl-2 and/re XIAP caused by the ARTS mimetic compounds of the invention, specifically, A4 may lead to reduced proliferation and survival of said cell/s, as also demonstrated by Example 6. In addition, induction of apoptosis may also lead to differentiation. Therefore, in yet some further embodiments, the ARTS mimetic compounds of the invention, specifically, ARTS mimetic compound "A4" may induce apoptosis in cells, specifically, malignant cells (as also shown in Table 1 and Example 9).

More specifically, as shown by the Examples, the ARTS mimetic compounds of the invention act as XIAP and $Bcl_2$ antagonists, leading to UPS mediated degradation of XIAP and $Bcl_2$. The invention thus provides a novel antagonist for Bcl-2 protein. As used herein the term Bcl-2 prosurvival protein refers to a proto-oncogenic protein known as an apoptosis inhibitor. The Bcl-2 protein forms the basis of a growing family of related proteins collectively denoted herein as Bcl-2 family of proteins. These proteins are known to control apoptotic cell death by the mitochondrial pathway.

As appreciated in the art, the members of the Bcl-2 family are either pro-survival or pro-apoptotic but regardless of their activity, they all share significant sequence and structural homology. Specifically, the Bcl-2 family of proteins is characterized by up to four regions of sequence homology, known as the Bcl-2 homology (BH) domains.

As previously described in the art, the Bcl-2 family of proteins includes three different groups of proteins: the first group is a pro-survival or anti-apoptotic group denoted herein as "Bcl-2 pro-survival proteins", the second group is a pro-apoptotic group including BAX and BAK; and a third group denoted herein as BH3-only proteins that exhibit a pro-apoptotic activity.

The ARTS mimetic compound/s of the invention antagonizes the anti-apoptotic activity of the pro-survival Bcl-2 protein leading to decreased proliferation of the cells. The "Bcl-2 pro-survival proteins" or "anti-apoptotic" or "Bcl-2 like" as used herein denotes a group of proteins responsible for protecting cells from apoptotic stimuli and are sequentially characterized by containing all four BH domains.

Bcl-2 (B-cell CLL/lymphoma 2) as used herein, is an integral outer mitochondrial membrane protein that blocks the apoptotic death of some cells such as lymphocytes. Bcl-2 suppresses apoptosis in a variety of cell systems including factor-dependent lympho-hematopoietic and neural cells. It regulates cell death by controlling the mitochondrial membrane permeability. Bcl-2 appears to function in a feedback loop system with caspases, it inhibits caspase activity either by preventing the release of cytochrome c from the mitochondria and/or by binding to the apoptosis-activating factor (APAF-1). It should be noted that in certain embodiments, the invention refers to the human Bcl-2 protein as denoted by GenBank Accession No. NP_000624 and SEQ ID NO: 3 and NP_000648 of SEQ ID NO:4), encoded by the Bcl-2 gene of GenBank Accession No. NM_000633 of SEQ ID NO: 5 and NM_000657 of SEQ ID NO:6.

As recently shown by the inventors, ARTS binds to XIAP through a domain comprising 27 residues covering the C-terminus of ARTS. This interaction induces auto degradation of XIAP. The ARTS mimetic compound/s of the invention target BRI3 domain of XIAP mimicking the ability of ARTS to enhance XIAP degradation.

Moreover, as show in FIG. 4, the ARTS mimetic compound of the invention, specifically, the "A4" compound, binds directly to XIAP and leads to proteasome mediated degradation thereof as well as to degradation of $Bcl_2$.

As used herein the term "IAPs" denotes a family of proteins that harbor between one to three copies of a baculovirus IAP repeat (BIR) domain that enable interaction with activated caspases.

It was previously suggested that the BIR domains of certain IAPs, in particular XIAP, have the ability to directly inhibit caspase activity in vitro.

X-linked inhibitor of apoptosis protein (XIAP), also known as inhibitor of apoptosis protein 3 (IAP3) and baculoviral IAP repeat-containing protein 4 (BIRC) denotes a protein known to stop an apoptotic process and thus inhibit cell death. In human, XIAP is produced by a gene named XIAP gene located on the X chromosome. XIAP is also called human IAP-like Protein (hILP), because it is not as well conserved as the human IAPS: hIAP-1 and hIAP-2- XIAP is the most potent human IAP protein currently identified.

XIAP belongs to a family of apoptotic suppressor proteins. Members of this family share a conserved motif termed, baculovirus IAP repeat (BIR domain), which is necessary for their anti-apoptotic function. XIAP acts as a direct caspase inhibitor by directly binding to the active site pocket of CASP3 and CASP7 and obstructs substrate entry. It further inactivates CASP9 by keeping it in a monomeric, inactive state.

It should be noted that in certain embodiments, the invention relates to the human XIAP protein (GenBank Accession Nos. NP_001158, NP_001191330, as denoted by SEQ ID NO. 9) encoded by the XIAP gene (GenBank Accession Nos. NM_001167, NM_001204401, as denoted by SEQ ID NO. 10).

In yet another embodiment, the ARTS mimetic compounds of the invention bind XIAP thereby leading to UPS mediated degradation of Bcl-2. As such, they may further act on other Bcl-2 family members. Thus, in some embodiments the ARTS mimetic compounds of the invention may antagonize Bcl-xL. B-cell lymphoma-extra large (Bcl-xL) as used herein, is a transmembrane molecule in the mitochondria. It is a member of the Bcl-2 family of proteins, and acts as a pro-survival protein by preventing the release of mitochondrial contents such as cytochrome c, which would lead to caspase activation. In certain embodiments the invention relates to the human Bcl-xL protein (GenBank Accession No. CAA80661 SEQ ID NO: 7), encoded by the Bcl-xL gene as denoted by GenBank Accession No. Z23115 and SEQ ID NO: 8.

In yet another embodiment, the ARTS mimetic compounds of the invention may antagonize any one of the human Bcl-2 pro-survival proteins Mcl-1, Bcl-w, A1/Bfl-1 and Bcl-B/Bcl2L10 as denoted by accession number: AAF64255, AAB09055, NP_033872 and NP_065129, respectively.

As indicated above, the present invention relates to the ARTS mimetic compounds of the invention that act as antagonist/s of XIAP and Bcl-2. An antagonist is a compound that competes with a specific protein, a ligand for example, on binding to another protein, a receptor for example. Such binding usually, induces a specific biological response or action that is blocked by the competing antagonist. Antagonists have affinity but no efficacy for their cognate binding protein and binding will disrupt the interaction and inhibit the function of such cognate protein. Antagonists mediate their effects by binding to the active (orthosteric=right place) site or to allosteric (=other place) sites on any cognate protein, in this case, XIAP (or receptor, in case applicable), or they may interact at unique binding sites not normally involved in the biological regulation of the cognate protein.

As shown in the Examples, down regulation of XIAP and Bcl-2 protein levels was observed in the presence of the ARTS mimetic compounds of the invention. In addition, the results shown in Example 9, demonstrate that the down-regulation of XIAP and Bcl-2 levels are mediated by the ubiquitin—proteasome machinery (UPS).

Thus, in certain embodiments, the ARTS mimetic compounds of the invention, mediate ubiquitin proteasome system (UPS) degradation of XIAP anti-apoptotic protein and Bcl-2 prosurvival protein, thereby reducing survival of the cells.

As used herein the term "ubiquitin proteasome system" denotes a multi component system that identifies and degrades unneeded, damaged or misfolded proteins by breaking peptide bonds (proteolysis) of the protein in the cytoplasm of cells. As appreciated in the art, degradation of a protein via the UPS involves two discrete and successive steps. In the first step, proteins are tagged for degradation with a small protein called ubiquitin. The tagging reaction is catalyzed by enzymes called ubiquitin ligases. Once a protein is tagged with a single ubiquitin molecule, this is a signal to other ligases to attach additional ubiquitin molecules.

More specifically, conjugation of ubiquitin, a highly evolutionarily conserved 76 amino acid residue polypeptide, to the protein substrate proceeds via a three-step cascade mechanism involving E1, E2 and E3 enzymes. By successively adding activated ubiquitin moieties to internal lysine residues on the previously conjugated ubiquitin molecule, a polyubiquitin chain is synthesized that is subsequently recognized by the downstream 26S proteasome complex.

In the second step, degradation of polyubiquitinated substrates is carried out by a large, protease complex, referred to as the 26S proteasome that does not recognize nonmodified substrates. The proteasomes are multicatalytic protease protein complexes found in all cells that degrades polyubiquitinated proteins to short peptides by breaking peptide bonds (proteolysis). Following degradation of the substrate, short peptides derived from the substrate are released, along with reusable ubiquitin.

It should be noted that the ubiquitin-proteasome system (UPS) plays a central and complex role in regulating apoptosis by directly targeting key cell death proteins, including caspases.

The term "apoptosis" refers to a regulated network of biochemical events which lead to a selective form of cell suicide and is characterized by readily observable morphological and biochemical phenomena. Cells undergoing apoptosis show characteristic morphological and biochemical features. These features include chromatin aggregation or condensation, DNA fragmentation, nuclear and cytoplasmic condensation, partition of cytoplasm and nucleus into membrane bound vesicles (apoptotic bodies) which contain ribosomes, morphologically intact mitochondria and nuclear material. Cytochrome C release from mitochondria is seen as an indication of mitochondrial dysfunction accompanying apoptosis.

As indicated above, apoptosis is a tightly controlled form of active cell death that is necessary for development and organismal homeostasis. Death by the apoptotic pathway is achieved among others, by the activation of a family of highly potent and specific proteases, termed caspases (for cysteine-aspartate protease).

The activity of caspases is tightly regulated and the cell maintains several "checkpoints" to control their activity. The first level of regulation is intrinsic to caspases themselves. Caspases are initially transcribed as weakly active zymogens, which only upon proper stimulation are cleaved to form the active enzyme.

The second level of caspase regulation is achieved by inhibitors, namely the family of proteins called IAPs (Inhibitor of Apoptosis Protein) as described above.

Still further, in some embodiments, the ARTS mimetic compound of the invention as well as any composition comprising the same in accordance with the invention may induce or promote at least one of: cell differentiation, apicobasal polarization and initiation of lumen formation thereby restoring a normal-like phenotype of a tissue comprising said premalignant or malignant epithelial cells in a subject in need thereof.

In yet some further embodiments, the ARTS mimetic compounds of the invention, specifically, the "A4" compound or any derivatives thereof may induce killing of malignant cells as also demonstrated in Example 9 and Table 1. In some specific embodiments, the A4 compound may induce cell death in variety of cell lines, specifically, cancerous cell lines of different tissue origin that include placenta, kidney, skin, liver, pancreas, muscle, lungs, bone, hematological cancers, colon, bladder prostate, ovary, breast and cervical carcinoma. As shown in the table, these sensitive cells include but are not limited to HT29, A2780, HEK293, MT3, L-363, TE671, UMUC3, A204, PANC1, NCIH82, MCF7, WSU—NHL, SU-DHL-6, JAR, PLCPRF5, 22RV1, NCIH358M, HCT15, MV4-11, SKMEL5, HL-60, A375, MHHES1, K-562, C33A, JEG3, 5637, MDAMB435, U20S, MIAPACA2, PANC1005, LOVO, ACHN, A549, NCIH460, MDAMB468, 7860, SKNSH, MG63, MINO, UO31, A673, RAMOS, JIMT1, MDAMB436. In yet some further embodiments, such cell death may be an apoptotic cell death. In yet some further embodiments, such apoptotic cell death may initiate differentiation in t the treated cell population. As shown by Table 1, most of the brain tumor cell lines, as well as normal tissues (PBMCs and connective tissue) demonstrated resistance to the ARTS mimetic compound of the invention A4. More specifically, GRANTA-519, SU-DHL-10, COLO205, SAOS2, HT1080, HEPG2, CLS439, T24, SKBR3, IGROV1, KASUMI-1, CACO2, CAKI1, SKHEP1, DLD1, DU145, CASKI, EJ28, OVCAR3, EFO21, HELA, A431, SKMEL28, BXPC3, PC3, CALU6, SF295, IMR90, HS578T, THP-1, U87MG, SF268, J82, OVCAR4, MDAMB231, SW620, SKLMS1, HCT116, ASPC1, SNB75, SKNAS, NCIH292, RD, RDES, HS729, SKOV3, COLO678, BT20 and PBMC cells were resistant (table 1), Thus, the invention further provides pharmaceutical compositions for the treatment of a subject suffering from a proliferative disorder or pre-malignancy.

As mentioned herein before, the compositions provided by the invention optionally further comprise at least one pharmaceutically acceptable excipient or carrier. As used herein "pharmaceutically acceptable carrier" includes any and all solvents, dispersion media, coatings and the like. The use of such media and agents for pharmaceutical active substances is well known in the art. Except as any conventional media or agent is incompatible with the active ingredient, its use in the therapeutic composition is contemplated.

As mentioned above, the compositions provided by the invention comprise an effective amount of any of the ARTS mimetic compounds of the invention, specifically, the A4 compound including any stereoisomer or salt thereof, as well as any vehicle, matrix, nano- or micro-particle comprising the same.

Of particular relevance are formulations of compositions of the invention adapted for use as a nano- or microparticles. Nanoscale drug delivery systems using liposomes and nanoparticles are emerging technologies for the rational drug delivery, which offers improved pharmacokinetic properties, controlled and sustained release of drugs and, more importantly, lower systemic toxicity. A particularly desired solution allows for externally triggered release of encapsulated compounds. Externally controlled release can be accomplished if drug delivery vehicles, such as liposomes or polyelectrolyte multilayer capsules, incorporate nanoparticle (NP) actuators.

More specifically, Controlled drug delivery systems (DDS) have several advantages compared to the traditional forms of drugs. A drug is transported to the place of action, hence, its influence on vital tissues and undesirable side effects can be minimized. Accumulation of therapeutic compounds in the target site increases and, consequently, the required doses of drugs are lower. This modern form of therapy is especially important when there is a discrepancy between the dose or the concentration of a drug and its therapeutic results or toxic effects. Cell-specific targeting can be accomplished by attaching drugs to specially designed carriers. Various nanostructures, including liposomes, polymers, dendrimers, silicon or carbon materials, and magnetic nanoparticles, have been tested as carriers in drug delivery systems. Polymeric nanoparticles are one technology being developed to enable clinically feasible oral delivery.

The pharmaceutical composition of the invention can be administered and dosed by the methods of the invention, in accordance with good medical practice. More specifically, the compositions used in the methods and kits of the invention, described herein after, may be adapted for administration by systemic, parenteral, intraperitoneal, transdermal, oral (including buccal or sublingual), rectal, topical (including buccal or sublingual), vaginal, intranasal and any other appropriate routes. Such formulations may be prepared by any method known in the art of pharmacy, for example by bringing into association the active ingredient with the carrier(s) or excipient(s).

The phrases "systemic administration," "administered systemically," "peripheral administration" and "administered peripherally" as used herein mean the administration of a compound, drug or other material other than directly into the central blood system, such that it enters the patient's system and, thus, is subject to metabolism and other like processes. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

The pharmaceutical forms suitable for injection use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

In the case of sterile powders for the preparation of the sterile injectable solutions, the preferred method of preparation are vacuum-drying and freeze drying techniques which yield a powder of the active ingredient plus any additional desired ingredient from a previously sterile-filtered solution thereof.

Pharmaceutical compositions used to treat subjects in need thereof according to the invention generally comprise a buffering agent, an agent who adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

Local administration to the area in need of treatment may be achieved by, for example, local infusion during surgery, topical application, direct injection into the specific organ, etc.

Compositions and formulations for oral administration include powders or granules, suspensions or solutions in water or non-aqueous media, capsules, sachets, lozenges (including liquid-filled), chews, multi- and nano-particulates, gels, solid solution, liposome, films, ovules, sprays or tablets. Thickeners, flavoring agents, diluents, emulsifiers, dispersing aids or binders may be desirable.

Pharmaceutical compositions used to treat subjects in need thereof according to the invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general formulations are prepared by uniformly and intimately bringing into association the active ingredients with liquid carriers or finely divided solid carriers or both, and then, if necessary, shaping the product. The compositions may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The pharmaceutical compositions of the present invention also include, but are not limited to, emulsions and liposome-containing formulations.

It should be understood that in addition to the ingredients particularly mentioned above, the formulations may also include other agents conventional in the art having regard to the type of formulation in question, for example those suitable for oral administration may include flavoring agents.

In particular embodiments, the unit dosage formulations are those containing a daily dose or sub-dose, as herein above recited, or an appropriate fraction thereof, of an active ingredient.

In yet a further aspect, the invention relates to a method for inducing differentiation in a cell. In more specific embodiments, the method comprising the step of contacting the cell with an effective amount of at least one of: ARTS or any functional fragment or peptide thereof, at least one ARTS mimetic compound, any combination thereof or any composition comprising the same, wherein said ARTS mimetic compound having the general formula (I) or a pharmaceutically acceptable salt or hydrate thereof including any stereoisomer thereof:

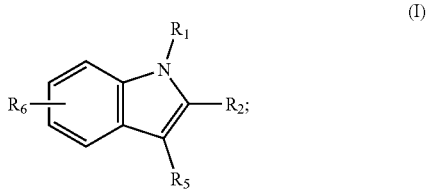

(I)

wherein:
$R_1$ is independently selected from H, $C_1$-$C_{12}$ alkyl, $C_2$-$C_{12}$ alkenyl, $C_2$-$C_{12}$alkynyl;
$R_2$ is independently selected from —C(=O)—X—$R_3$, —S(=O)—X—$R_{3'}$;
X is a heteroatom independently selected from N-containing group, O and S;
$R_3$ and $R_{3'}$, independently of each other may be selected independently from H, $C_1$-$C_{12}$ alkyl, $C_2$-$C_{12}$ alkenyl, $C_2$-$C_{12}$alkynyl;
$R_5$ is -L1-$R_7$-L2-$R_8$; L1 and L2, independently of each other, are selected independently from —(CH$_2$)$_n$—; —NH—C(=O)—(CH$_2$)$_n$—, —C(=O)—NH —(CH$_2$)$_n$—; —S—S—(CH$_2$)$_n$—; —O—(CH$_2$)$_n$—;

—NH—(CH$_2$)$_n$—; C(=O)—(CH$_2$)$_n$—; —S—(CH$_2$)$_n$—; —NH—S(=O)$_n$—(CH$_2$)$_n$—; n is independently 0 to 5;

R$_7$ is independently selected from straight or branched C$_1$-C$_{12}$ alkylene, straight or branched C$_2$-C$_{12}$ alkenylene, straight or branched C$_2$-C$_{12}$ alkynylene, a ring system containing five to twelve atoms, each optionally substituted;

R$_8$ is independently selected from H, straight or branched C$_1$-C$_{12}$ alkyl, straight or branched C$_2$-C$_{12}$ alkenyl, straight or branched C$_2$-C$_{12}$ alkynyl, a ring system containing five to twelve atoms, each optionally substituted;

R$_6$ is independently selected from H, halogen, CN, NO$_2$, C$_1$-C$_{12}$ alkoxy, straight or branched C$_1$-C$_{12}$ alkyl, straight or branched C$_2$-C$_{12}$ alkenyl, straight or branched C$_2$-C$_{12}$ alkynyl.

In certain embodiments the ARTS mimetic compound/s used by the method of the invention may be any compound as defined by the invention. In further embodiments, the method of the invention may involves the use of any of the compositions encompassed by the invention, and specifically, any of the compositions as described herein above.

As demonstrated in Example 5, overexpression of ARTS induce differentiation in pre-malignant cells. Therefore, in certain embodiments, the invention further encompass the use of the ARTS polypeptide and any fragments or peptides thereof. Thus, in such specific embodiments, the invention further provides methods for inducing differentiation in cells or in a subject, comprising the step of contacting said cells with an effective amount of ARTS, any fragments thereof or any composition comprising the same. In some specific embodiments, these cells may be pre-malignant or malignant cells and the subject may be a subject having premalignant or malignant cells. Specifically peptides derived from ARTS C'-terminal domain, more specifically, peptides derived from 27 amino acid sequence of ARTS C'-terminus. In more specific embodiments, the ARTS C' terminus may comprise the amino acid sequence of: YGPSLRLLAPPGAVKGTGQEHQGQGCH, as denoted by SEQ ID NO. 16. In some particular embodiments, such ARTS fragments or peptides may comprise any peptide derived from of the ARTS C' terminal 27 amino acid residues. In more specific embodiments, such peptides may comprise the amino acid sequence of any one of YGPSLRLLA, as denoted by SEQ ID NO. 17, PPGAVKGTG, as denoted by SEQ ID NO. 18, and QEHQGQGCH, as denoted by SEQ ID NO. 19.

In yet some further embodiments, ARTS fragments derived from its N-terminus, may be used for inducing differentiation as described above. In more specific embodiments, such ARTS fragments may include ARTS BH3-like domain. In some particular embodiments, such BH3-like domain ARTS fragments may comprise the amino acid sequence of residues 1-128, 1-148, 106-148, 106-133, 106-128, 112-148, 112-133 and 112-128 of ARTS N'-terminus, as denoted by any one of SEQ ID NO. 20 to 27, respectively.

The term "polypeptide" as used herein refers to amino acid residues, connected by peptide bonds. A polypeptide sequence is generally reported from the N-terminal end containing free amino group to the C-terminal end containing free carboxyl group.

More specifically, "Amino acid molecule", "Amino acid sequence" or "peptide sequence" is the order in which amino acid residues connected by peptide bonds, lie in the chain in peptides and proteins. The sequence is generally reported from the N-terminal end containing free amino group to the C-terminal end containing amide. Amino acid sequence is often called peptide, protein sequence if it represents the primary structure of a protein, however one must discern between the terms "Amino acid sequence" or "peptide sequence" and "protein", since a protein is defined as an amino acid sequence folded into a specific three-dimensional configuration and that had typically undergone post-translational modifications, such as phosphorylation, acetylation, glycosylation, manosylation, amidation, carboxylation, sulfhydryl bond formation, cleavage and the like.

Amino acids, as used herein refer to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" refers to compounds that have the same fundamental chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

It should be noted that in addition to any of the ARTS derived fragments or peptides described herein, the invention further encompasses any derivatives, analogues, variants or homologues of any of the peptides. The term "derivative" is used to define amino acid sequences (polypeptide), with any insertions, deletions, substitutions and modifications to the amino acid sequences (polypeptide) that do not alter the activity of the original polypeptides. By the term "derivative" it is also referred to homologues, variants and analogues thereof, as well as covalent modifications of a polypeptides made according to the present invention.

It should be further noted that the polypeptides according to the invention can be produced synthetically, or by recombinant DNA technology. Methods for producing polypeptides peptides are well known in the art.

In some embodiments, derivatives include, but are not limited to, polypeptides that differ in one or more amino acids in their overall sequence from the polypeptides defined herein (either the ARTS protein or any fragment or peptide derived therefrom according to the invention), polypeptides that have deletions, substitutions, inversions or additions.

In some embodiments, derivatives refer to polypeptides, which differ from the polypeptides specifically defined in the present invention by insertions of amino acid residues. It should be appreciated that by the terms "insertions" or "deletions", as used herein it is meant any addition or deletion, respectively, of amino acid residues to the polypeptides used by the invention, of between 1 to 50 amino acid residues, between 20 to 1 amino acid residues, and specifically, between 1 to 10 amino acid residues. More particularly, insertions or deletions may be of any one of 1, 2, 3, 4, 5, 6, 7, 8, 9, or 10 amino acids. It should be noted that the insertions or deletions encompassed by the invention may occur in any position of the modified peptide, as well as in any of the N' or C' termini thereof.

The peptides of the invention may all be positively charged, negatively charged or neutral. In addition, they may be in the form of a dimer, a multimer or in a constrained conformation, which can be attained by internal bridges, short-range cyclizations, extension or other chemical modifications.

The polypeptides of the invention can be coupled (conjugated) through any of their residues to another peptide or agent. For example, the polypeptides of the invention can be coupled through their N-terminus to a lauryl-cysteine (LC) residue and/or through their C-terminus to a cysteine (C) residue.

Further, the peptides may be extended at the N-terminus and/or C-terminus thereof with various identical or different amino acid residues. As an example for such extension, the peptide may be extended at the N-terminus and/or C-terminus thereof with identical or different amino acid residue/s, which may be naturally occurring or synthetic amino acid residue/s. An additional example for such an extension may be provided by peptides extended both at the N-terminus and/or C-terminus thereof with a cysteine residue. Naturally, such an extension may lead to a constrained conformation due to Cys-Cys cyclization resulting from the formation of a disulfide bond. Another example may be the incorporation of an N-terminal lysyl-palmitoyl tail, the lysine serving as linker and the palmitic acid as a hydrophobic anchor. In addition, the peptides may be extended by aromatic amino acid residue/s, which may be naturally occurring or synthetic amino acid residue/s, for example, a specific aromatic amino acid residue may be tryptophan. The peptides may be extended at the N-terminus and/or C-terminus thereof with various identical or different organic moieties, which are not naturally occurring or synthetic amino acids. As an example for such extension, the peptide may be extended at the N-terminus and/or C-terminus thereof with an N-acetyl group.

For every single peptide sequence defined by the invention and disclosed herein, this invention includes the corresponding retro-inverse sequence wherein the direction of the peptide chain has been inverted and wherein all the amino acids belong to the D-series.

The invention also encompasses any homologues of the polypeptides (either the ARTS protein or any fragments or peptides thereof) specifically defined by their amino acid sequence according to the invention. The term "homologues" is used to define amino acid sequences (polypeptide) which maintain a minimal homology to the amino acid sequences defined by the invention, e.g. preferably have at least about 65%, more preferably at least about 75%, even more preferably at least about 85%, most preferably at least about 95% overall sequence homology with the amino acid sequence of any of the polypeptide as structurally defined above, e.g. of a specified sequence, more specifically, an amino acid sequence of the polypeptides as denoted by any one of SEQ ID NOs. 16, 17, 18 and 19 or alternatively, any one of SEQ ID NO. 20 to 27.

More specifically, "Homology" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N- nor C-terminal extensions nor insertions or deletions shall be construed as reducing identity or homology. Methods and computer programs for the alignment are well known in the art.

In some embodiments, the present invention also encompasses polypeptides which are variants of, or analogues to, the polypeptides specifically defined in the invention by their amino acid sequence. With respect to amino acid sequences, one of skill will recognize that individual substitutions, deletions or additions to peptide, polypeptide, or protein sequence thereby altering, adding or deleting a single amino acid or a small percentage of amino acids in the encoded sequence is a "conservatively modified variant", where the alteration results in the substitution of an amino acid with a chemically similar amino acid.

Conservative substitution tables providing functionally similar amino acids are well known in the art. Such conservatively modified variants are in addition to and do not exclude polymorphic variants, interspecies homologues, and alleles and analogous peptides of the invention.

For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another:
  1) Alanine (A), Glycine (G);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V);
  6) Phenylalanine (F), Tyrosine (Y), Tryptophan (W);
  7) Serine (S), Threonine (T); and
  8) Cysteine (C), Methionine (M)

More specifically, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar "hydrophobic" amino acids are selected from the group consisting of Valine (V), Isoleucine (I), Leucine (L), Methionine (M), Phenylalanine (F), Tryptophan (W), Cysteine (C), Alanine (A), Tyrosine (Y), Histidine (H), Threonine (T), Serine (S), Proline (P), Glycine (G), Arginine (R) and Lysine (K); "polar" amino acids are selected from the group consisting of Arginine (R), Lysine (K), Aspartic acid (D), Glutamic acid (E), Asparagine (N), Glutamine (Q); "positively charged" amino acids are selected form the group consisting of Arginine (R), Lysine (K) and Histidine (H) and wherein "acidic" amino acids are selected from the group consisting of Aspartic acid (D), Asparagine (N), Glutamic acid (E) and Glutamine (Q).

In certain embodiments the peptide compounds of the invention may comprise one or more amino acid residue surrogate. An "amino acid residue surrogate" as herein defined is an amino acid residue or peptide employed to produce mimetics of critical function domains of peptides.

Examples of amino acid surrogate include, but are not limited to chemical modifications and derivatives of amino acids, stereoisomers and modifications of naturally occurring amino acids, non-protein amino acids, post-translationally modified amino acids, enzymatically modified amino acids, and the like. Examples also include dimers or multimers of peptides. An amino acid surrogate may also include any modification made in a side chain moiety of an amino acid. This thus includes the side chain moiety present in naturally occurring amino acids, side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like.

It should be appreciated that the invention further encompass any of the peptides of the invention any serogates thereof, any salt, base, ester or amide thereof, any enantiomer, stereoisomer or disterioisomer thereof, or any combination or mixture thereof. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts.

It should be noted that the invention further encompasses any peptidomimetic compound mimicking the C'-terminus derived peptides used by the invention. When referring to peptidomimetics, what is meant is a compound that mimics the conformation and desirable features of a particular natural peptide but avoids the undesirable features, e.g., flexibility and bond breakdown. From chemical point of view, peptidomimetics can have a structure without any peptide bonds, nevertheless, the compound is peptidomimetic due to its chemical properties and not due to chemical structure. Peptidoinimetics (both peptide and non-peptidyl analogues) may have improved properties (e.g., decreased proteolysis, increased retention or increased bioavailability). It should be noted that peptidomimetics may or may not have similar two-dimensional chemical structures, but share common three-dimensional structural features and geometry. Each peptidomimetic may further have one or more unique additional binding elements.

In some embodiments, the methods of the invention may be particularly applicable for inducing differentiation of pre-malignant or malignant epithelial cells into normal-like epithelial cells.

In more specific embodiments, the methods of the invention may be effective for inducing differentiation of pre-malignant or malignant epithelial cells in a subject in need thereof.

According to certain embodiments, the subject may be a mammalian subject suffering from a proliferative disorder. In mores specific embodiments, said proliferative disorder may be any one of a pre-malignancy and carcinoma. More specifically, any pre-malignancy and carcinoma affecting organs involving apicobasal polarization of epithelial cells. In more specific embodiments, the methods of the invention may be applicable for subject suffering from a malignant or premalignant condition in organs or tissues involving lumen formation and apicobasal polarity. Non-limiting examples include, but are not limited to mammalian lung, mammary gland, kidney, salivary gland, prostate, bladder, intestinal tract, endocrinal glands and the like. In some further specific embodiments, the subject may be a subject suffering from breast carcinoma. In more particular embodiments, the subject is suffering from any one of ADH, UDH and DCIS. In yet some further embodiments, the methods of the invention may be applicable for subjects suffering from a malignant or premalignant condition in the lung, prostate, thyroid or kidney. It should be appreciated that the method of the invention may be applicable for subjects suffering from any malignant or premalignant condition involving loss of epithelial cell polarity.

In yet another aspect, the invention provides a method for treating, preventing, inhibiting, reducing, eliminating, protecting or delaying the onset of a proliferative disorder in a subject in need thereof. In more specific embodiments the method comprising administering to such subject a therapeutically effective amount of at least one ARTS mimetic compound/s including any stereoisomer or salt thereof or of any vehicle, matrix, nano- or micro-particle, or a composition comprising the same. In more specific embodiments, the ARTS mimetic compound used by the method/s of the invention may have the general formula (I) or a pharmaceutically acceptable salt or hydrate thereof including any stereoisomer thereof:

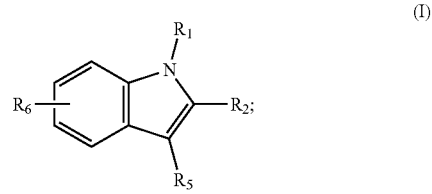

wherein:
$R_1$ is independently selected from H, $C_1$-$C_{12}$ alkyl, $C_2$-$C_{12}$ alkenyl, $C_2$-$C_{12}$alkynyl;
$R_2$ is independently selected from —C(=O)—X—$R_3$, —S(=O)—X—$R_{3'}$;
X is a heteroatom independently selected from N-containing group, O and S;
$R_3$ and $R_{3'}$, independently of each other may be selected independently from H, $C_1$-$C_{12}$ alkyl, $C_2$-$C_{12}$ alkenyl, $C_2$-$C_{12}$alkynyl;
$R_5$ is -L1-$R_7$-L2-$R_8$; L1 and L2, independently of each other, are selected independently from —$(CH_2)_n$—; —NH—C(=O)—$(CH_2)_n$—, —C(=O)—NH—$(CH_2)_n$—; —S—S—$(CH_2)_n$—; —O—$(CH_2)_n$—; —NH—$(CH_2)_n$—; C(=O)—$(CH_2)_n$—; —S—$(CH_2)_n$—; —NH—S(=O)$_n$—$(CH_2)_n$—; n is independently 0 to 5;
$R_7$ is independently selected from straight or branched $C_1$-$C_{12}$ alkylene, straight or branched $C_2$-$C_{12}$ alkenylene, straight or branched $C_2$-$C_{12}$ alkynylene, a ring system containing five to twelve atoms, each optionally substituted;
$R_8$ is independently selected from H, straight or branched $C_1$-$C_{12}$ alkyl, straight or branched $C_2$-$C_{12}$ alkenyl, straight or branched $C_2$-$C_{12}$ alkynyl, a ring system containing five to twelve atoms, each optionally substituted;
$R_6$ is independently selected from H, halogen, CN, $NO_2$, $C_1$-$C_{12}$ alkoxy, straight or branched $C_1$-$C_{12}$ alkyl, straight or branched $C_2$-$C_{12}$ alkenyl, straight or branched $C_2$-$C_{12}$ alkynyl.

In more specific embodiments, the method of the invention may use any of the ARTS mimetic compound/s as defined by the invention. In some particular embodiments, the therapeutic method of the invention may use the ARTS mimetic compound referred to herein as A4 or any derivatives thereof.

As used herein, "proliferative disorder" is a disorder displaying hyper proliferation. This term means cell division and growth that is not part of normal cellular turnover, metabolism, growth, or propagation of the whole organism. Unwanted proliferation of cells is seen in tumors and other pathological proliferation of cells, does not serve normal function, and for the most part will continue unbridled at a growth rate exceeding that of cells of a normal tissue in the absence of outside intervention. A pathological state that ensues because of the unwanted proliferation of cells is referred herein as a "hyper proliferative disease" or "hyper proliferative disorder." It should be noted that the term "proliferative disorder", "cancer", "tumor" and "malignancy" all relate equivalently to a hyperplasia of a tissue or organ. In general, the compositions and methods of the present invention may be used in the treatment of non-solid and solid tumors.

In certain embodiments, the therapeutic method of the invention may be particularly effective for a subject suffering from any one of a pre-malignant condition and carcinoma.

Carcinoma as used herein, refers to an invasive malignant tumor consisting of transformed epithelial cells. Alternatively, it refers to a malignant tumor composed of transformed cells of unknown histogenesis, but which possess specific molecular or histological characteristics that are associated with epithelial cells, such as the production of cytokeratins or intercellular bridges. In terms of solid tumors, this group of cancers may include, among others, carcinomas of the breast, lung, bladder as well as gastric, colorectal, ovarian and uterine carcinomas. The term "carcinoma" refers herein to any tumor tissue derived from putative epithelial cells, or cells of endodermal or ectodermal germ layer during embryogenesis, that become transformed and begin to exhibit abnormal malignant properties.

In more specific embodiments, the therapeutic methods of the invention may be applicable for subjects suffering from a breast carcinoma.

Breast cancer is one of the leading causes of cancer death in women in the Western world. Though current therapies are effective, a considerable population will relapse, rendering the essential need for improved and new avenues of targeted therapies. Gene expression profiling can be used to distinguish breast cancers into distinct molecular subtypes with prognostic significance, based upon phenotypic diversity in biological factors such as histological grade, estrogen receptor (ER) status, progesterone receptor (PgR) status, and HER2/neu expression (HER2).

When presently referring to breast cancer, is meant any type of cancer originating from breast tissue, including ductal and lobular carcinomas. The present context also encompasses genetic or hereditary breast cancers (5-10% of all cases) developing from predisposing mutations in BRCA1 and BRCA2 genes and also other relevant mutations in p53 (Li-Fraumeni syndrome), PTEN (Cowden syndrome), and STK11 (Peutz-Jeghers syndrome), CHEK2, ATM, BRIP1, and PALB2 genes. The present context also encompasses all breast cancer classifications, including those using histopathology (e.g. mammary ductal carcinoma, carcinoma in situ, invasive carcinoma or inflammatory breast cancer), grade (e.g. well differentiated/low grade, moderately differentiated/intermediate grade and poorly differentiated/high grade), stage (0=pre-cancerous, 1-3=regional, 4=metastatic), receptor status (relating to the expression of estrogen receptor ER, PR progesterone receptor and/or HER2/ERBB2 receptor), DNA and protein based classification (using specific mutations or gene expression profiles), and other classification approaches.

As shown in the Examples, ARTS and ARTS mimetic compounds of the invention induce differentiation in pre-malignant cells. Therefore, the methods of the invention may be of particular relevance for early stages of tumor progression. In some embodiments, the method of the invention may be therefore applicable for treating DCIS, UDH and ADH in a subject.

More specifically, Ductal carcinoma in situ (DCIS) is by definition a precursor lesion to invasive ductal carcinoma (IDC). DCIS is a complex pathologic condition in which malignant breast epithelial cells proliferate inside the ducts but do not invade the surrounding stroma. It is generally agreed that the molecular profiles of DCIS and IDC are similar. Although DCIS lesions are more indolent it is estimated that 25 to 50% of cases would progress to invasive cancer over time if left untreated.

In some embodiments, the methods of the invention may be applicable for subjects suffering from ADH. Atypical ductal hyperplasia (ADH), as used herein, is a frequently detected precancerous lesion in the breast. Autopsy studies revealed moderate to severe hyperplasia in over 30% of women aged 45-54 while ADH was detected in 7% of women aged 20-54. ADH is a well-established precursor of breast cancer. Women with ADH have approximately five-fold increased risk of developing breast cancer Lesions with ADH exhibit a proliferation of monotonous normally polarized epithelial cells with complex architecture, including solid, cribriform, and micropapillary patterns. In contrast to ductal carcinoma in situ (DCIS) these hyperplastic lesions are confined and do not fill the entire duct. DCIS is diagnosed when the monotonous proliferation exceeded 3 mm in greatest dimension.

In further embodiments, the methods of the invention may be applicable for subjects suffering from UDH. Usual Duct Hyperplasia (UDH) includes the various patterns of benign epithelial proliferation with little distension of terminal duct-lobular unit, few calcifications and absence of necrosis. Alternative term utilized for UDH is epitheliosis because it can form "tongue-like" projection into ductal lumina, but without the connective core in papillae seen in papillary lesions of other organs. The criteria for diagnosis have been well described by Azzopardi [J. G. Azzopardi, Problems in Breast Pathology, Saunders, 1979]. Two cell types are distinguishable in UDH, epithelial, and myoepithelial, which have divergent differentiation. Immunohistochemical stains (p63, actin, calponin) are useful to detect myoepithelial cells in the lesion. Basal cytokeratins can help distinguish epithelial hyperplasia of usual type (UEH) and clonal proliferations such as DCIS and lobular carcinoma in situ (LCIS).

Still further, it must be appreciated that the methods of the invention may be applicable for any malignant or premalignant condition involving loss of epithelial cell polarity. Non-limiting examples include but are not limited to esophageal squamous cell carcinoma, glioblastoma, head and neck cancer, lung carcinoma, adrenal carcinoma, hepatocellular carcinoma, bladder, squamous cell carcinoma, pancreatic carcinoma, prostate cancer, colorectal cancer, bladder cancer, ovarian carcinoma, colon adenocarcinoma, cervical carcinoma, endometrial carcinoma, cervical carcinoma, melanoma, gastric carcinoma, gastrointestinal testicular carcinoma, brain cancer and the like.

According to another embodiment, as leading to degradation of Bcl-2, the ARTS mimetic compound/s, compositions and methods of the invention may be further applicable for Bcl-2 over-expressing pathological disorders. The phrases "Bcl-2-over-expressing-disorder" and "Bcl-2-mediated disorder" refer to pathological and disease conditions in which a Bcl-2 protein is over-expressed as indicated herein above. Moreover, this term also encompasses conditions in which Bcl-2 plays a role. Such roles can be directly related to the pathological condition or can be indirectly related to the condition. The feature common to this class of conditions is that they can be ameliorated by inhibiting the expression of, activity of, function of, or association with Bcl-2 proteins.

A Bcl-2 over-expressing pathological disorder is meant a disorder characterized by over-expression of Bcl-2 in said subject or in a diseased tissue of said subject as compared to a healthy subject or a healthy tissue of the same subject. It should be noted that the Bcl-2 over-expressing disorder may be caused by chromosomal translocation, hypo-methylation and down regulation of the microRNAs that target Bcl-2.

Still further, malignancy, as contemplated in the present invention may be any one of lymphomas, leukemias, carcinomas, melanomas, myeloma and sarcomas. Therefore, in certain embodiments, the ARTS mimetic compound/s including any stereoisomer or salt thereof, any vehicle, matrix, nano- or micro-particle comprising the same or any of the compositions and methods of the invention may be further relevant for other malignancies such as lymphomas, leukemia, melanomas, myeloma and sarcomas.

Lymphoma is a cancer in the lymphatic cells of the immune system. Typically, lymphomas present as a solid tumor of lymphoid cells. These malignant cells often originate in lymph nodes, presenting as an enlargement of the node (a tumor). It can also affect other organs in which case it is referred to as extranodal lymphoma. Non limiting examples for lymphoma include Hodgkin's disease, non-Hodgkin's lymphomas and Burkitt's lymphoma.

Leukemia refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of abnormal cells in the blood-leukemic or aleukemic (subleukemic).

Melanoma as used herein is a malignant tumor of melanocytes. Melanocytes are cells that produce the dark pigment, melanin, which is responsible for the color of skin. They predominantly occur in skin, but are also found in other parts of the body, including the bowel and the eye. Melanoma can occur in any part of the body that contains melanocytes.

Sarcoma is a cancer that arises from transformed connective tissue cells. These cells originate from embryonic mesoderm, or middle layer, which forms the bone, cartilage, and fat tissues. This is in contrast to carcinomas, which originate in the epithelium. The epithelium lines the surface of structures throughout the body, and is the origin of cancers in the breast, colon, and pancreas.

Myeloma as mentioned herein is a cancer of plasma cells, a type of white blood cell normally responsible for the production of antibodies. Collections of abnormal cells accumulate in bones, where they cause bone lesions, and in the bone marrow where they interfere with the production of normal blood cells. Most cases of myeloma also feature the production of a paraprotein, an abnormal antibody that can cause kidney problems and interferes with the production of normal antibodies leading to immunodeficiency. Hypercalcemia (high calcium levels) is often encountered.

Further malignancies that may find utility in the present invention can comprise but are not limited to hematological malignancies (including lymphoma, leukemia and myeloproliferative disorders), hypoplastic and aplastic anemia (both virally induced and idiopathic), myelodysplastic syndromes, all types of paraneoplastic syndromes (both immune mediated and idiopathic) and solid tumors (including GI tract, colon, lung, liver, breast, prostate, pancreas and Kaposi's sarcoma. More particularly, the malignant disorder may be lymphoma. Non-limiting examples of cancers treatable according to the invention include hematopoietic malignancies such as all types of lymphomas, leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma, as well as for the treatment or inhibition of solid tumors such as tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma.

The methods provided herein involve administration of the ARTS mimetic compound/s of the invention in a therapeutically effective amount. The term "effective amount" as used herein is that determined by such considerations as are known to the man of skill in the art. The amount must be sufficient to prevent or ameliorate tissue damage caused by proliferative disorders. Dosing is dependent on the severity of the symptoms and on the responsiveness of the subject to the active drug, specifically, the antagonist of the invention. Medically trained professionals can easily determine the optimum dosage, dosing methodology and repetition rates. In any case, the attending physician, taking into consideration the age, sex, weight and state of the disease of the subject to be treated, will determine the dose. Optimal dosing schedules can be calculated from measurements of drug accumulation in the body of the patient. Persons of ordinary skill can easily determine optimum dosages, dosing methodologies and repetition rates. In general, dosage is calculated according to body weight, and may be given once or more daily, weekly, monthly or yearly, or even once every 2 to 20 years. Persons of ordinary skill in the art can easily estimate repetition rates for dosing based on measured residence times and concentrations of the compositions and combined composition of the invention in bodily fluids or tissues. Following successful treatment, it may be desirable to have the patient undergo maintenance therapy to prevent the recurrence of the disease state, wherein the ARTS mimetic compound used by the method of the invention is administered in maintenance doses, once or more daily. As use herein "therapeutically effective amount" means an amount of the ARTS mimetic compound/s, a composition comprising the same which provides a medical benefit as noted by the clinician or other qualified observer. Regression of a tumor in a patient is typically measured with reference to the diameter of a tumor. Decrease in the diameter of a tumor indicates regression. Complete regression is also indicated by failure of tumors to reoccur after treatment has stopped.

The present invention provides methods for treating proliferative disorder. The term "treatment or prevention" refers to the complete range of therapeutically positive effects of administrating to a subject including inhibition, reduction of, alleviation of, and relief from, proliferative disorder symptoms or undesired side effects of such proliferative disorder related disorders. More specifically, treatment or prevention includes the prevention or postponement of development of the disease, prevention or postponement of development of symptoms and/or a reduction in the severity of such symptoms that will or are expected to develop. These further include ameliorating existing symptoms, preventing—additional symptoms and ameliorating or preventing the underlying metabolic causes of symptoms.

As used herein, "disease", "disorder", "condition" and the like, as they relate to a subject's health, are used interchangeably and have meanings ascribed to each and all of such terms.

The present invention relates to the treatment of subjects, or patients, in need thereof. By "patient" or "subject in need" it is meant any organism who may be affected by the above-mentioned conditions, and to whom the treatment methods herein described are desired, including humans, domestic and non-domestic mammals such as canine and feline subjects, bovine, simian, equine and murine subjects, rodents, domestic birds, aquaculture, fish and exotic aquarium fish. It should be appreciated that the treated subject may be also any reptile or zoo animal. More specifically, the methods and compositions of the invention are intended for mammals. By "mammalian subject" is meant any mammal for which the proposed therapy is desired, including human, equine, canine, and feline subjects, most specifically humans. It should be noted that specifically in cases of non-human subjects, the method of the invention may be performed using administration via injection, drinking water, feed, spraying, oral gavage and directly into the digestive tract of subjects in need thereof. It should be further noted that particularly in case of human subject, administering of the compositions of the invention to the patient includes both self-administration and administration to the patient by another person.

The invention provides methods for treating proliferative disorders, and further relates to disorders associated or related to cancer. It is understood that the interchangeably used terms "associated" and "related", when referring to pathologies herein, mean diseases, disorders, conditions, or any pathologies which at least one of: share causalities, co-exist at a higher than coincidental frequency, or where at least one disease, disorder condition or pathology causes the second disease, disorder, condition or pathology.

The invention further provides the use of an effective amount of at least one ARTS mimetic compound and any combination thereof in the preparation of a composition for treating, preventing, inhibiting, reducing, eliminating, protecting or delaying the onset of a proliferative disorder in a subject in need thereof.

In yet a further aspect, the invention provides an effective amount of at least one of ARTS or any functional fragment or peptide thereof, at least one ARTS mimetic compound according to the invention, any combination thereof or any composition comprising the same for use in a method for inducing differentiation in a subject in need thereof.

The invention further provides an effective amount of at least one ARTS mimetic compound as defined by the invention, any combination thereof or any composition comprising the same for use in a method for treating, preventing, inhibiting, reducing, eliminating, protecting or delaying the onset of a proliferative disorder in a subject in need thereof.

The inventors have shown that administration of ARTS mimetic compounds of the invention with a BH3-mimetic compound, specifically, ABT-199, enhances the pro-apoptotic effect thereof. Therefore, similar interaction of the ARTS mimetic compounds of the invention with any BH3-containing pro-apoptotic protein, may result in reducing cell survival and proliferation. Thus, according to certain embodiments, the ARTS mimetic compounds of the invention may be further combined with any Bcl-2 family member having a pro-apoptotic activity. Such Bcl-2 pro-apoptotic protein may be for example any one of Bax, Bak, Bnip3, Nix/Bnip3L, Bid, Noxa, Puma and Bad.

Moreover, contacting cells with both, the BH3-mimetic antagonist ABT 199 and the ARTS mimetic compounds of the invention, specifically, A4 had a synergistic effect. Therefore, a combined therapy is further established by the invention.

The term "synergism" refers to interaction of discrete agents (as drugs), such that the total effect is greater than the sum of the individual effects.

Therefore, another aspect of the invention relates to a combined composition comprising a therapeutically effective amount of: (a) any one of at least one BH3 mimetics compound and at least one pro-apoptotic protein member of the Bcl-2 family; and (b) at least one ARTS mimetic compounds of the invention. It should be appreciated that the combined composition of the invention may comprise further therapeutic agent.

In certain embodiments, the combined composition of the invention may comprise at least one BH3-mimetics compound. More specifically, such BH3-mimetic compound may be any one of 4-[4-[[2-(4-chlorophenyl)-4,4-dimethylcyclohexen-1-yl]methyl]piperazin-1-yl]-N-[3-nitro-4-(oxan-4-ylmethylamino)phenyl]sulfonyl-2-1H-pyrrolo[2,3-b]pyridin-5-yloxy)benzamide (ABT-199), 4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (ABT-263), (R)-4-(4-((4'-chloro-[1,1'-biphenyl]-2-yl)methyl)piperazin-1-yl)-N-((4-((4-(dimethylamino)-1-(phenylthio)butan-2-yl)amino)-3-nitrophenyl)sulfonyl)benzamide (ABT-737), 1,1',6,6',7,7'-hexahydroxy-5,5'-diisopropyl-3,3'-dimethyl-[2,2'-binaphthalene]-8,8'-dicarbaldehyde (AT-101), (Z)-2-(2-((3,5-dimethyl-1H-pyrrol-2-yl)methylene)-3-methoxy-2H-pyrrol-5-yl)-1H-indole methanesulfonate (GX15-070), 5-(2-isopropylbenzyl)-N-(4-(2-tert-butylphenylsulfonyl)phenyl)-2,3,4-trihydroxybenzamide (TW-37) or DNA, d(P-thio)(T-C-T-C-C-C-A-G-C-G-T-G-C-G-C-C-A-T, as denoted by SEQ ID NO. 15) (oblimersen sodium), and Venetoclax (Venclexta™) (FDA-approved BH3 mimetic)

In yet another embodiment, the combined composition of the invention may comprise at least one Bcl-2 pro-apoptotic protein. Such protein may be any one of Bax, Bak, Bnip3, Nix/Bnip3L, Bid, Noxa, Puma and Bad.

The phrase "combination therapy" or "adjunct therapy" or in defining use of a compound described herein, specifically, the ARTS mimetic compounds of the invention, and one or more other active pharmaceutical agents, specifically, the BH3-mimetic compounds and/or Bcl-2 pro-apoptotic proteins, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

Another aspect of the invention further relates to a method for treating, inhibiting, preventing, ameliorating or delaying the onset of a proliferative disorder combining the therapeutic use of the ARTS mimetic compounds of the invention with BH3-mimetics compounds or BH3-containing pro-apoptotic protein member of the Bcl-2 family. Thus, such method comprises the step of administering to a subject being treated with at least one BH3-mimetics compound a therapeutically effective amount of at least one ARTS mimetic compounds of the invention.

As noted above, the present invention involves the use of different active ingredients, for example, the ARTS mimetic compounds of the invention, specifically the A4 compound, and at least one BH3-mimetic agent or Bcl-2 pro-apoptotic protein that may be administered through different routes, dosages and combinations. More specifically, the treatment of proliferative diseases and conditions with a combination of active ingredients may involve separate administration of each active ingredient. Therefore, a kit providing a convenient modular format of the ARTS mimetic compounds of the invention and agents required for treatment would allow the required flexibility in the above parameters.

Thus, in another aspect, the invention provides a kit. In some embodiments, the kit of the invention may include at least two separate pharmaceutical compositions that are required enhancing differentiation. According to certain embodiments, the kit of the invention may comprise:
 (a) at least one ARTS mimetic compound as defined by the invention, optionally, in a first dosage form; and
 (b) any one of at least one BH3 mimetics compound, at least one pro-apoptotic protein member of the Bcl-2 family and any combinations thereof, optionally, in a second dosage form.

According to another embodiment, the BH3 mimetics agent used for the kit of the invention may comprise at least one of the following BH3 mimetics compounds or any combinations thereof, 4-[4-[[2-(4-chlorophenyl)-4,4-dimethylcyclohexen-1-yl]methyl]piperazin-1-yl]-N-[3-nitro-4-(oxan-4-ylmethylamino)phenyl]sulfonyl-2-(1H-pyrrolo[2,3-b]pyridin-5-yloxy)benzamide (ABT-199), 4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (ABT-263), (R)-4-(4-((4'-chloro-[1,1'-biphenyl]-2-yl)methyl)piperazin-1-yl)-N-((4-((4-(dimethylamino)-1-(phenylthio)butan-2-yl)amino)-3-nitrophenyl)sulfonyl)benzamide (ABT-737), 1,1',6,6',7,7'-hexahydroxy-5,5'-diisopropyl-3,3'-dimethyl-[2,2'-binaphthalene]-8,8'-dicarbaldehyde (AT-101), (Z)-2-(2-((3,5-dimethyl-1H-pyrrol-2-yl)methylene)-3-methoxy-2H-pyrrol-5-yl)-1H-indole methanesulfonate (GX15-070), 5-(2-isopropylbenzyl)-N-(4-(2-tert-butylphenylsulfonyl)phenyl)-2,3,4-trihydroxybenzamide (TW-37) or DNA, d(P-thio)(T-C-T-C—C-C-A-G-C-G-T-G-C-G-C-C-A-T, as denoted by SEQ ID NO. 15) (oblimersen sodium) and Venetoclax (Venclexta™).

In yet another embodiment, the pro-apoptotic protein member of the Bcl-2 family used for the kit of the invention may comprise at least one of Bax, Bak, Bnip3, Nix/Bnip3L, Bid, Noxa, Puma and Bad.

It should be appreciated that each of the multiple components of the kit may be administered simultaneously.

Alternatively, each of said multiple dosage forms may be administered sequentially in either order.

More specifically, the kits described herein can include a composition as described, or in separate multiple dosage unit forms, as an already prepared liquid topical, nasal or oral dosage form ready for administration or, alternatively, can include the composition as described as a solid pharmaceutical composition that can be reconstituted with a solvent to provide a liquid dosage form. When the kit includes a solid pharmaceutical composition that can be reconstituted with a solvent to provide a liquid dosage form (e.g., for oral administration), the kit may optionally include a reconstituting solvent. In this case, the constituting or reconstituting solvent is combined with the active ingredient to provide liquid dosage forms of each of the active ingredients or of a combination thereof. Typically, the active ingredients are soluble in so the solvent and forms a solution. The solvent can be, e.g., water, a non-aqueous liquid, or a combination of a non-aqueous component and an aqueous component. Suitable non-aqueous components include, but are not limited to oils, alcohols, such as ethanol, glycerin, and glycols, such as polyethylene glycol and propylene glycol. In some embodiments, the solvent is phosphate buffered saline (PBS).

As indicated above, combined therapy provided by the invention encompasses combining of the antagonist of the invention ARTS with ABT 199.

It should be appreciated that any noted that any further BH3 mimetic compound may be used. In some embodiments, ABT-263 may be used. ABT-263 as used herein, is a small molecule that inhibits Bcl-2 and Bcl-XL and marketed by Abbott laboratories under the generic name of Navitoclax. ABT-263 inhibits the anti-intrinsic apoptotic pathway via the BH3 domain. ABT-263 Bcl-2 inhibitor has been demonstrated to be effective against small cell lung cancer xenographs, acute lymphoblastic leukemia and hematologic tumors. ABT-263 appears to most effective in combination therapy with other small molecule inhibitors or with more traditional chemotherapy. Synergistic effects have been documented with YM155, rapamycin, taxanes, etoposide, vincristine, VAP, ritximab, bortezomib and cyclophosphamide. In a panel of pediatric tumors ABT-263 was not effective as a single agent against solid tumors but was highly significant against acute lymphocytic leukemia.

In yet another embodiment, the BH3-mimetic compound may be ABT 737, and therefore, the invention further provide a combined therapy using the ARTS mimetic compounds of the invention, with ABT 263. It should be noted that ABT-737 as used herein is a Bcl-2 inhibitor and is used to mimic the efficiency of molecules targeting the BH3 domain. ABT-737 has been shown to have no effect in tumor types with an over expression of Mcl-1. ABT-737 has been reported as been effecting in the inhibition of hematopoietic cell lines, in overcoming resistance in Burkit's Lymphona, overcoming resistance in solid tumors, in small cell lung carcinoma and also in malignant glioma's. Interestingly, it was shown that ABT-737 appears to as effective in Hypoxia conditions compared to normoixa conditions; which has far reach consequences in the treatment of pancreatic and solid tumor cancer. ABT-737 has been investigated in combination with a wide variety of chemotherapy agents and other small molecule inhibitors. It has been reported that ABT-737 is synergistic when combined with a JAK-1 inhibitor. In addition ABT-737 has sensitized resistant cell lines to the action of GDC-0941, Sorafenib, Fenretinide, gemcitabine, actinomycin D and ABT-263 to name but a few of the combinations tested. To date no phase 1 or phase 2 trials have been reported for the single use of ABT-737 but in combination treatments it has demonstrated potent anti-myeloma activity with Melphalan and Dexamethasone.

The invention provides pharmaceutical compositions comprising an effective amount of the ARTS mimetic compounds of the invention or any combinations thereof with BH3-mimetic compounds or with any pro-apoptotic protein member of the Bcl-2 family. In certain embodiments, the compositions of the present invention can be administered for prophylactic and/or therapeutic treatments. In therapeutic application, compositions are administered to a patient already affected by a proliferative disorder (e.g., carcinoma, specifically carcinoma in organs involved in lumen formation) in an amount sufficient to cure or at least partially arrest the condition and its complications. An amount adequate to accomplish this is defined as a "therapeutically effective dose." Amounts effective for this use will depend upon the severity of the condition and the general state of the patient's own immune system, but generally range from about 0.001 to about 1000 mg/Kg. Single or multiple administrations on a daily, weekly or monthly schedule can be carried out with dose levels and pattern being selected by the treating physician. Additionally, the administration of the compositions of the invention, may be periodic, for example, the periodic administration may be effected twice daily, three time daily, or at least one daily for at least about three days to three months. The advantages of lower doses are evident to those of skill in the art. These include, inter alia, a lower risk of side effects, especially in long-term use, and a lower risk of the patients becoming desensitized to the treatment. In another embodiment, treatment using the compositions of the invention, may be effected following at least 1, 2, 3, 4, 5, 6, 7, 8, 9, 10, 14, 30, 60, 90 days of treatment, and proceeding on to treatment for life.

It should be noted that the treatment of different proliferative conditions may indicate the use of different doses or different time periods, these will be evident to the skilled medical practitioner.

For prophylactic applications, the compositions of the invention may include a prophylactic effective amount of the active ingredient. The term "prophylactically effective amount" is intended to mean that amount of a pharmaceutical composition that will prevent or reduce the risk of occurrence or recurrence of the biological or medical event that is sought to be prevented in a tissue, a system, animal or human by a researcher, veterinarian, medical doctor or other clinician. In prophylactic applications, the compositions of the invention are administered to a patient who is at risk of developing the disease state to enhance the patient's resistance. Such an amount is defined to be a "prophylactically effective dose". In this use, the precise amounts again depend upon the patient's state of health and general level of immunity, but generally range from 0.001 to 1000 mg per dose.

As shown by the Examples, and specifically Example 3, ARTS is cleaved in premalignant cells and is uncleaved in normal cells. Therefore, it should be appreciated that the invention may further encompass a diagnostic and prognostic method that may be also applicable for monitoring of patients treated by any therapeutic compound, for example, the ARTS mimetic compound of the invention. Based on differential detection of ARTS vs. cleaved ARTS, using for example antibodies specific for the N'-terminus (detecting the non-cleaved molecule normal) and antibodies specific for the ARTS C'-terminus. In certain embodiments an increase in cleaved forms of ARTS may indicate that the diagnosed subject is undergoing a malignant process that may involve transition from normal to premalignant phenotype.

All scientific and technical terms used herein have meanings commonly used in the art unless otherwise specified. The definitions provided herein are to facilitate understanding of certain terms used frequently herein and are not meant to limit the scope of the present disclosure.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. As used herein the term "about" refers to +10%.

The terms "comprises", "comprising", "includes", "including", "having" and their conjugates mean "including but not limited to". This term encompasses the terms "consisting of" and "consisting essentially of". The phrase "consisting essentially of" means that the composition or method may include additional ingredients and/or steps, but only if the additional ingredients and/or steps do not materially alter the basic and novel characteristics of the claimed composition or method. Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It should be noted that various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Reagents and Materials
Reagents
Caspase Inhibitors, ARTS Mimetic Molecules and Apoptosis Inducers The caspase inhibitor Q-VD-OPh was purchased from Biovision and resuspended in DMSO as per the manufacturer's instructions.

The pan caspase inhibitor Z-VAD-FMK was purchased from Sigma Aldrich ARTS mimetics small molecules, specifically, A4 and all small molecules used for FIG. 4 were purchased from eMolecules, suspended in DMSO and resuspended in PBS as per the manufacturer's instructions. The apoptotic induction was performed using 1.75 µM STS for the indicated times (Alexis Biochemicals).
Antibodies Antibodies specific for the various proteins were purchased from the indicated companies, and used as instructed. More specifically, the following antibodies were used:
monoclonal anti-ARTS antibody (Sigma, St. Louis);
antibody directed against the unique C-terminus of ARTS (mouse anti ARTS monoclonal antibody (Cat #A4471, Sigma));
polyclonal anti-ARTS antibody (Prosci) directed against the N-terminus region of ARTS (rabbit anti ARTS polyclonal antibody (Cat #3025, Prosci));
antibodies specific for apoptotic proteins: Bcl2 (DB); XIAP (Cat #610716, BD); Caspase-3 (Cat #9662, Cell Signaling).

Actin (Cat #69100, MP Biomedicals) and c-myc (cell signal) were also used.
Experimental Procedures
Cell Lines and Culture in 2D Human breast cancer cell lines MCF-10A (M1) was received from Prof. Israel Vlodavsky (Technion, Israel), MCF10AT1K (M2) and MCF10ACA1 h (M3) were received from Dr. Fred Miller (Barbara Ann Karmanos Cancer Institute). M1 and M2 cells were maintained in DMEM/F12 supplemented with 5% donor horse serum (DHS), 1% sodium pyruvate, 1% L-glutamine, 0.02 µg/ml epidermal growth factor (EGF; Peprotech), 0.01 mg/ml insulin (Sigma), 0.5 µg/ml hydrocortisone (Sigma), 0.1 µg/ml cholera toxin (Sigma) and 1% penicillin-streptomycin at 37° C., 5% $CO_2$ incubator. M3 cells were maintained in DMEM/F12 supplemented with 5% DHS and 1% penicillin-streptomycin at 37° C. and incubated in 5% $CO_2$ incubator.
Three-Dimensional Cell Cultures Cells were harvested from their growth plates using 0.25% trypsin EDTA. Collected cells were cultured in Cultrex® growth factor reduced Basement Membrane Extract (BME: Trevigen, Inc) as follows: An 8 chamber glass slide system (Lab-TEK® II, Naperville, IL) was coated with 60 µl BME [Barkan D. et al., Cancer Research (2008)](protein concentration between 15 mg/ml; thickness~1-2 mm). $5 \times 10^3$ cells per well were re-suspended in DMEM/F12 supplemented with 2.5% DHS and 2% BME and cultured on the coated slides. Slides were incubated at 37° C., 5% $CO_2$ incubator. Cells were re-fed every 4 days. Cell morphology was monitored by light microscopy. Immunofluorescence images were captured by Nikon A1-R confocal laser scanning microscope (Haifa University, Haifa, Israel).
Semi Quantitative RT-PCR RNA was extracted from cells using Total RNA Mini Kit (Bio-Rad) according to the manufacturer's instructions. Equal amounts of total RNA (1 µg) were used as template for first-strand synthesis with oligo dT primers (High Capacity RNA-to-cDNA Kit; Applied Biosystems) in 20 µl volume and the resulting first-strand cDNA was used for qPCR reactions.
qPCR Reaction A reaction mixture containing 300 ng cDNA, 10 µl PCR Dream Taq Mix and 4 µl of 5 µM primers (F+R) was assayed in a Gradient Thermal Cycler PCR system (MJ Mini™). The 20 µl reaction mixtures were heated to 95° C. for 3 minutes, and 36 PCR cycles were carried out as follows: Denaturation at 95° C. for 30 seconds, annealing at 58° C. for 30 seconds, and extension at 72° C. for 30 seconds. The reaction was heated at 72° C. for 10 minutes and subsequently cooled to 4° C. indefinitely. Electrophoresis of the samples was carried out on a 1.5% agarose gel.

The following PCR primers were used: For ARTS:

```
Forward:
5'-GAGACGAGAGTGGCCTGAACCGA-3',
as denoted by SEQ ID NO. 11;

Reverse,
5'-AACAGGAACCTGTGACCACCTGC-3'
as denoted by SEQ ID NO. 12;

For human GAPDH:
Forward,
```

-continued
```
5'-ATGGGGAAGGTGAAGGTCG-3',
as denoted by SEQ ID NO. 13;

Reverse,
5'-GGGGTCATTGATGGCAACAATA-3',
as denoted by SEQ ID NO. 14;
```

Transient Transfections of MCF-10 A Cell Lines

The cells were transfected with either 6-MycTag-ARTS in pCS2 or sport-ARTS in pCMV plasmid, that was produced in Sarit Larisch lab as described previously (Larisch & Yi 0.2000). For the transfection the Turbofect (Fermentas) was used with concentration of 0.1 µg/1 DNA for 6-MycTag-ARTS and sport-ARTS plasmid.

Stable Transfections of 293T Cells with Bcl-2-Cherry Reporter pcDNA-3.1 vector carrying Bcl2 with an mCherry fusion c' terminus fluorescent tag and neomycin (G418) resistance sequences was transfected into HEK 293T cells using Turbofect (Fermentas). Cells were then treated with G418, and resistant fluorescent cells were further sorted and isolated by FACS-sorter. Mono-clones of the stably expressing Bcl2-mCherry and G418 resistance were propagated and used for the experiments.

Western Blot Analysis

The cells were lysed in WCE (whole-cell extract) buffer [251 mM Hepes, pH 7.7, 0.3M NaCl, 1.5 mM MgCl2, 0.2 mM EDTA, 0.1% Triton X-100, 100 µg/ml PMSF and protease inhibitor cocktail (Roche, 1:100 dilution)]. 100 µg of total cell protein, measured with the Bio-Rad Protein Assay kit, were separated by SDS-PAGE (12%) followed by transfer for 2 h on to a nitrocellulose membrane. The membrane was blocked with 5% (w/v) non-fat dried skimmed milk powder in PBS supplemented with 0.05% Tween20 (PBS-T) for 1 hour at room temperature (R.T). Membrane was then probed with primary antibody at 4° C. overnight. Next, the membrane was incubated with the appropriate HRP-conjugated secondary antibody, for 1 hour at R.T. and washed 15 min×3 with PBS-T. WesternBright ECL (Advansta) was added to the membrane for 2 min and analyzed using ImageQuant LAS-4000 analyzer (GE Healthcare Life Sciences) & "ImageQuant LAS-4000" software (GE Healthcare Life Sciences). Densitometry analysis was performed using ImageQuant total lab 7 (GE Healthcare Life Sciences), image analysis software.

Immunofluorescence Staining in 3D Culture

The following two protocols were used for cells staining:

Laminin5 immunofluorescence staining: was performed as described by Barkan et al., [*Cancer Research* (2008)]. Briefly, cells cultured in 8 well chamber glass slides in 3D BME, as described above. The cultured cells were fixed and permeabalized for 5 minutes with 4% Paraformaldehyde (PFA) containing 5% sucrose and 0.2% Triton X-100, and re-fixed for an additional 25 minutes with 4% PFA containing 5% sucrose. The cells were washed for 10 minutes with PBS and an additional 10 minutes with PBS containing 0.05% Tween 20 (Sigma). Fixed cells were blocked with 3% BSA in PBS for 1 hour and incubated overnight at 4° C. with primary antibody (Rabbit polyclonal antibody to Laminin-5 (1:200)). The cells were washed three times with PBS for 15 minutes each, and incubated for 1 hour with rabbit conjugated to Alexa Fluor®647 (Invitrogen), washed as above and mounted with VECTASHIELD mounting medium with 4',6-diamidino-2-phenylindole (DAPI). For F-actin staining cells were incubated over night with Alexa-Fluor®488 Phalloidin (1:40) (Molecular Probes) washed three times with PBS for 15 minutes each, and mounted with VECTASHIELD mounting medium with DAPI. The slides were imaged using Nikon A1-R confocal laser scanning microscope (Haifa University, Haifa, Israel).

a. cis-Golgi protein GM130 immunofluorescence staining; was performed as a modification of Muthuswamy et al. (2001). Briefly, M1 and M2 cells grown in 3D culture, as described above, were fixed for 25 minutes at room temperature with 4% PFA containing 5% sucrose. Fixed structures were washed three times in PBS:Glycine (130 mM NaCl, 7 mM Na$_2$HPO$_4$, 3.5 mM NaH$_2$PO$_4$, 100 mM glycine) for 15 minutes each and permeabalized with 0.5% Triton X-100 in PBS for 5 minutes at room temperature and washed three times in IF buffer (130 mM NaCl, 7 mM Na$_2$HPO$_4$, 3.5 mM NaH$_2$PO$_4$, 7.7 mM NaN3, 0.1% BSA, 0.2% Triton X-100, 0.05% Tween 20) for 10 minutes each. The washed structures were blocked in IF buffer plus 10% donkey serum for 1 hour at room temperature. Primary antibody (GM 130; Abcam) was diluted in blocking buffer (1:500) and incubated overnight at 4° C. with primary antibody. Unbound primary antibody was removed by washing three times in IF buffer for 20 minutes each. Donkey anti rabbit secondary antibodies coupled with Alexa Fluor®647 (Invitrogen) was diluted in IF buffer containing 10% donkey serum and incubated for 1 hour. Unbound secondary antibody was washed as described above. Sides were mounted with VECTASHIELD mounting medium with DAPI. The slides were imaged using Nikon A1-R confocal laser scanning microscope (Haifa University, Haifa, Israel).

Proliferation Assay

The CellTiter 96 AqueousOne Solution of cell proliferation assay kit (Promega) was added to the wells for 2 hours to measure cell proliferation according the manufacturer's instructions. The absorbance was recorded at 490 nm.

MicroScale Thermophoresis (MST)

His-tagged Bir3 (XIAP 252-350) was expressed and purified as previously described (Reingewertz et al, 2011). The purified Bir3 was labeled with the Monolith NT™ Protein Labeling Kit RED according to the supplied labeling protocol.

340 nM of fl-labeled Bir3 was titrated with A4 compound in 1:1 dilutions beginning at 500 µM, in a 25 mM Tri-Sodium acetate buffer pH 5.6, 2% DMSO and 0.05% Tween 20. The measurements were performed on a NanoTemper Monolith instrument.

Proteasome-Mediated Degradation Studies

T47D breast cancer cells: $1*10^6$ T47D cells were seeded on a 10 cm plate in RPMI and were propagated to 80% confluence. Cells were treated for 1 hour with either DMSO (control) or 30 µM A4 together with 20 µM MG-132 (proteasome inhibitor) or without MG-132. Cells were lysed total protein was extracted and subjected to western blotting with the indicated antibodies.

HeLa cervical cancer cells: $1.5*10^6$ HeLa cells were seeded on a 10 cm plate in DMEM and were propagated to 80% confluence. Cells were treated for 2 hour with either DMSO (control) or 30 µM A4 together with 20 µM MG-132 (proteasome inhibitor) or without MG-132. Cells were lysed total protein was extracted and subjected to western blotting with the indicated antibodies.

Cell-Killing Assay-Oncolead Tumor Cell-Line Screen

Oncolead library of 94 different cancer cell-lines spanning over 18 human tissues was used for screening. Briefly, cells are treated series of 6 dilutions of a compound for 72 hours (compound is replenished daily). After 72 hours cells are fixed (living cells are attached to the plate) then washed (removes dead and dying cells). Cells are then stained with a dye (Sulforhodamine B-SRB) that dyes all proteins in a purple color, which is measure by a plate reader and provides a reliable quantification of living cells.

The number of cells treated with the ARTS mimetic compound A4, is compared to the number of cells treated with DMSO (solvent). IC value is calculated by the number of cells after 72 h treatment at concentration of compound (Ti), divided by the number of cells after 72 h treatment with DMSO (C).

IC-50 is the value calculated from the dose response plot, which is the concentration of the compound that has 50% decrease of the IC.

To compare between cell-lines, the IC-50 of each cell-line is compared to mean IC-50 of all cell-lines, using Z-score. Z-score is the number of standard deviations of the IC-50 of a single cell-line from the mean IC-50 of all cells-lines. Therefore, Z-score=0 in the mean IC-50 of all cell-lines; Z-score>0 represents resistant cell-lines; Z-score<0 represents sensitive cell-lines.

Statistical Analysis

Date are presented as mean±S.D. experiment were analyzed by Student's t-test. Statistical significance was defined as P≤0.05 (*), P≤0.01 (), and P≤0.001 (*).

Example 1

Screening for ARTS Mimetic Small Molecules

Figure 1:
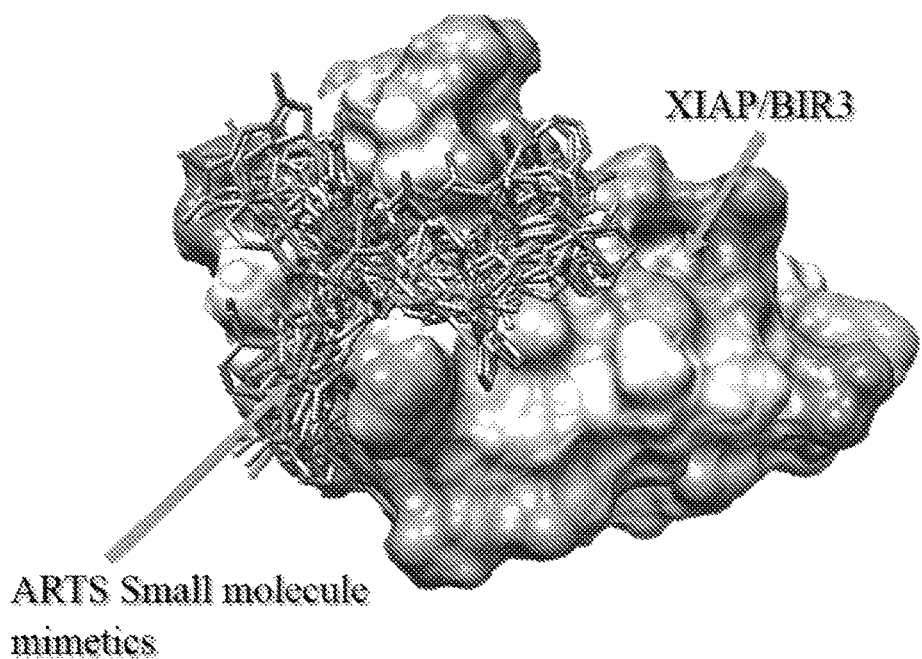
FIG. 1. Docking Site of ARTS Mimetic Compounds within BIR3/XIAP

The inventors have previously shown that ARTS induces apoptosis by interaction of its unique C-terminal domain with distinct binding sequence within BIR3/XIAP. In an attempt to screen for further small molecules for cancer therapy, an "in silico" screen was done by "BioSolvit" to look for ARTS mimetic small molecules that fit into ARTS binding site within the XIAP molecule. As illustrated by FIG. 1, about 100 candidate molecules were revealed. FIGS. 2 and 3 present the structure of one of the candidate molecules, referred to herein as "A4" (or, A4, A4 compound and the like) located within the binding site and the interactions of said candidate compound with residues Phe270 and Thr274 of the BIR3/XIAP.

The candidate molecules were next subjected to functional assays, examining their ability to induce apoptosis. Therefore, the expression of several apoptotic markers was examined in A375 human melanoma cells exposed to 20 µM of each of the candidate compounds. As shown in FIG. 4A, the A4 small molecule clearly reduced the levels of the anti-apoptotic proteins XIAP and Bcl-2. No effect on cCaspase or c-PARP was shown. Similar results were also demonstrated for different concentrations (5-40M) of the effective candidate A4 (not shown).

To further evaluate the mechanism underlying the down regulation of XIAP and Bcl-2 protein levels induced by ARTS mimetic A4 molecule shown herein, the optional involvement of proteasome mediated degradation has been next evaluated by examining the effect of the A4 molecule in the presence or the absence of a proteasome inhibitor. As can be seen in both FIGS. 4B and 4C, the effect of A4 molecule was reversed in the presence of a proteasome inhibitor. Specifically, as shown in FIG. 4B, following 1 hour incubation of T47D breast cancer cells with 30 µM A4, there was a specific decrease in XIAP levels but not cIAP1. In addition, A4 caused a decrease in Bcl-2 levels. This decrease was the result of Ubiquitin-proteasome mediated degradation as addition of MG-132, proteasome inhibitor at 20 µM restored the levels of both XIAP and Bcl-2. Similarly, FIG. 4C shows that following 2 hour incubation of HeLa cervical cancer cells with 30 µM A4 there was a specific decrease in XIAP levels but not cIAP1. In addition, A4 caused a decrease in Bcl-2 levels. This decrease was the result of Ubiquitin-proteasome mediated degradation as addition of MG-132, proteasome inhibitor 20 µM restored the levels of both XIAP and Bcl-2.

These results show that as short as 1 hour or 2 hour after treatment with A4 there is a proteasome-mediated degradation of both two major anti-apoptotic proteins; XIAP and Bcl-2. These results clearly indicate that the observed downregulation of XIAP levels and Bcl-2 levels is mediated by the ubiquitin—proteasome machinery (UPS).

To further characterize the A4 candidate, MicroScale Thermophoresis (MST) was used to evaluate the binding of the A4 compound to fluorescently labeled Bir3 (His-tagged) domain of XIAP, residues 252-350. The calculated Kd from the measurement is 46.1±3.65 µM, however, tendency of the A4 to aggregate may explain this rather week interaction. Microscale thermophoresis (MST) is a technology for the interaction analysis of biomolecules. Microscale thermophoresis is the directed movement of particles in a microscopic temperature gradient. Any change of the hydration shell of biomolecules due to changes in their structure/conformation results in a relative change of the movement along the temperature gradient and is used to determine binding affinities. MST allows measurement of interactions directly in solution without the need of immobilization to a surface (immobilization-free technology).

To further characterize the A4 candidate, the MSTtechnology described above was used to evaluate the binding of the A4 compound to recombinant GST-tagged XIAP, as presented in FIG. 4D. The calculated Kd from the measurement is 34.6±2.48 µM. These results show that A4 binds directly to BIR3 domain in XIAP and to the whole XIAP.

The ARTS mimetic A4 candidate was further evaluated functionally, using several malignant cells models as detailed in the following examples.

Example 2

Differential Expression of ARTS, Bcl2 and XIAP in Different Stages of Tumor Progression in the MCF10 Model System To test whether ARTS play a role in tumor progression, the MCF-10 model system was next used by the inventors. More specifically, the expression of ARTS and the anti-apoptotic proteins XIAP and Bcl-2 regulated by ARTS was examined in three isogenic cell lines derived from the breast epithelial MCF-10 model system, M1 (MCF10A), M2 (MCF10AT1k) and M3 (MCF10CA1 h), that represent normal, premalignant epithelium and high grade malignant cells, respectively.

As surprisingly shown in FIG. 5A, ARTS mRNA levels were clearly increased during tumor progression and ARTS expression was highest in M3 cells. Western blot analysis performed using an antibody recognizing ARTS C' terminal domain (ARTS C' terminus) confirmed a significant increase in the protein levels of ARTS in M1 through M3 (FIGS. 5B and 5C).

However, when antibodies recognizing the N' terminal domain of ARTS were used (ARTS N' terminus), a significant decrease in ARTS levels was observed upon transformation of the cells from M1 to M2 and M3 cells (FIGS. 5B and 5D). Furthermore, Bcl-2 expression increased significantly in M2 cells compared to M1 cells (FIGS. 5B and 5E) and a significant increase in XIAP expression levels in both transformed M2 and M3 cells was evident, specifically when compared to M1 cells (FIGS. 5B and 5F). Given these results, the inventors hyothesized that structural changes occurring at the N-terminal part of ARTS may result in decreased binding of an antibody directed against this N' terminal region of ARTS. These findings further suggest that the transition from normal to premalignant cells may be accompanied and affected by structural changes in ARTS.

Example 3

Cleavage of ARTS in Pre-Malignant and Malignant Cells During Malignant Transformation The inventors next explored the possibility that post translation modification of the N-terminal part of ARTS occur during transformation of M1 cells. More specifically, the inventors tested whether the decreased binding of the ARTS N' term antibody, shown in FIGS. 5B and 5D, is a result of ARTS cleavage at its N' terminal domain. Therefore, all three-cell lines where transfected either with an empty vector or with a vector encoding 6myc-ARTS (ARTS fusion protein with 6× myc tags at its N'-terminal domain). Detection of the 6-Myc large tag at the N-terminal domain of ARTS using a myc specific antibody facilitates detection of a small portion of ARTS cleaved form, when cleavage occurs at its N-terminus (wt. ARTS predicted size is 28K-30 Kda whereas 6myc-ARTS—47 Kda).

The results presented in FIG. 6A, 6B clearly indicate that while no cleavage of 6myc-ARTS is seen in the non-malignant M1 cell line, both malignant M2 and M3 cell lines exhibit several possible cleavage forms of ARTS. These results thus suggest possible modifications of ARTS at its N' terminal domain upon transformation of M1 to M2 and M3 cells. Furthermore, although ARTS was exogenously expressed in M2 and M3 cells, the overall level thereof as detected by ARTS C-' term antibody, was equivalent to its level in the control vector cells. In contrast, M1 cells displayed a significant increase in total ARTS levels when transfected with the ARTS-6myc vector compared to the control vector cells. These results further support the observation that ARTS is cleaved only in the transformed MCF10 cells.

The inventors next examined whether caspases mediate the cleavage of the N'-terminal part of ARTS. To this end, the inventors transfected M2 cells with 6myc-ARTS and cells were either untreated or treated with a pan inhibitor of all caspases, Q-VD. The results presented in FIG. 7 demonstrate that upon inhibition of caspases with Q-VD, there was an increase in the uncleaved 6myc-ARTS and decrease in the cleaved 6-myc ARTS, respectively (FIG. 7A-7B). These results therefore suggest that in premalignant cells, caspases mediate ARTS N'-terminus cleavage. Previous results of the present inventors showed that ARTS act as an adaptor by binding XIAP via its C'-terminus and Bcl-2 via its N'-terminus thereby leading to Bcl-2 degradation. Importantly, upon treatment with Q-VD, Bcl-2 levels significantly increased in M2 cells transfected with 6myc-ARTS, further suggesting that by keeping the myc tag bound to the N'-terminal part of ARTS, binding of Bcl-2 to ARTS N'-terminus was prevented thereby eliminating Bcl-2 degradation (FIG. 7C). In contrast, no change in XIAP levels was shown (FIG. 7D).

Example 4

Characterization of M1-M3 Cells in 3D Basement Membrane Extract (BME) System

Unlike monolayer cultures, mammary epithelial cells are grown in three dimensions and recapitulate numerous features of breast epithelium in vivo, including the formation of acini-like organoids characterized by a hollow lumen [Debnath et al., (2003)]. Disruption of this intact well-ordered tissue architecture and uncontrolled cell growth are the hallmark of neoplastic transformation [Bissell et al., (2001)] (see FIG. 8A). These have prompted the inventors to characterize the morphological change of MCF10 model system in 3D culture system. The MCF10 model system cells were cultured in 3D BME system overlaid with condition media of DMEM/F12 supplemented with 2.5% DHS).

As shown in FIGS. 8B and 8C, after 7 days, normal M1 cells showed acini-like structures containing a single layer of polarized cells that surrounds a hollow lumen, similar to normal acini. The organoids of M2 and M3 cells were larger than the organoids developed by M1 cells, indicating an increased proliferation. Pre-malignant M2 cells formed organoids structures with epithelial cell occupying the luminal space. Furthermore, these organoids were larger and some lost their polarity, when compared to normal M1 cells. The M3 cells formed large hyper-proliferative cell aggregates characterized by loss of polarity of the organoids with no apparent lumen (see FIG. 8B, 8C).

Example 5

Over-Expression of ARTS in Pre-Malignant M2 Cells Leads to Reversion of the Cells to a Normal-Like Phenotype Apicobasal polarization followed by apoptosis of cells occupying the luminal space of M1 cells occurs during normal morphogenesis of M1 cells when cultured in the 3D BME system (Muthuswamy et al., 2001). Here the inventors examined whether expression of the pro-apoptotic protein ARTS will promote luminal clearance of organoids structure of the pre-malignant cells M2. Therefore, the effect of over-expression of ARTS in M2 cells transiently transfected with pCMV-sport-ARTS plasmid, was tested. To optimize time for cell seeding in the 3D culture system, the inventors carried out course of transient expression of ARTS. The inventors further performed time course for the developed organoids. As shown in FIG. 9A, an increased expression of ARTS was detected after 48 hours of transfection. After 5 days of seeding, initial stages of polarization and lumen formation was observed in M2-ARTS organoids compared to M2-vector organoids. After 7 days of seeding, a typical hollow lumen surrounded by well-polarized layer of cells was detected in M2-ARTS organoids, similar to M1 acini (FIG. 9B). These results clearly suggest that expression of ARTS in pre-malignant cells promotes the reversion of M2 organoids to a normal-like phenotype.

Example 6

The Effect of ARTS Mimetic Small Molecule A4 on Pre-malignant Cells

Acini-like organoids forms hollow lumen after 10 to 12 days in 3D culture system and remain hollow thereafter (Muthuswamy et al., 2001). Plasmids introduced by transient cell transfection are only expressed for a limited period of time, as they are not integrated into the genome and therefore may be lost by environmental factors and cell division. Therefore, the inventors next examined whether introduction of small-molecules may mimic ARTS function, specifically in inducing lumen formation and reversion of pre-malignant cells to a normal-like phenotype. The inventors thus tested initially the effect of the ARTS mimetic small molecule A4 on induction of apoptosis in 2D culture.

As shown in FIG. 10A-10B, treatment of M2 cells with the A4 molecule for 24 and 48 hours resulted in a decrease in cell proliferation. However, only low amount of apoptotic cells was apparent. Therefore, A4 molecule in these mammary epithelial cells induces decrease in cell proliferation.

Example 7

ARTS Mimetic Small Molecule A4 Promotes Apical Polarization, Lumen Formation and Reversion of Malignant Cell Phenotype To further determine whether the mimetic ARTS small molecule A4 will promote the reversion of M2 cell to a normal like phenotype similarly to ARTS as demonstrated in FIG. 9B, the inventors treated M2 cells in 3D BME culture system, with different concentrations of the A4 molecule for 7 days. FIG. 12 (12A, 12B) clearly shows that similarly to M1 acini, initiation of apical staining of GM130 and basal staining of Laminin 5 (reflecting apicobasal polarization, illustrated in FIG. 11), was apparent in M2 organoids treated with the A4 molecule (40 µM). These results indicate that prior to the formation of a bona fide lumen, the ARTS mimetic small molecule A4 promotes apicobasal polarity in premalignant M2 cells as occurs during normal morphogenesis of MCF-10 A cells in the 3D BME culture.

To further characterize the effect of the ARTS mimetic A4 molecule on induction of M2 organoids polarization and initiation of lumen formation, the inventors tested the effect of prolonged treatment with said A4 small molecule. As clearly shown in FIG. 13 (13A, B and 13C), treatment with A4 for 14 days led to apicobasal polarization of M2 organoids followed by luminal formation (similar to M1 acini). More importantly, treatment of M2 organoids with A4 induced conversion thereof to a normal-like phenotype characterized by formation of a normal acini-like structure reminiscent of the normal mammary gland. Furthermore, the presence of ductal-like tree structures was also evident. These results clearly indicate that prolonged treatment of premalignant M2 organoids with the ARTS mimetic A4 molecule induce differentiation reverting the cells to normal-like acini.

Example 8

The ARTS Mimetic Small Molecule A4 Synergizes with BH3-Mimetic Compound

To further evaluate the therapeutic potential of the ARTS mimetic A4 molecule, combination thereof with known BH-3 mimetic compound was next examined using 293 cells stably expressing Bcl-2 cherry reporter. FIG. 14, clearly show a synergetic effect when the ARTS mimetic compound was combined with the BH3 mimetic compound ABT199. These results therefore demonstrate the feasibility of a combined treatment of the ARTS mimetic compound A4 and Bcl-2 inhibitors.

Example 9

The Killing Effect of the ARTS Mimetic Small Molecule A4 in Cancer Cell Lines

To further evaluate the ARTS mimetic compound of the invention as a potential anti-cancerous drug, a library of 94 different cancer cell-lines spanning over 18 human tissues was next used to assess the effect of the A4 compound on the viability of a verity of tumor cell-lines, whether it is growth inhibition or death. Table 1 presents the Z score analysis of the IC50 values and shows that variety of cell lines, specifically, cancerous cell lines of different tissue origin that include placenta, kidney, skin, liver, pancreas, muscle, lungs, bone, hematological cancers, colon, bladder prostate, ovary, breast and cervical carcinoma are sensitive (negative z-score) to the ARTS mimetic compound of the invention A4, that leads to apoptosis of the cells. Resistance (positive z-score) was evident in most brain tumors cells and cell lines of a normal healthy origin.

TABLE 1

| Cell line | Cell origin | z-score |
|---|---|---|
| 5637 | bladder | −0.5195 |
| CLS439 | bladder | 0.2401 |
| EJ28 | bladder | 0.3445 |
| J82 | bladder | 0.7141 |
| T24 | bladder | 0.2436 |
| UMUC3 | bladder | −1.1449 |
| MG63 | bone | −0.2723 |
| MHHES1 | bone | −0.6342 |
| RDES | bone | 1.1753 |
| SAOS2 | bone | 0.0704 |
| U2OS | bone | −0.4781 |
| SF268 | brain | 0.6943 |
| SF295 | brain | 0.6281 |
| SKNAS | brain | 1.1400 |
| SKNSH | brain | −0.2835 |
| SNB75 | brain | 1.1399 |
| U87MG | brain | 0.6890 |
| BT20 | breast | 2.0124 |
| HS578T | breast | 0.6665 |
| JIMT1 | breast | −0.0134 |
| MCF7 | breast | −1.0178 |
| MDAMB231 | breast | 0.8010 |
| MDAMB436 | breast | −0.0011 |
| MDAMB468 | breast | −0.3252 |
| MT3 | breast | −1.4352 |
| SKBR3 | breast | 0.2483 |
| C33A | cervix | −0.5498 |
| CASKI | cervix | 0.3437 |
| HELA | cervix | 0.5381 |
| CACO2 | colon | 0.2941 |
| COLO205 | colon | 0.0701 |
| COLO678 | colon | 1.6130 |
| DLD1 | colon | 0.3223 |
| HCT116 | colon | 1.0221 |
| HCT15 | colon | −0.8139 |
| HT29 | colon | −3.1291 |
| LOVO | colon | −0.4232 |
| SW620 | colon | 0.8557 |
| HT1080 | connective tissue | 0.0913 |
| GRANTA-519 | hematological | 0.0388 |
| HL-60 | hematological | −0.7180 |
| K-562 | hematological | −0.5500 |
| KASUMI-1 | hematological | 0.2865 |
| L-363 | hematological | −1.3545 |
| MINO | hematological | −0.2474 |
| MV4-11 | hematological | −0.7713 |
| PBMC | hematological | 4.3886 |
| RAMOS | hematological | −0.1507 |
| SU-DHL-10 | hematological | 0.0690 |
| SU-DHL-6 | hematological | −0.9611 |
| THP-1 | hematological | 0.6831 |
| WSU-NHL | hematological | −0.9876 |
| 786O | kidney | −0.2951 |
| ACHN | kidney | −0.4129 |
| CAKI1 | kidney | 0.2956 |
| HEK293 | kidney | −2.1681 |
| UO31 | kidney | −0.2304 |
| HEPG2 | liver | 0.1634 |
| PLCPRF5 | liver | −0.9269 |
| SKHEP1 | liver | 0.3196 |
| A549 | lung | −0.3954 |
| CALU6 | lung | 0.6180 |
| IMR90 | lung | 0.6305 |
| NCIH292 | lung | 1.1407 |
| NCIH358M | lung | −0.8422 |
| NCIH460 | lung | −0.3418 |
| NCIH82 | lung | −1.0455 |
| A204 | muscle | −1.0965 |
| A673 | muscle | −0.1741 |

TABLE 1-continued

| Cell line | Cell origin | z-score |
|---|---|---|
| HS729 | muscle | 1.2040 |
| RD | muscle | 1.1577 |
| TE671 | muscle | −1.2596 |
| A2780 | ovary | −2.8059 |
| EFO21 | ovary | 0.4746 |
| IGROV1 | ovary | 0.2766 |
| OVCAR3 | ovary | 0.3687 |
| OVCAR4 | ovary | 0.7674 |
| SKOV3 | ovary | 1.4825 |
| ASPC1 | pancreas | 1.0560 |
| BXPC3 | pancreas | 0.5706 |
| MIAPACA2 | pancreas | −0.4747 |
| PANC1 | pancreas | −1.0696 |

TABLE 1-continued

| Cell line | Cell origin | z-score |
|---|---|---|
| PANC1005 | pancreas | −0.4386 |
| JAR | placenta | −0.9307 |
| JEG3 | placenta | −0.5263 |
| 22RV1 | prostate | −0.8474 |
| DU145 | prostate | 0.3419 |
| PC3 | prostate | 0.5877 |
| A375 | skin | −0.6979 |
| A431 | skin | 0.5492 |
| MDAMB435 | skin | −0.4875 |
| SKMEL28 | skin | 0.5555 |
| SKMEL5 | skin | −0.7441 |
| SKLMS1 | uterus | 1.0090 |

The invention claimed is:

1. A method for inducing differentiation and/or apoptosis in a cell, wherein said method comprises the step of contacting said cell with an effective amount of at least one ARTS mimetic compound, any combination thereof any vehicle, matrix, nano- or micro-particle, or any composition comprising said at least one ARTS mimetic compound, wherein said ARTS mimetic compound having the general formula (I) or a pharmaceutically acceptable salt or hydrate thereof or any stereoisomer or salt thereof:

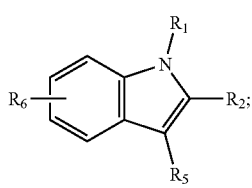

(I)

wherein:
 $R_1$ is independently selected from H, $C_1$-$C_3$ alkyl;
 $R_2$ is independently selected from —C(=O)—X—$R_3$, —S(=O)—X—$R_{3'}$;
 X is a heteroatom independently selected from O;
 $R_3$ and $R_{3'}$, independently of each other may be selected independently from H, $C_1$-$C_3$ alkyl;
 $R_5$ is -L1-$R_7$-L2-$R_8$;
 L1 and L2, independently of each other, are selected independently from —(CH$_2$)$_n$; —NH—C(=O)—(CH$_2$)$_n$—, —C(=O)—NH—(CH$_2$)$_n$—; —S—S—(CH$_2$)$_n$—; —O—(CH$_2$)$_n$—; —NH—(CH$_2$)$_n$—; C(=O)—(CH$_2$)$_n$—; —S—(CH$_2$)$_n$—; —NH—S(=O)$_n$—(CH$_2$)$_n$—;
 n is independently 1 to 3;
 $R_7$ is a carbocyclic ring or a heterocyclic ring;
 $R_8$ is a mono cyclic ring system having 5 to 12, optionally substituted with at least one of OH, CF$_3$, halogen, —COOH, —NH$_2$, CN, $C_1$-$C_3$alkyl; and
 $R_6$ is independently selected from H, halogen, CN, NO$_2$, $C_1$-$C_3$ alkoxy, straight or branched $C_1$-$C_3$ alkyl.

2. The method according to claim 1, wherein said ARTS mimetic compound of the general formula (I) is at least one of:
 (a) wherein $R_1$ is H;
 (b) wherein $R_2$ is —C(=O)—X—$R_3$;
 (c) wherein X is O;
 (d) wherein L1 and L2 independently selected independently from each other from —NH—C(=O)—(CH$_2$)$_n$—, —(CH$_2$)$_n$—; and
 (e) wherein $R_6$ is independently selected from the group consisting of H, halogen, CN, NO$_2$.

3. The method according to claim 1, wherein said ARTS mimetic compound including any stereoisomer or salt thereof having the general formula of:

(a) formula (II)

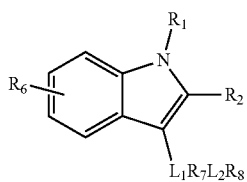

wherein $R_1$, $R_2$, $R_6$, $R_7$, $R_8$, L1 and L2 are as defined in claim 1; or (b) formula (III)

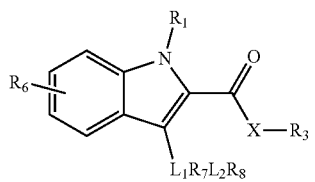

wherein $R_1$, $R_3$, $R_6$, $R_7$, $R_8$, L1 and L2 are as defined in claim 1; or (c) formula (IV)

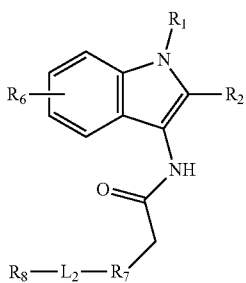

wherein $R_1$, $R_2$, $R_6$, $R_7$, $R_8$, and L2 are as defined in claim 1; or (d) formula (VI)

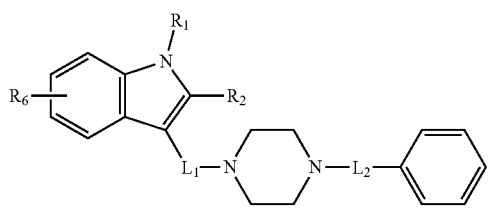

wherein $R_1$, $R_2$, $R_6$, L1 and L2 are as defined in claim 1.

4. The method according to claim 3, wherein said compound is 3-[2-(4-Benzyl-piperazin-1-yl)-acetylamino]-5-chloro-1H-indole-2-carboxylic acid methyl ester, having the structure:

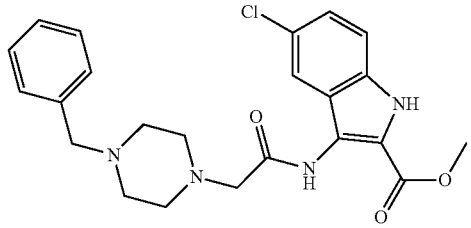

including any stereoisomer thereof or salt thereof.

5. The method according to claim 1, wherein said cell is a premalignant or malignant cell, and wherein said method is for inducing or promoting at least one of: cell differentiation, apicobasal polarization and initiation of lumen formation thereby restoring a normal-like phenotype of a tissue comprising said cell.

6. The method according to claim 5, for inducing differentiation of pre-malignant or malignant epithelial cell/s.

7. The method according to claim 6, wherein said cell is any one of a premalignant epithelial breast cell and an epithelial breast carcinoma cell, and wherein said ARTS mimetic compound induces formation of acini-like organoids characterized by a hollow lumen by said epithelial breast cells reminiscent of the normal breast tissue.

8. The method according to claim 5, wherein said cell is a pre-malignant or malignant epithelial cell in a subject, wherein said method is for inducing differentiation of pre-malignant or malignant epithelial cells in said subject in need thereof, and wherein said contacting is by administering to said subject a therapeutically effective amount of said ARTS mimetic compound.

9. A method for treating, inhibiting, reducing, eliminating, protecting or delaying the onset of a proliferative disorder in a subject in need thereof, said method comprises administering to said subject a therapeutically effective amount of at least one ARTS mimetic compound any vehicle, matrix, nano- or micro-particle or any composition comprising the same, said ARTS mimetic compound having the general formula (I) or a pharmaceutically acceptable salt or hydrate thereof including any stereoisomer thereof

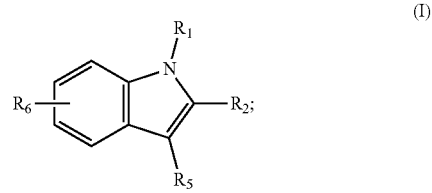

wherein:
$R_1$ is independently selected from H, $C_1$-$C_3$ alkyl;
$R_2$ is independently selected from —C(=O)—X—$R_3$, —S(=O)—X—$R_{3'}$;
X is a heteroatom independently selected from O;
$R_3$ and $R_{3'}$, independently of each other may be selected independently from H, $C_1$-$C_3$ alkyl;
$R_5$ is -L1-$R_7$-L2-$R_8$;
L1 and L2, independently of each other, are selected independently from —$(CH_2)_n$—; —NH—C(=O)—$(CH_2)_n$—, —C(=O)—NH—$(CH_2)_n$—; —S—S—$(CH_2)_n$—; —O—$(CH_2)_n$—; —NH—$(CH_2)_n$—C(=O)—$(CH_2)_n$—; —S—$(CH_2)_n$—; —NH—S(=O)$_n$—$(CH_2)_n$—;

n is independently 1 to 3;

R$_7$ is a carbocyclic ring or a heterocyclic ring;

R$_8$ is a mono cyclic ring system having 5 to 12 atoms, optionally substituted with at least one of OH, CF$_3$, halogen, —COOH, —NH$_2$, CN, C$_1$-C$_3$alkyl; and R$_6$ is independently selected from H, halogen, CN, NO$_2$, C$_1$-C$_3$ alkoxy, straight or branched C$_1$-C$_3$ alkyl.

10. The method according to claim 9, wherein said ARTS mimetic compound of the general formula (I) is at least one of:
(a) wherein R$_1$ is H;
(b) wherein R$_2$ is —C(═O)—X—R$_3$;
(c) wherein X is O;
(d) wherein L1 and L2 independently selected independently from each other from —NH—C(═O) —(CH$_2$)$_n$—, —(CH$_2$)$_n$—; and
(e) wherein R$_6$ is independently selected from the group consisting of H, halogen, CN, NO$_2$.

11. The method according to claim 9, wherein said ARTS mimetic compound including any stereoisomer or salt thereof having the general formula of any one of:
(a) formula (II)

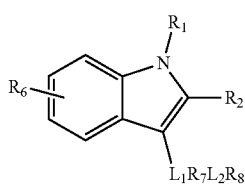

wherein R$_1$, R$_3$, R$_6$, R$_7$, R$_8$, L1 and L2 are as defined herein above;

(b) formula (III)

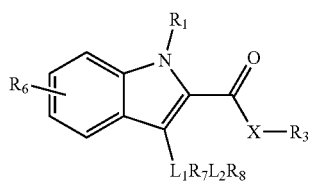

wherein R$_1$, R$_3$, R$_6$, R$_7$, R$_8$, L1 and L2 are as defined herein above;

(c) formula (IV)

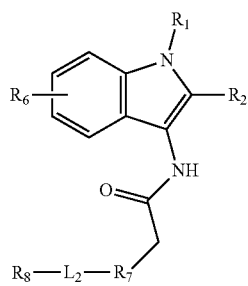

wherein R$_1$, R$_2$, R$_6$, R$_7$, R$_8$, and L2 are as defined herein above;

(d) formula (VI)

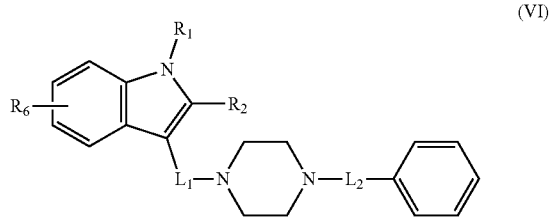

wherein R$_1$, R$_2$, R$_6$, L1 and L2 are as defined herein above.

12. The method according to claim 11, wherein said compound is 3-[2-(4-Benzyl-piperazin-1-yl)-acetylamino]-5-chloro-1H-indole-2-carboxylic acid methyl ester, having the structure:

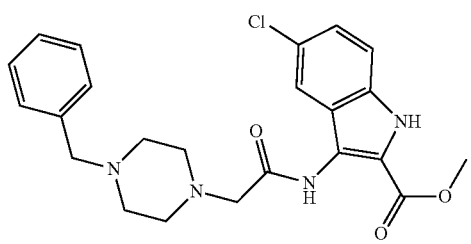 [SMILES: COC(=O)c1[nH]c2ccc(Cl)cc2c1NC(=O)CN1CCN(Cc2ccccc2)CC1]

including any stereoisomer or salt thereof.

13. The method according to claim 9, wherein said subject is a subject suffering from any one of a pre-malignant condition and carcinoma.

14. The method according to claim 13, wherein said carcinoma is a breast carcinoma.

15. The method according to claim 8, wherein said subject in need thereof is a subject suffering from a proliferative disorder, and wherein said method is for treating, inhibiting, reducing, eliminating, protecting or delaying the onset of a proliferative disorder in said subject.

16. The method according to claim 1, wherein said cell is pre-malignant or malignant epithelial cell in a subject, wherein said method is for inducing differentiation of said pre-malignant or malignant epithelial cells in said subject in need thereof, and wherein said contacting is by administering to said subject a therapeutically effective amount of said ARTS mimetic compound.

17. The method according to claim 1, wherein said cell is pre-malignant or malignant cell in a subject suffering from a proliferative disorder, and wherein said method is for treating, inhibiting, reducing, eliminating, protecting or delaying the onset of a proliferative disorder in said subject in need thereof.

18. The method of claim 1, wherein the step of contacting the cell comprises administering a therapeutically effective amount of the at least one ARTS mimetic compound or any vehicle, matrix, nano- or micro-particle or any composition comprising the same, the ARTS mimetic compound having the general formula (I) or a pharmaceutically acceptable salt or hydrate thereof to a subject, in need of treating, inhibiting, reducing, eliminating, protecting or delaying the onset of a proliferative disorder, for said treating, inhibiting, reducing, eliminating, protecting or delaying the onset of the proliferative disorder in said subject.

* * * * *

SEQUENCE LISTING

```
<160> NUMBER OF SEQ ID NOS: 27

<210> SEQ ID NO 1
<211> LENGTH: 274
<212> TYPE: PRT
<213> ORGANISM: Homo sapiens

<400> SEQUENCE: 1

Met Ile Lys Arg Phe Leu Glu Asp Thr Thr Asp Asp Gly Glu Leu Ser
1               5                   10                  15

Lys Phe Val Lys Asp Phe Ser Gly Asn Ala Ser Cys His Pro Pro Glu
                20                  25                  30

Ala Lys Thr Trp Ala Ser Arg Pro Gln Val Pro Glu Pro Arg Pro Gln
            35                  40                  45

Ala Pro Asp Leu Tyr Asp Asp Asp Leu Glu Phe Arg Pro Pro Ser Arg
        50                  55                  60

Pro Gln Ser Ser Asp Asn Gln Gln Tyr Phe Cys Ala Pro Ala Pro Leu
65                  70                  75                  80

Ser Pro Ser Ala Arg Pro Arg Ser Pro Trp Gly Lys Leu Asp Pro Tyr
                85                  90                  95

Asp Ser Ser Glu Asp Asp Lys Glu Tyr Val Gly Phe Ala Thr Leu Pro
            100                 105                 110

Asn Gln Val His Arg Lys Ser Val Lys Lys Gly Phe Asp Phe Thr Leu
        115                 120                 125

Met Val Ala Gly Glu Ser Gly Leu Gly Lys Ser Thr Leu Val Asn Ser
130                 135                 140

Leu Phe Leu Thr Asp Leu Tyr Arg Asp Arg Lys Leu Leu Gly Ala Glu
145                 150                 155                 160

Glu Arg Ile Met Gln Thr Val Glu Ile Thr Lys His Ala Val Asp Ile
                165                 170                 175

Glu Glu Lys Gly Val Arg Leu Arg Leu Thr Ile Val Asp Thr Pro Gly
            180                 185                 190

Phe Gly Asp Ala Val Asn Asn Thr Glu Cys Trp Lys Pro Val Ala Glu
        195                 200                 205

Tyr Ile Asp Gln Gln Phe Glu Gln Tyr Phe Arg Asp Glu Ser Gly Leu
    210                 215                 220

Asn Arg Lys Asn Ile Gln Asp Asn Arg Val His Cys Cys Leu Tyr Phe
225                 230                 235                 240

Ile Ser Pro Phe Gly His Gly Leu Arg Pro Leu Arg Leu Leu Ala
                245                 250                 255

Pro Pro Gly Ala Val Lys Gly Thr Gly Gln Glu His Gln Gly Gln Gly
```

Cys His

<210> SEQ ID NO 2
<211> LENGTH: 1911
<212> TYPE: DNA
<213> ORGANISM: Homo sapiens

<400> SEQUENCE: 2

```
cggcggtgct gcgaggtcgg cgcgcacgtc cgccgcgggt cgctcgggcg ctgtccaggc      60
ggagccggcc ccgcccgggc tgcagccatg atcaagcgtt tcctggagga caccacggat     120
gatggagaac tgagcaagtt cgtgaaggat ttctcaggaa atgcgagctg ccacccacca     180
gaggctaaga cctgggcatc caggcccaa gtcccggagc caaggcccca ggccccggac     240
ctctatgatg atgacctgga gttcagaccc ccctcgcggc ccagtcctc tgacaaccag      300
cagtacttct gtgccccagc ccctctcagc ccatctgcca ggccccgcag cccatggggc     360
aagcttgatc cctatgattc ctctgaggat gacaaggagt atgtgggctt gcaaccctc      420
cccaaccaag tccaccgaaa gtccgtgaag aaaggctttg actttaccct catggtggca     480
ggagagtctg gctgggcaa atccacactt gtcaatagcc tcttcctcac tgatctgtac     540
cgggaccgga aacttcttgg tgctgaagag aggatcatgc aaactgtgga gatcactaag     600
catgcagtgg acatagaaga aagggtgtg aggctgcggc tcaccattgt ggacacacca     660
ggttttgggg atgcagtcaa caacacagag tgctggaagc ctgtggcaga atacattgat     720
cagcagtttg agcagtattt ccgagacgag agtggcctga accgaaagaa catccaagac     780
aacagggtgc actgctgcct gtacttcatc tcacccttcg gccatggagta tggtccaagc     840
ctgaggctcc tggcaccacc gggtgctgtc aagggaacag ccaagagca ccaggggcag     900
ggctgccact agcaggtggt cacaggttcc tgttccccag gctccggcca ttggatgttg     960
aattcatgaa ggccctgcat cagcgggtca acatcgtgcc tatcctggct aaggcagaca    1020
cactgacacc tcccgaagtg accacaagaa acgcaaaat ccgggaggag attgagcatt     1080
ttggaatcaa gatctatcaa ttcccagact gtgactctga tgaggatgag gacttcaaat    1140
tgcaggacca agccctaaag gaaagcatcc catttgcagt aattggcagc aacactgtag    1200
tagaggccag agggcggcga gttcggggtc gactctaccc ctgggcatc gtggaagtgg      1260
aaaacccagg gcactgcgac tttgtgaagc tgaggacaat gctggtacgt acccacatgc    1320
aggacctgaa ggatgtgaca cgggagacac attatgagaa ctaccgggca cagtgcatcc    1380
agagcatgac ccgcctggtg gtgaaggaac ggaatcgcaa gtatgaccag aagccaggac    1440
aaagctggca gggggagatc ccaagcctag ccttgggtga ccaagccc tactttttgtt      1500
cttctatagg ccctgggctc aatctaagcg ggtgctgggg tcctcctcgc cttatcaacc    1560
cttttctccc tttagcaaac tgactcggga agtggtacc gacttcccca tccctgctgt      1620
cccaccaggg acagatccag aaactgagaa gcttatccga gagaaagatg aggagctgcg    1680
gcggatgcag gagatgctac acaaaataca aaaacagatg aaggagaact attaactggc    1740
tttcagccct ggatatttaa atctcctcct cttcttcctg tccatgccgg ccctcccag     1800
caccagctct gctcaggccc cttcagctac tgccacttcg ccttacatcc ctgctgactg    1860
cccagagact cagaggaaat aaagtttaat aaatctgtag gtggctaaaa a             1911
```

<210> SEQ ID NO 3
<211> LENGTH: 239

```
<212> TYPE: PRT
<213> ORGANISM: Homo sapiens

<400> SEQUENCE: 3

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

<210> SEQ ID NO 4
<211> LENGTH: 205
<212> TYPE: PRT
<213> ORGANISM: Homo sapiens

<400> SEQUENCE: 4

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110
```

```
Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
                180                 185                 190

Gly Gly Trp Val Gly Ala Leu Gly Asp Val Ser Leu Gly
        195                 200                 205

<210> SEQ ID NO 5
<211> LENGTH: 6492
<212> TYPE: DNA
<213> ORGANISM: Homo sapiens

<400> SEQUENCE: 5
tttctgtgaa gcagaagtct gggaatcgat ctggaaatcc tcctaatttt tactccctct      60
ccccgcgact cctgattcat tgggaagttt caaatcagct ataactggag agtgctgaag     120
attgatggga tcgttgcctt atgcatttgt tttggtttta caaaaaggaa acttgacaga     180
ggatcatgct gtacttaaaa aatacaacat cacagaggaa gtagactgat attaacaata     240
cttactaata ataacgtgcc tcatgaaata aagatccgaa aggaattgga ataaaaattt     300
cctgcatctc atgccaaggg ggaaacacca gaatcaagtg ttccgcgtga ttgaagacac     360
cccctcgtcc aagaatgcaa agcacatcca ataaaatagc tggattataa ctcctcttct     420
ttctctgggg gccgtggggt gggagctggg gcgagaggtg ccgttggccc ccgttgcttt     480
tcctctggga aggatggcgc acgctgggag aacagggtac gataaccggg agatagtgat     540
gaagtacatc cattataagc tgtcgcagag gggctacgag tgggatgcgg agatgtgggg     600
cgccgcgccc ccgggggccg ccccccgcac gggcatcttc tcctcccagc ccgggcacac     660
gccccatcca gccgcatccc gggacccggt cgccaggacc tcgccgctgc agacccccggc    720 tgccccccggc gccgccgcgg ggcctgcgct cagcccggtg ccacctgtgg tccacctgac     780
cctccgccag gccggcgacg acttctcccg ccgctaccgc cgcgacttcg ccagagatgtc    840 cagccagctg cacctgacgc ccttcaccgc gcggggacgc tttgccacgg tggtggagga     900
gctcttcagg gacggggtga actgggggag gattgtggcc ttctttgagt tcggtggggt     960
catgtgtgtg gagagcgtca accgggagat gtcgcccctg gtggacaaca tcgccctgtg    1020
gatgactgag tacctgaacc ggcacctgca cacctggatc caggataacg gaggctggga    1080
tgcctttgtg gaactgtacg gccccagcat gcggcctctg tttgatttct cctggctgtc    1140
tctgaagact ctgctcagtt tggccctggt gggagcttgc atcaccctgg gtgcctatct    1200
gggccacaag tgaagtcaac atgcctgccc caaacaaata tgcaaaggt tcactaaagc     1260 agtagaaata atatgcattg tcagtgatgt accatgaaac aaagctgcag gctgtttaag    1320
aaaaaataac acacatataa acatcacaca cacagacaga cacacacaca caacaatt      1380 aacagtcttc aggcaaaacg tcgaatcagc tatttactgc caagggaaa tatcatttat    1440 ttttacatt attaagaaaa aaagattat ttatttaaga cagtcccatc aaaactcctg     1500 tctttgaaa tccgaccact aattgccaag caccgcttcg tgtggctcca cctggatgtt     1560
ctgtgcctgt aaacatagat tcgctttcca tgttgttggc cggatcacca tctgaagagc    1620
```

```
agacggatgg aaaaaggacc tgatcattgg ggaagctggc tttctggctg ctggaggctg    1680
gggagaaggt gttcattcac ttgcatttct ttgccctggg ggctgtgata ttaacagagg    1740
gagggttcct gtgggggaa gtccatgcct ccctggcctg aagaagagac tctttgcata    1800
tgactcacat gatgcatacc tggtgggagg aaaagagttg ggaacttcag atggacctag    1860
tacccactga gatttccacg ccgaaggaca gcgatgggaa aaatgccctt aaatcatagg    1920
aaagtatttt tttaagctac caattgtgcc gagaaaagca ttttagcaat ttatacaata    1980
tcatccagta ccttaagccc tgattgtgta tattcatata ttttggatac gcacccccca    2040
actcccaata ctggctctgt ctgagtaaga aacagaatcc tctggaactt gaggaagtga    2100
acatttcggt gacttccgca tcaggaaggc tagagttacc cagagcatca ggccgccaca    2160
agtgcctgct tttaggagac cgaagtccgc agaacctgcc tgtgtcccag cttggaggcc    2220
tggtcctgga actgagccgg ggccctcact ggcctcctcc agggatgatc aacagggcag    2280
tgtggtctcc gaatgtctgg aagctgatgg agctcagaat tccactgtca agaaagagca    2340
gtagaggggt gtggctgggc ctgtcaccct ggggccctcc aggtaggccc gttttcacgt    2400
ggagcatggg agccacgacc cttcttaaga catgtatcac tgtagaggga aggaacagag    2460
gccctgggcc cttcctatca gaaggacatg gtgaaggctg ggaacgtgag gagaggcaat    2520
ggccacggcc cattttggct gtagcacatg gcacgttggc tgtgtggcct tggcccacct    2580
gtgagtttaa agcaaggctt taaatgactt tggagagggt cacaaatcct aaaagaagca    2640
ttgaagtgag gtgtcatgga ttaattgacc cctgtctatg gaattacatg taaaacatta    2700
tcttgtcact gtagtttggt tttatttgaa aacctgacaa aaaaaagtt ccaggtgtgg    2760 aatatggggg ttatctgtac atcctggggc attaaaaaaa aaatcaatgg tggggaacta    2820
taaagaagta acaaaagaag tgacatcttc agcaaataaa ctaggaaatt ttttttcttt    2880
ccagtttaga atcagccttg aaacattgat ggaataactc tgtggcatta ttgcattata    2940
taccatttat ctgtattaac tttggaatgt actctgttca atgtttaatg ctgtggttga    3000
tatttcgaaa gctgctttaa aaaatacat gcatctcagc gttttttgt ttttaattgt    3060 atttagttat ggcctataca ctatttgtga gcaaggtga tcgttttctg tttgagattt    3120
ttatctcttg attcttcaaa agcattctga gaaggtgaga taagccctga gtctcagcta    3180
cctaagaaaa acctggatgt cactggccac tgaggagctt tgtttcaacc aagtcatgtg    3240
catttccacg tcaacagaat tgtttattgt gacagttata tctgttgtcc ctttgacctt    3300
gtttcttgaa ggtttcctcg tccctgggca attccgcatt taattcatgg tattcaggat    3360
tacatgcatg tttggttaaa cccatgagat tcattcagtt aaaaatccag atggcaaatg    3420
accagcagat tcaaatctat ggtggtttga cctttagaga gttgctttac gtggcctgtt    3480
tcaacacaga cccacccaga gccctcctgc cctccttccg cgggggcttt ctcatggctg    3540
tccttcaggg tcttcctgaa atgcagtggt gcttacgctc caccaagaaa gcaggaaacc    3600
tgtggtatga agccagacct ccccggcggg cctcagggaa cagaatgatc agacctttga    3660
atgattctaa ttttttaagca aaatattatt ttatgaaagg tttacattgt caaagtgatg    3720
aatatggaat atccaatcct gtgctgctat cctgccaaaa tcattttaat ggagtcagtt    3780
tgcagtatgc tccacgtggt aagatcctcc aagctgcttt agaagtaaca atgaagaacg    3840
tggacgtttt taatataaag cctgtttgt cttttgttgt tgttcaaacg ggattcacag    3900
agtatttgaa aaatgtatat atattaagag gtcacggggg ctaattgctg gctggctgcc    3960
```

```
ttttgctgtg gggttttgtt acctggtttt aataacagta aatgtgccca gcctcttggc    4020
cccagaactg tacagtattg tggctgcact tgctctaaga gtagttgatg ttgcattttc    4080
cttattgtta aaacatgtt agaagcaatg aatgtatata aaagcctcaa ctagtcattt    4140
ttttctcctc ttctttttt tcattatatc taattatttt gcagttgggc aacagagaac    4200
catccctatt ttgtattgaa gagggattca catctgcatc ttaactgctc tttatgaatg    4260
aaaaaacagt cctctgtatg tactcctctt tacactggcc agggtcagag ttaaatagag    4320
tatatgcact ttccaaattg gggacaaggg ctctaaaaaa agccccaaaa ggagaagaac    4380
atctgagaac ctcctcggcc ctcccagtcc ctcgctgcac aaatactccg caagagaggc    4440
cagaatgaca gctgacaggg tctatggcca tcgggtcgtc tccgaagatt tggcaggggc    4500
agaaaactct ggcaggctta agatttggaa taaagtcaca gaattaagga agcacctcaa    4560
tttagttcaa acaagacgcc aacattctct ccacagctca cttacctctc tgtgttcaga    4620 tgtggcctte catttatatg tgatctttgt tttattagta aatgcttatc atctaaagat    4680
gtagctctgg cccagtggga aaaattagga agtgattata atcgagagg agttataata    4740 atcaagatta aatgtaaata atcagggcaa tcccaacaca tgtctagctt tcacctccag    4800
gatctattga gtgaacagaa ttgcaaatag tctctatttg taattgaact tatcctaaaa    4860
caaatagttt ataaatgtga acttaaactc taattaattc caactgtact tttaaggcag    4920
tggctgtttt tagactttct tatcacttat agttagtaat gtacacctac tctatcagag    4980
aaaaacagga aaggctcgaa atacaagcca ttctaaggaa attgggagt cagttgaaat    5040 tctattctga tcttattctg tggtgtcttt tgcagcccag acaaatgtgg ttacacactt    5100
tttaagaaat acaattctac attgtcaagc ttatgaaggt tccaatcaga tctttattgt    5160
tattcaattt ggatctttca gggatttttt ttttaaatta ttatgggaca aaggacattt    5220
gttggagggg tgggagggag gaagaatttt taaatgtaaa acattcccaa gtttggatca    5280
gggagttgga agttttcaga ataaccagaa ctaagggtat gaaggacctg tattggggtc    5340
gatgtgatgc ctctgcgaag aaccttgtgt gacaaatgag aaacattttg aagtttgtgg    5400 tacgacctt agattccaga gacatcagca tggctcaaag tgcagctccg tttggcagtg    5460
caatggtata aatttcaagc tggatatgtc taatgggtat ttaaacaata aatgtgcagt    5520
tttaactaac aggatattta atgacaacct tctggttggt agggacatct gtttctaaat    5580
gtttattatg tacaatacag aaaaaaattt tataaaatta agcaatgtga aactgaattg    5640
gagagtgata atacaagtcc tttagtctta cccagtgaat cattctgttc catgtctttg    5700
gacaaccatg accttggaca atcatgaaat atgcatctca ctggatgcaa agaaaatcag    5760
atggagcatg aatggtactg taccggttca tctggactgc cccagaaaaa taacttcaag    5820
caaacatcct atcaacaaca aggttgttct gcataccaag ctgagcacag aagatgggaa    5880
cactggtgga ggatggaaag gctcgctcaa tcaagaaaat tctgagacta ttaataaata    5940
agactgtagt gtagatactg agtaaatcca tgcacctaaa cctttggaa aatctgccgt    6000 gggccctcca gatagctcat ttcattaagt ttttccctcc aaggtagaat ttgcaagagt    6060
gacagtggat tgcatttctt ttggggaagc ttttctttgg tggttttgtt tattatacct    6120
tcttaagttt tcaaccaagg tttgcttttg ttttgagtta ctggggttat ttttgtttta    6180
aataaaaata agtgtacaat aagtgttttt gtattgaaag cttttgttat caagattttc    6240 atactttac cttccatggc tctttttaag attgatactt ttaagaggtg gctgatattc    6300
tgcaacactg tacacataaa aaatacggta aggatacttt acatggttaa ggtaaagtaa    6360
```

```
gtctccagtt ggccaccatt agctataatg gcactttgtt tgtgttgttg gaaaaagtca    6420
cattgccatt aaactttcct tgtctgtcta gttaatattg tgaagaaaaa taaagtacag    6480
tgtgagatac tg                                                        6492
```

<210> SEQ ID NO 6
<211> LENGTH: 1207
<212> TYPE: DNA
<213> ORGANISM: Homo sapiens

<400> SEQUENCE: 6

```
tttctgtgaa gcagaagtct gggaatcgat ctggaaatcc tcctaatttt tactccctct      60
ccccgcgact cctgattcat tgggaagttt caaatcagct ataactggag agtgctgaag     120
attgatggga tcgttgcctt atgcatttgt tttggtttta caaaaaggaa acttgacaga     180
ggatcatgct gtacttaaaa aatacaacat cacagaggaa gtagactgat attaacaata     240
cttactaata ataacgtgcc tcatgaaata aagatccgaa aggaattgga ataaaaattt     300
cctgcatctc atgccaaggg ggaaacacca gaatcaagtg ttccgcgtga ttgaagacac     360
cccctcgtcc aagaatgcaa agcacatcca ataaaatagc tggattataa ctcctcttct     420
ttctctgggg gccgtggggt gggagctggg gcgagaggtg ccgttggccc ccgttgcttt     480
tcctctggga aggatggcgc acgctgggag aacagggtac gataaccggg agatagtgat     540
gaagtacatc cattataagc tgtcgcagag gggctacgag tgggatgcgg agatgtggg      600 cgccgcgccc ccgggggccg ccccccgcacc gggcatcttc tcctcccagc ccgggcacac     660
gccccatcca gccgcatccc gggacccggt cgccaggacc tcgccgctgc agaccccggc     720 tgccccccggc gccgccgcgg ggcctgcgct cagcccggtg ccacctgtgg tccacctgac     780
cctccgccag gccggcgacg acttctcccg ccgctaccgc cgcgacttcg ccgagatgtc     840
cagccagctg cacctgacgc ccttcaccgc gcggggacgc tttgccacgg tggtggagga     900
gctcttcagg gacggggtga actggggggag gattgtggcc ttctttgagt tcggtggggt     960
catgtgtgtg gagagcgtca accgggagat gtcgcccctg gtggacaaca tcgcccctgtg    1020 gatgactgag tacctgaacc ggcacctgca cacctgggatc caggataacg gaggctgggg    1080
aggtgcactt ggtgatgtga gtctgggctg aggccacagg tccgagatgc gggggttgga    1140
gtgcgggtgg gctcctgggg caatgggagg ctgtggagcc ggcgaaataa aatcagagtt    1200
gttgcta                                                             1207
```

<210> SEQ ID NO 7
<211> LENGTH: 233
<212> TYPE: PRT
<213> ORGANISM: Homo sapiens

<400> SEQUENCE: 7

```
Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Ala His Ser Ser Ser Leu Asp Ala Arg Glu Val
65                  70                  75                  80
```

```
Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230

<210> SEQ ID NO 8
<211> LENGTH: 926
<212> TYPE: DNA
<213> ORGANISM: Homo sapiens

<400> SEQUENCE: 8
gaatctcttt ctctcccttc agaatcttat cttggctttg gatcttagaa gagaatcact      60
aaccagagac gagactcagt gagtgagcag gtgttttgga caatggactg gttgagccca     120
tccctattat aaaaatgtct cagagcaacc gggagctggt ggttgacttt ctctcctaca     180
agctttccca gaaaggatac agctggagtc agtttagtga tgtggaagag aacaggactg     240
aggcccagag agggactgaa tcggagatgg agacccccag tgccatcaat ggcaacccat     300
cctggcacct ggcagacagc cccgcggtga atggagccac tgcgcacagc agcagtttgg     360
atgcccggga ggtgatcccc atggcagcag taaagcaagc gctgagggag caggcgacg     420 agtttgaact gcgtaccgg cgggcattca gtgacctgac atcccagctc cacatcaccc     480
cagggacagc atatcagagc tttgaacagg tagtgaatga actcttccgg gatggggtaa     540 actgggtcg cattgtggcc ttttttctcct cggcgggc actgtgcgtg aaagcgtag     600 acaaggagat gcaggtattg gtgagtcgga tcgcagcttg gatggccact tacctgaatg     660
accacctaga gccttggatc caggagaacg gcggctggga cttttttgtg gaactctatg     720
ggaacaatgc agcagccgag agccgaaagg gccaggaacg cttcaaccgc tggttcctga     780
cgggcatgac tgtggccggc gtggttctgc tgggctcact cttcagtcgg aaatgaccag     840
acactgacca tccactctac cctcccaccc ccttctctgc tccaccacat cctccgtcca     900
gccgccattg ccaccaggag aacccg                                         926

<210> SEQ ID NO 9
<211> LENGTH: 497
<212> TYPE: PRT
<213> ORGANISM: Homo sapiens

<400> SEQUENCE: 9
```

-continued

```
Met Thr Phe Asn Ser Phe Glu Gly Ser Lys Thr Cys Val Pro Ala Asp
1               5                   10                  15

Ile Asn Lys Glu Glu Glu Phe Val Glu Phe Asn Arg Leu Lys Thr
            20                  25                  30

Phe Ala Asn Phe Pro Ser Gly Ser Pro Val Ser Ala Ser Thr Leu Ala
            35                  40                  45

Arg Ala Gly Phe Leu Tyr Thr Gly Glu Gly Asp Thr Val Arg Cys Phe
        50                  55                  60

Ser Cys His Ala Ala Val Asp Arg Trp Gln Tyr Gly Asp Ser Ala Val
65                  70                  75                  80

Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
            100                 105                 110

Gly Gln Tyr Lys Val Glu Asn Tyr Leu Gly Ser Arg Asp His Phe Ala
        115                 120                 125

Leu Asp Arg Pro Ser Glu Thr His Ala Asp Tyr Leu Leu Arg Thr Gly
    130                 135                 140

Gln Val Val Asp Ile Ser Asp Thr Ile Tyr Pro Arg Asn Pro Ala Met
145                 150                 155                 160

Tyr Ser Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
            180                 185                 190

Gly Ile Gly Asp Gln Val Gln Cys Phe Cys Gly Gly Lys Leu Lys
        195                 200                 205

Asn Trp Glu Pro Cys Asp Arg Ala Trp Ser Glu His Arg Arg His Phe
    210                 215                 220

Pro Asn Cys Phe Phe Val Leu Gly Arg Asn Leu Asn Ile Arg Ser Glu
225                 230                 235                 240

Ser Asp Ala Val Ser Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
            260                 265                 270

Gly Thr Trp Ile Tyr Ser Val Asn Lys Glu Gln Leu Ala Arg Ala Gly
        275                 280                 285

Phe Tyr Ala Leu Gly Glu Gly Asp Lys Val Lys Cys Phe His Cys Gly
    290                 295                 300

Gly Gly Leu Thr Asp Trp Lys Pro Ser Glu Asp Pro Trp Glu Gln His
305                 310                 315                 320

Ala Lys Trp Tyr Pro Gly Cys Lys Tyr Leu Leu Glu Gln Lys Gly Gln
                325                 330                 335

Glu Tyr Ile Asn Asn Ile His Leu Thr His Ser Leu Glu Glu Cys Leu
            340                 345                 350

Val Arg Thr Thr Glu Lys Thr Pro Ser Leu Thr Arg Arg Ile Asp Asp
        355                 360                 365

Thr Ile Phe Gln Asn Pro Met Val Gln Glu Ala Ile Arg Met Gly Phe
    370                 375                 380

Ser Phe Lys Asp Ile Lys Lys Ile Met Glu Glu Lys Ile Gln Ile Ser
385                 390                 395                 400

Gly Ser Asn Tyr Lys Ser Leu Glu Val Leu Val Ala Asp Leu Val Asn
                405                 410                 415

Ala Gln Lys Asp Ser Met Gln Asp Glu Ser Ser Gln Thr Ser Leu Gln
```

| | | 420 | | | 425 | | | | 430 | | |
|---|---|---|---|---|---|---|---|---|---|---|---|

Lys Glu Ile Ser Thr Glu Glu Gln Leu Arg Arg Leu Gln Glu Glu Lys
                                    435                 440                 445

Leu Cys Lys Ile Cys Met Asp Arg Asn Ile Ala Ile Val Phe Val Pro
        450                 455                 460

Cys Gly His Leu Val Thr Cys Lys Gln Cys Ala Glu Ala Val Asp Lys
465                 470                 475                 480

Cys Pro Met Cys Tyr Thr Val Ile Thr Phe Lys Gln Lys Ile Phe Met
                485                 490                 495

Ser

<210> SEQ ID NO 10
<211> LENGTH: 8460
<212> TYPE: DNA
<213> ORGANISM: Homo sapiens

<400> SEQUENCE: 10

```
gctggggcca agccgcagag cggagttggc atttccagat tggggctcgg gccgcgcctc      60
ctccgggacc ctccccttgg accgagccga tcgccgcggg gcagttcggg ccggctgtcc     120
tggcgcgaaa aggtggacaa gtcctatttt caagagaaga tgacttttaa cagttttgaa     180
ggatctaaaa cttgtgtacc tgcagacatc aataaggaag aagaatttgt agaagagttt     240
aatagattaa aaacttttgc taattttcca gtggtagtc ctgtttcagc atcaacactg     300
gcacgagcag ggtttcttta ctggtgaa ggagataccg tgcggtgctt tagttgtcat     360
gcagctgtag atagatggca atatggagac tcagcagttg aaagacacag gaaagtatcc     420
ccaaattgca gatttatcaa cggcttttat cttgaaaata gtgccacgca gtctacaaat     480
tctggtatcc agaatggtca gtacaaagtt gaaaactatc tgggaagcag agatcatttt     540
gccttagaca ggccatctga cacatgca gactatcttt tgagaactgg gcaggttgta     600
gatatatcag acaccatata cccgaggaac cctgccatgt atagtgaaga agctagatta     660
aagtcccttc agaactggcc agactatgct cacctaaccc aagagagtt agcaagtgct     720
ggactctact acacaggtat tggtgaccaa gtgcagtgct tttgttgtgg tggaaaactg     780
aaaaattggg aaccttgtga tcgtgcctgg tcagaacaca ggcgacactt tcctaattgc     840
ttctttgttt gggccggaa tcttaatatt cgaagtgaat ctgatgctgt gagttctgat     900
aggaatttcc caaattcaac aaatcttcca agaaatccat ccatggcaga ttatgaagca     960
cggatctta cttttggac atggatatac tcagttaaca aggagcagct tgcaagagct    1020
ggattttatg ctttaggtga aggtgataaa gtaaagtgct tcactgtggg aggagggcta    1080
actgattgga gcccagtga agaccttggg aacaacatg ctaaatggta tccagggtgc    1140
aaatatctgt tagaacagaa gggacaagaa tatataaaca atattcatt aactcattca    1200
cttgaggagt gtctggtaag aactactgag aaaacaccat cactaactag aagaattgat    1260
gataccatct tccaaaatcc tatggtacaa gaagctatac gaatggggtt cagtttcaag    1320
gacattaaga aataatggaa ggaaaaaatt cagatatctg ggagcaacta taatcactt    1380
gaggttctgg ttgcagatct agtgaatgct cagaaagaca gtatgcaaga tgagtcaagt    1440
cagacttcat tacagaaaga gattagtact gaagagcagc taaggcgcct gcaagaggag    1500
aagcttttgca aaatctgtat ggatagaaat attgctatcg ttttgttcc ttgtggacat    1560
ctagtcactt gtaaacaatg tgctgaagca gttgacaagt gtcccatgtg ctacacagtc    1620
attactttca gcaaaaaat ttttatgtct taatctaact ctatagtagg catgttatgt    1680
```

```
tgttcttatt accctgattg aatgtgtgat gtgaactgac tttaagtaat caggattgaa    1740
ttccattagc atttgctacc aagtaggaaa aaaaatgtac atggcagtgt tttagttggc    1800
aatataatct ttgaatttct tgattttca gggtattagc tgtattatcc attttttta     1860
ctgttattta attgaaacca tagactaaga ataagaagca tcatactata actgaacaca    1920
atgtgtattc atagtatact gatttaattt ctaagtgtaa gtgaattaat catctggatt    1980
ttttattctt ttcagatagg cttaacaaat ggagctttct gtatataaat gtggagatta    2040
gagttaatct ccccaatcac ataatttgtt ttgtgtgaaa aaggaataaa ttgttccatg    2100
ctggtggaaa gatagagatt gttttagag gttggttgtt gtgttttagg attctgtcca    2160
ttttctttta aagttataaa cacgtacttg tgcgaattat ttttttaaag tgatttgcca    2220
tttttgaaag cgtatttaat gatagaatac tatcgagcca acatgtactg acatggaaag    2280
atgtcaaaga tatgttaagt gtaaaatgca agtggcaaaa cactatgtat agtctgagcc    2340
agatcaaagt atgtatgttt ttaatatgca tagaacaaaa gatttggaaa gatatacacc    2400
aaactgttaa atgtggtttc tcttcgggga ggggggatt ggggagggg ccccagaggg      2460
gttttatagg ggccttttca ctttctactt ttttcatttt gttctgttcg aattttttat    2520
aagtatgtat tacttttgta atcagaattt ttagaaagta ttttgctgat ttaaaggctt    2580
aggcatgttc aaacgcctgc aaaactactt atcactcagc tttagttttt ctaatccaag    2640
aaggcagggc agttaacctt tttggtgcca atgtgaaatg taaatgattt tatgtttttc    2700
ctgctttgtg gatgaaaaat atttctgagt ggtagttttt tgacaggtag accatgtctt    2760
atcttgtttc aaaataagta tttctgattt tgtaaaatga aatataaat atgtctcaga    2820
tcttccaatt aattagtaag gattcatcct taatccttgc tagtttaagc ctgcctaagt    2880
cactttacta aaagatcttt gttaactcag tattttaaac atctgtcagc ttatgtaggt    2940
aaaagtagaa gcatgtttgt acactgcttg tagttatagt gacagctttc catgttgaga    3000
ttctcatatc atcttgtatc ttaaagtttc atgtgagttt ttaccgttag gatgattaag    3060
atgtatatag gacaaaatgt taagtctttc ctctacctac atttgttttc ttggctagta    3120
atagtagtag atacttctga aataaatgtt ctctcaagat ccttaaaacc tcttggaaat    3180
tataaaaata ttggcaagaa aagaagaata gttgtttaaa tattttttaa aaaacacttg    3240
aataagaatc agtagggtat aaactagaag tttaaaaatg cttcatagaa cgtccagggt    3300
ttacattaca agattctcac aacaaaccta ttgtagaggt gagtaaggca tgttactaca    3360
gaggaaagtt tgagagtaaa actgtaaaaa attatatttt tgttgtactt tctaagagaa    3420
agagtattgt tatgttctcc taacttctgt tgattactac tttaagtgat attcatttaa    3480
aacattgcaa atttatttta tttatttaat tttcttttg agatggagtc ttgcttgtca    3540
cccaggctgg agtgcagtgg agtgatctct gctcactgca acctccgcct tctgggttca    3600
agcgattctc gtgcctcagc ttcctgagta gctggaatta caggcaggtg ccaccatgcc    3660
cgactaattt tttttattt ttagtagaga cggggtttca ccatgttggc caggctggta    3720
tcaaactcct gacctcaaga gatccactcg ccttgccctc ccaaagtgct gggattacag    3780
gcttgagcca ccacgcccgg ctaaaacatt gcaaatttaa atgagagttt taaaaattaa    3840
ataatgactg ccctgtttct gttttagtat gtaaatcctc agttcttcac ctttgcactg    3900
tctgccactg agtttggtta tatagtcatt aacttgaatt tggtctgtat agtctagact    3960
ttaaatttaa agttttctac aaggggagaa aagtgttaaa attttttaaaa tatgttttcc    4020
```

```
aggacacttc acttccaagt caggtaggta gttcaatcta gttgttagcc aaggactcaa    4080
ggactgaatt gttttaacat aaggcttttc ctgttctggg agccgcactt cattaaaatt    4140
cttctaaaac ttgtatgttt agagttaagc aagacttttt ttcttcctct ccatgagttg    4200
tgaaatttaa tgcacaacgc tgatgtggct aacaagttta ttttaagaat tgtttagaaa    4260
tgctgttgct tcaggttctt aaaatcactc agcactccaa cttctaatca aatttttgga    4320
gacttaacag catttgtctg tgtttgaact ataaaaagca ccggatcttt tccatctaat    4380
tccgcaaaaa ttgatcattt gcaaagtcaa aactatagcc atatccaaat cttttccccc    4440
tcccaagagt tctcagtgtc tacatgtaga ctattccttt tctgtataaa gttcactcta    4500
ggatttcaag tcaccactta ttttacattt tagtcatgca aagattcaag tagttttgca    4560
ataagtactt atctttattt gtaataattt agtctgctga tcaaaagcat tgtcttaatt    4620
tttgagaact ggttttagca tttacaaact aaattccagt taattaatta atagctttat    4680
attgcctttc ctgctacatt tggtttttc ccctgtccct ttgattacgg gctaaggtag    4740
ggtagagtgg gtgtagtgag tgtatataat gtgatttggc cctgtgtatt atgatatttt    4800
gttatttttg ttgttatatt atttacattt cagtagttgt ttttttgtgtt tccattttag    4860 tggataaaat ttgtattttg aactatgaat ggagactacc gccccagcat tagtttcaca    4920
tgatataccc tttaaacccg aatcattgtt ttatttcctg attacacagg tgttgaatgg    4980 ggaaagggc tagtatatca gtaggatata ctatgggatg tatatatatc attgctgtta    5040
gagaaatgaa ataaaatggg ctgggctca gtggctcacg cctgtaatcc cagcactttg    5100
ggaggctgag gcaggtggat cacgaggtca ggagatcgag accatcctgg ctaacacggt    5160
gaaaccccgt ctctactaaa aacagaaaa ttagccgggc gtggtggcgg cgcctgtag    5220 tcccagctac tcgggaggct gaggcaggag aatggtgtga acccgggagg cagagcttgc    5280
agtgagccga gatctcgcca ctgcactcca gcctgggcaa cagagcaaga ctctgtctca    5340
aaaaaaaaaa aaaagaaat aagaaaatgg gaagcaatat ttgacatagt tcttttagt    5400 caaatctact tgttaaaaaa agggtagcag tttattcatc tgtgaaagga aataatact    5460 tatcttacaa ggttgcaaga gctcaaggag accatgtatg taaagttcct gctgtaaata    5520
tgaactccca tcctaatacc cttttacctc tctgtgggtt tgtcttgacc tggaaatttg    5580
ggctaaaact tagaaaaaat tcttacatga taactcagtg atgcttactc atagtttttg    5640
gtgtttctca tagataagat ataaatcagc tgggcgcggt ggctcatgcc tgtaatccca    5700
gcactttggg aggccgaggc gggcagatca cctgaggtcg ggagtcgag accagcctga    5760 ccaacatgga gaaaccccgt ctctactaaa aatacaaaat tagctgggcg tggtggctca    5820
tgcctgtaat cccagctact tgggaggctg aggcaggaga atcgcttgaa cccaggaggc    5880
ggaggttgtg gtgagcgaag atcgtgccat tgcactccag cctgggcaac aagagcaaaa    5940
ctctgtctca aaaaaaaaaa aagatataaa tcacaataaa taataggtc aatacaaatg    6000 ttagccaggc gtggtggcac atgcccatag tcgcagctac tctggaggca gaggcaggag    6060
gatcacttga gcccatgaat ttgaggcagc agtgagctat gattgtgcca ctgtactcca    6120
gtctgggtga cagagtgaga ccccatctct aaataaatag gtcaaaccct taaaatatt    6180 taaattctta aaaaattgaa aagattattc ttctcaaatt tagttgagct ttctaagaga    6240
agcaattggc ttttccccac ttcaataatc attttcagtt tgactcatac agttaacaca    6300
atgtgaattt cttcctcagc ataacagagt tatagaatga cagggctgga agtgacctta    6360
gagagtatcc agttctttca ttttacaggt gaggcaactg agactcaaag gtgatgtaat    6420
```

```
ttgtgcaaag attatagcta attagtagca gagccctgac tgggacatag tttgaaggtg    6480
aaaaacttca ccaagctacc tttcttgaaa ggtccaaatg tttatgtttt caactactct    6540
ttccactgta ccataacttt cactacatat taaatgacac tttataacta atataatagg    6600
acaatcatca atgcatatat agccagccct tcatatctgt gggttttgca tccatggatt    6660
caaccaagga ggaattgaaa acactgagaa aaaaaaaaa gaccacacaa taaaaaaaaa    6720
aaatacaaaa taatacaaag aaaaagccaa aattgtcata ctgttgttaa gcaacagtat    6780
aacaactatt tacatagcat taaggttggt gcaaaatgc aaaaaaaaaa aaagcaatta    6840
tttttaaacc aacctaatat attgtattag gtattaaagt catctggaca tgaattaaag    6900
tatatgatgc cagcctggac aaaaggcaaa accctgtctc tacaaaaaat acaaaaatta    6960
gctgggcatg gtggtgtgtg cctgtagtcc tggctactcc ggagcctgag gtgggaggat    7020
cgcttgagtc tgggaggcag aggctgcatt gagctatgat catggcactg cattccagcc    7080
tgggtgacag tgcaagacct tgtctcagaa taaataaagt atgtgatgaa gatgtgcata    7140
cattatatgc aaatactgtt tttttttttt ttaatttaaa cagtctcact gtgttgccca    7200
ggatggagtg caatggcaca atcttggctc atggcaaact ctgcctcgca agcagctggg    7260
actacaggca tgctccacgg tgcccagtta attttttttg tattcttagt agagacaggg    7320
tttcaccatg ttggccaggc tagtcttgaa tttctgacct caagtgattc atctcccaaa    7380
gtgctgggat tacaggcgtg agccaccacg gccggctaat ttttgtattt tttagtagtg    7440
actggtttcg cggtgttgac caggctggtc tcgaactcct gatctcaggt gatctgcctg    7500
cctcggcctc acaaagtgct gggattacag gtgtgaacca ctgctcccgg ccttgtgtga    7560
ttttatctaa gggacttaag cgtcctcagg tcctagggg tcgtgaaacc aaaaccccag    7620
ggatagcaag ggacaattgt atcttcaaag tagacaaatg gcgccgggca cggtggctca    7680
cgcctgtaat cccagcagtt tccgaggctg aggcaggcgg ctcacctgag gtcaggagtt    7740
ggagaccagc ctggccaaca tgctgaaacc ctgtctgtac aaaaatacaa aaatagctgg    7800
gcatggtggc gcatgcctgt agtcccagct actagagcga ctgaggcagg agaattgctt    7860
gaacctggga ggcggaggtt gcagggagcc aagatggcgc caccgcactc cagcctaggt    7920
gatagagtga gactccctct caaaaacaaa acaaaacaaa aaaattagac aaatgctaca    7980 ttaatgttg ggtggtcaga ttctactttg aatctgaagt ttgcagatat gcctatagat    8040
ttttggagtt taccactttc ttattctgta tcattaatgt aatattttaa attactatat    8100
atgttaccat ttttctggat ttagtaagaa atttgcagtt ttggtttgat gtaacaaggg    8160
ttttaatgta atttatgtta gattttgcat ttttttcatt actgttatat tttaacctga    8220
ctgactgatc taattgtatt agtattgtga ataatcatgt gaaatgtttt gagacagagt    8280
actatatttg tgaatataat tttatggttt ttttcactta gaacctttct gtgtggaaaa    8340
ctaagaaaat tgctttctgc tgtataatct ggcattcatt gtagattaaa gcttattttt    8400
ctgtgaataa aacgtattca ataaaatact attctttaaa attatatcat aaaaaaaaaa    8460
```

<210> SEQ ID NO 11
<211> LENGTH: 23
<212> TYPE: DNA
<213> ORGANISM: Artificial Sequence
<220> FEATURE:
<223> OTHER INFORMATION: Forward primer for human ARTS

<400> SEQUENCE: 11
gagacgagag tggcctgaac cga                                                    23

<210> SEQ ID NO 12
<211> LENGTH: 23
<212> TYPE: DNA
<213> ORGANISM: Artificial Sequence
<220> FEATURE:
<223> OTHER INFORMATION: Reverse primer for human ARTS

<400> SEQUENCE: 12
aacaggaacc tgtgaccacc tgc                                                    23

<210> SEQ ID NO 13
<211> LENGTH: 19
<212> TYPE: DNA
<213> ORGANISM: Artificial Sequence
<220> FEATURE:
<223> OTHER INFORMATION: Forward primer for human GAPDH

<400> SEQUENCE: 13
atggggaagg tgaaggtcg                                                         19

<210> SEQ ID NO 14
<211> LENGTH: 22
<212> TYPE: DNA
<213> ORGANISM: Artificial Sequence
<220> FEATURE:
<223> OTHER INFORMATION: Reverse primer for human GAPDH

<400> SEQUENCE: 14
ggggtcattg atggcaacaa ta                                                     22

<210> SEQ ID NO 15
<211> LENGTH: 18
<212> TYPE: DNA
<213> ORGANISM: Artificial Sequence
<220> FEATURE:
<223> OTHER INFORMATION: BH-3 mimetic compound (TW-37)

<400> SEQUENCE: 15
tctcccagcg tgcgccat                                                          18

<210> SEQ ID NO 16
<211> LENGTH: 27
<212> TYPE: PRT
<213> ORGANISM: Artificial Sequence
<220> FEATURE:
<223> OTHER INFORMATION: ARTS C' terminus

<400> SEQUENCE: 16

Tyr Gly Pro Ser Leu Arg Leu Leu Ala Pro Pro Gly Ala Val Lys Gly
1               5                   10                  15

Thr Gly Gln Glu His Gln Gly Gln Gly Cys His
            20                  25

<210> SEQ ID NO 17
<211> LENGTH: 9
<212> TYPE: PRT
<213> ORGANISM: Artificial Sequence
<220> FEATURE:
<223> OTHER INFORMATION: ARTS C' terminal fragment

<400> SEQUENCE: 17

Tyr Gly Pro Ser Leu Arg Leu Leu Ala
1               5

```
<210> SEQ ID NO 18
<211> LENGTH: 9
<212> TYPE: PRT
<213> ORGANISM: Artificial Sequence
<220> FEATURE:
<223> OTHER INFORMATION: ARTS C' terminal fragment

<400> SEQUENCE: 18

Pro Pro Gly Ala Val Lys Gly Thr Gly
1               5

<210> SEQ ID NO 19
<211> LENGTH: 9
<212> TYPE: PRT
<213> ORGANISM: Artificial Sequence
<220> FEATURE:
<223> OTHER INFORMATION: ARTS C' terminal fragment

<400> SEQUENCE: 19

Gln Glu His Gln Gly Gln Gly Cys His
1               5

<210> SEQ ID NO 20
<211> LENGTH: 128
<212> TYPE: PRT
<213> ORGANISM: Artificial Sequence
<220> FEATURE:
<223> OTHER INFORMATION: ARTS N' terminal fragment residues 1-128

<400> SEQUENCE: 20

Met Ile Lys Arg Phe Leu Glu Asp Thr Thr Asp Asp Gly Glu Leu Ser
1               5                   10                  15

Lys Phe Val Lys Asp Phe Ser Gly Asn Ala Ser Cys His Pro Pro Glu
            20                  25                  30

Ala Lys Thr Trp Ala Ser Arg Pro Gln Val Pro Glu Pro Arg Pro Gln
        35                  40                  45

Ala Pro Asp Leu Tyr Asp Asp Leu Glu Phe Arg Pro Pro Ser Arg
    50                  55                  60

Pro Gln Ser Ser Asp Asn Gln Gln Tyr Phe Cys Ala Pro Ala Pro Leu
65                  70                  75                  80

Ser Pro Ser Ala Arg Pro Arg Ser Pro Trp Gly Lys Leu Asp Pro Tyr
                85                  90                  95

Asp Ser Ser Glu Asp Asp Lys Glu Tyr Val Gly Phe Ala Thr Leu Pro
                100                 105                 110

Asn Gln Val His Arg Lys Ser Val Lys Lys Gly Phe Asp Phe Thr Leu
            115                 120                 125

<210> SEQ ID NO 21
<211> LENGTH: 148
<212> TYPE: PRT
<213> ORGANISM: Artificial Sequence
<220> FEATURE:
<223> OTHER INFORMATION: ARTS N' terminal fragment residues 1-148

<400> SEQUENCE: 21

Met Ile Lys Arg Phe Leu Glu Asp Thr Thr Asp Asp Gly Glu Leu Ser
1               5                   10                  15

Lys Phe Val Lys Asp Phe Ser Gly Asn Ala Ser Cys His Pro Pro Glu
            20                  25                  30

Ala Lys Thr Trp Ala Ser Arg Pro Gln Val Pro Glu Pro Arg Pro Gln
        35                  40                  45
```

Ala Pro Asp Leu Tyr Asp Asp Leu Glu Phe Arg Pro Pro Ser Arg
    50                  55                  60

Pro Gln Ser Ser Asp Asn Gln Gln Tyr Phe Cys Ala Pro Ala Pro Leu
 65                  70                  75                  80

Ser Pro Ser Ala Arg Pro Arg Ser Pro Trp Gly Lys Leu Asp Pro Tyr
                 85                  90                  95

Asp Ser Ser Glu Asp Asp Lys Glu Tyr Val Gly Phe Ala Thr Leu Pro
                100                 105                 110

Asn Gln Val His Arg Lys Ser Val Lys Lys Gly Phe Asp Phe Thr Leu
                115                 120                 125

Met Val Ala Gly Glu Ser Gly Leu Gly Lys Ser Thr Leu Val Asn Ser
130                 135                 140

Leu Phe Leu Thr
145

<210> SEQ ID NO 22
<211> LENGTH: 43
<212> TYPE: PRT
<213> ORGANISM: Artificial Sequence
<220> FEATURE:
<223> OTHER INFORMATION: ARTS N' terminal fragment residues 106-148

<400> SEQUENCE: 22

Val Gly Phe Ala Thr Leu Pro Asn Gln Val His Arg Lys Ser Val Lys
 1               5                  10                  15

Lys Gly Phe Asp Phe Thr Leu Met Val Ala Gly Glu Ser Gly Leu Gly
                20                  25                  30

Lys Ser Thr Leu Val Asn Ser Leu Phe Leu Thr
            35                  40

<210> SEQ ID NO 23
<211> LENGTH: 28
<212> TYPE: PRT
<213> ORGANISM: Artificial Sequence
<220> FEATURE:
<223> OTHER INFORMATION: ARTS N' terminal fragment residues 106-133

<400> SEQUENCE: 23

Val Gly Phe Ala Thr Leu Pro Asn Gln Val His Arg Lys Ser Val Lys
 1               5                  10                  15

Lys Gly Phe Asp Phe Thr Leu Met Val Ala Gly Glu
                20                  25

<210> SEQ ID NO 24
<211> LENGTH: 23
<212> TYPE: PRT
<213> ORGANISM: Artificial Sequence
<220> FEATURE:
<223> OTHER INFORMATION: ARTS N' terminal fragment residues 106-128

<400> SEQUENCE: 24

Val Gly Phe Ala Thr Leu Pro Asn Gln Val His Arg Lys Ser Val Lys
 1               5                  10                  15

Lys Gly Phe Asp Phe Thr Leu
                20

<210> SEQ ID NO 25
<211> LENGTH: 37
<212> TYPE: PRT
<213> ORGANISM: Artificial Sequence
<220> FEATURE:
<223> OTHER INFORMATION: ARTS N' terminal fragment residues 112-148

```
<400> SEQUENCE: 25

Pro Asn Gln Val His Arg Lys Ser Val Lys Lys Gly Phe Asp Phe Thr
1               5                   10                  15

Leu Met Val Ala Gly Glu Ser Gly Leu Gly Lys Ser Thr Leu Val Asn
                20                  25                  30

Ser Leu Phe Leu Thr
        35

<210> SEQ ID NO 26
<211> LENGTH: 37
<212> TYPE: PRT
<213> ORGANISM: Artificial Sequence
<220> FEATURE:
<223> OTHER INFORMATION: ARTS N' terminal fragment residues 112-133

<400> SEQUENCE: 26

Pro Asn Gln Val His Arg Lys Ser Val Lys Lys Gly Phe Asp Phe Thr
1               5                   10                  15

Leu Met Val Ala Gly Glu Ser Gly Leu Gly Lys Ser Thr Leu Val Asn
                20                  25                  30

Ser Leu Phe Leu Thr
        35

<210> SEQ ID NO 27
<211> LENGTH: 17
<212> TYPE: PRT
<213> ORGANISM: Artificial Sequence
<220> FEATURE:
<223> OTHER INFORMATION: ARTS N' terminal fragment 112-128

<400> SEQUENCE: 27

Pro Asn Gln Val His Arg Lys Ser Val Lys Lys Gly Phe Asp Phe Thr
1               5                   10                  15

Leu
```